US009002073B2

(12) United States Patent
Hanna et al.

(10) Patent No.: US 9,002,073 B2
(45) Date of Patent: Apr. 7, 2015

(54) MOBILE IDENTITY PLATFORM

(71) Applicant: EyeLock, Inc., Caguas, PR (US)

(72) Inventors: Keith J. Hanna, New York, NY (US); Gary Alan Greene, West Windsor, NJ (US); David James Hirvonen, Brooklyn, NY (US); George Herbert Needham Riddle, Princeton, NJ (US)

(73) Assignee: EyeLock, Inc., Tolima Valley Caguas, PR (US)

( * ) Notice: Subject to any disclaimer, the term of this patent is extended or adjusted under 35 U.S.C. 154(b) by 0 days.

(21) Appl. No.: 13/773,159

(22) Filed: Feb. 21, 2013

(65) Prior Publication Data

US 2013/0162798 A1 Jun. 27, 2013

Related U.S. Application Data

(63) Continuation-in-part of application No. 13/440,707, filed on Apr. 5, 2012, which is a continuation-in-part of application No. 13/398,562, filed on Feb. 16, 2012, which is a continuation-in-part of application No.

(Continued)

(51) Int. Cl.
*G06K 9/00* (2006.01)
*A61B 3/14* (2006.01)
(Continued)

(52) U.S. Cl.
CPC .............. *A61B 3/14* (2013.01); *A61B 3/0091* (2013.01); *A61B 5/117* (2013.01); *A61B 5/7203* (2013.01); *G06K 9/00604* (2013.01); *G06K 9/00912* (2013.01); *A61B 2576/00* (2013.01)

(58) Field of Classification Search
CPC .......... G06K 9/00604; G06K 9/00597; G06K 9/0061; G06K 9/00617; G06K 9/00892; G06K 9/00906; G06K 9/036; G06K 9/2027; G06K 9/00288; G06K 9/00255; G06K 9/00281; H04N 5/23219; H04N 2101/00; G07C 9/00158; A61B 5/117; A61B 3/14; A61B 3/1216; G06F 21/32
USPC ........................................ 382/115, 124, 117
See application file for complete search history.

(56) References Cited

U.S. PATENT DOCUMENTS 4,231,661 A  11/1980  Walsh et al.
4,641,349 A   2/1987  Flom et al.
(Continued)

FOREIGN PATENT DOCUMENTS

JP    2007-249556     9/2007
KR    10-2009-0086891  8/2009
(Continued)

OTHER PUBLICATIONS

Ma et al, "Personal Identification Based on Iris Texture Analysis", Dec. 2003, IEEE: Pattern Analysis and Machine Intelligence, vol. 25, No. 12, pp. 1519-1533.*

(Continued)

*Primary Examiner* — Edward Park
(74) *Attorney, Agent, or Firm* — Cooley LLP

(57) ABSTRACT

The present disclosure is directed towards a compact, mobile apparatus for iris image acquisition, adapted to address effects of ocular dominance in the subject and to guide positioning of the subject's iris for the image acquisition. The apparatus may include a sensor for acquiring an iris image from a subject. A compact mirror may be oriented relative to a dominant eye of the subject, and sized to present an image of a single iris to the subject when the apparatus is positioned at a suitable distance for image acquisition. The mirror may assist the subject in positioning the iris for iris image acquisition. The mirror may be positioned between the sensor and the iris during iris image acquisition, and transmit a portion of light reflected off the iris to the sensor.

10 Claims, 74 Drawing Sheets

Related U.S. Application Data

12/675,189, filed as application No. PCT/US2008/074737 on Aug. 29, 2008, now Pat. No. 8,553,948.

(60) Provisional application No. 60/969,607, filed on Sep. 1, 2007, provisional application No. 61/472,270, filed on Apr. 6, 2011, provisional application No. 61/472,279, filed on Apr. 6, 2011, provisional application No. 61/443,757, filed on Feb. 17, 2011.

(51) Int. Cl.
*A61B 3/00* (2006.01)
*A61B 5/117* (2006.01)
*A61B 5/00* (2006.01)

(56) References Cited

U.S. PATENT DOCUMENTS

| | | | |
|---|---|---|---|
| 4,910,725 A | 3/1990 | Drexler et al. |
| 4,923,263 A | 5/1990 | Johnson |
| 5,140,469 A | 8/1992 | Lamarre et al. |
| 5,259,040 A | 11/1993 | Hanna |
| 5,291,560 A | 3/1994 | Daugman |
| 5,488,675 A | 1/1996 | Hanna |
| 5,572,596 A | 11/1996 | Wildes et al. |
| 5,581,629 A | 12/1996 | Hanna et al. |
| 5,613,012 A | 3/1997 | Hoffman et al. |
| 5,615,277 A | 3/1997 | Hoffman |
| 5,737,439 A | 4/1998 | Lapsley et al. |
| 5,751,836 A | 5/1998 | Wildes |
| 5,764,789 A | 6/1998 | Pare et al. |
| 5,802,199 A | 9/1998 | Pare et al. |
| 5,805,719 A | 9/1998 | Pare et al. |
| 5,838,812 A | 11/1998 | Pare et al. |
| 5,901,238 A | 5/1999 | Matsushita |
| 5,953,440 A | 9/1999 | Zhang et al. |
| 5,978,494 A * | 11/1999 | Zhang ........................... 382/117 |
| 6,021,210 A | 2/2000 | Camus et al. |
| 6,028,949 A | 2/2000 | McKendall |
| 6,055,322 A | 4/2000 | Salganicoff |
| 6,064,752 A | 5/2000 | Rozmus et al. |
| 6,069,967 A | 5/2000 | Rozmus et al. |
| 6,088,470 A | 7/2000 | Camus |
| 6,144,754 A | 11/2000 | Okano et al. |
| 6,149,061 A | 11/2000 | Massieu et al. |
| 6,192,142 B1 | 2/2001 | Pare et al. |
| 6,222,903 B1 | 4/2001 | Kim et al. |
| 6,246,751 B1 | 6/2001 | Bergl et al. |
| 6,247,813 B1 | 6/2001 | Kim et al. |
| 6,252,977 B1 | 6/2001 | Salganicoff et al. |
| 6,289,113 B1 | 9/2001 | McHugh et al. |
| 6,320,610 B1 | 11/2001 | Van Sant et al. |
| 6,349,171 B1 | 2/2002 | Koike |
| 6,366,682 B1 | 4/2002 | Hoffman et al. |
| 6,373,968 B2 | 4/2002 | Okano et al. |
| 6,377,699 B1 | 4/2002 | Musgrave et al. |
| 6,424,727 B1 | 7/2002 | Musgrave et al. |
| 6,483,930 B1 | 11/2002 | Musgrave et al. |
| 6,532,298 B1 | 3/2003 | Cambier et al. |
| 6,542,624 B1 | 4/2003 | Oda |
| 6,545,810 B1 | 4/2003 | Takada et al. |
| 6,546,121 B1 | 4/2003 | Oda |
| 6,554,705 B1 | 4/2003 | Cumbers |
| 6,587,597 B1 | 7/2003 | Nakao et al. |
| 6,594,376 B2 | 7/2003 | Hoffman et al. |
| 6,594,377 B1 | 7/2003 | Kim et al. |
| 6,652,099 B2 | 11/2003 | Chae et al. |
| 6,700,998 B1 | 3/2004 | Murata |
| 6,701,029 B1 | 3/2004 | Berfanger et al. |
| 6,714,665 B1 | 3/2004 | Hanna et al. |
| 6,760,467 B1 | 7/2004 | Min et al. |
| 6,763,148 B1 | 7/2004 | Sternberg et al. |
| 6,819,219 B1 | 11/2004 | Bolle et al. |
| 6,832,044 B2 | 12/2004 | Doi et al. |
| 6,850,631 B1 * | 2/2005 | Oda et al. ........................ 382/117 |
| 6,917,695 B2 | 7/2005 | Teng et al. |
| 6,920,236 B2 | 7/2005 | Prokoski |
| 6,930,707 B2 | 8/2005 | Bates et al. |
| 6,944,318 B1 | 9/2005 | Takata et al. |
| 6,950,536 B2 | 9/2005 | Houvener |
| 6,980,670 B1 | 12/2005 | Hoffman et al. |
| 6,985,608 B2 | 1/2006 | Hoffman et al. |
| 7,007,298 B1 | 2/2006 | Shinzaki et al. |
| 7,020,351 B1 | 3/2006 | Kumar |
| 7,047,418 B1 | 5/2006 | Ferren et al. |
| 7,095,901 B2 | 8/2006 | Lee et al. |
| 7,106,366 B2 | 9/2006 | Parker et al. |
| 7,146,027 B2 | 12/2006 | Kim et al. |
| 7,152,782 B2 | 12/2006 | Shenker et al. |
| 7,209,271 B2 | 4/2007 | Lewis et al. |
| 7,212,330 B2 | 5/2007 | Seo et al. |
| 7,221,486 B2 * | 5/2007 | Makihira et al. ............... 358/486 |
| 7,248,719 B2 | 7/2007 | Hoffman et al. |
| 7,271,939 B2 | 9/2007 | Kono |
| 7,346,472 B1 | 3/2008 | Moskowitz et al. |
| 7,385,626 B2 | 6/2008 | Aggarwal et al. |
| 7,398,925 B2 | 7/2008 | Tidwell et al. |
| 7,414,737 B2 | 8/2008 | Cottard et al. |
| 7,418,115 B2 | 8/2008 | Northcott et al. |
| 7,428,320 B2 | 9/2008 | Northcott et al. |
| 7,542,590 B1 | 6/2009 | Robinson et al. |
| 7,545,962 B2 | 6/2009 | Peirce et al. |
| 7,558,406 B1 | 7/2009 | Robinson et al. |
| 7,558,407 B2 | 7/2009 | Hoffman et al. |
| 7,574,021 B2 | 8/2009 | Matey |
| 7,583,822 B2 | 9/2009 | Guillemot et al. |
| 7,606,401 B2 | 10/2009 | Hoffman et al. |
| 7,616,788 B2 | 11/2009 | Hsieh et al. |
| 7,639,840 B2 | 12/2009 | Hanna et al. |
| 7,660,700 B2 | 2/2010 | Moskowitz et al. |
| 7,693,307 B2 | 4/2010 | Rieul et al. |
| 7,697,786 B2 | 4/2010 | Camus et al. |
| 7,715,595 B2 | 5/2010 | Kim et al. |
| 7,719,566 B2 | 5/2010 | Guichard |
| 7,760,919 B2 * | 7/2010 | Namgoong .................... 382/117 |
| 7,770,019 B2 | 8/2010 | Ferren et al. |
| 7,797,606 B2 | 9/2010 | Chabanne |
| 7,801,335 B2 | 9/2010 | Hanna |
| 7,847,688 B2 | 12/2010 | Bernard et al. |
| 7,869,627 B2 | 1/2011 | Northcott et al. |
| 7,912,252 B2 | 3/2011 | Ren et al. |
| 7,916,908 B1 * | 3/2011 | Thomas ....................... 382/124 |
| 7,925,059 B2 | 4/2011 | Hoyos et al. |
| 7,929,017 B2 | 4/2011 | Aggarwal |
| 7,929,732 B2 | 4/2011 | Bringer et al. |
| 7,949,295 B2 | 5/2011 | Kumar |
| 7,949,494 B2 | 5/2011 | Moskowitz et al. |
| 7,978,883 B2 | 7/2011 | Rouh et al. |
| 8,009,876 B2 | 8/2011 | Kim et al. |
| 8,025,399 B2 | 9/2011 | Northcott et al. |
| 8,028,896 B2 | 10/2011 | Carter et al. |
| 8,090,246 B2 | 1/2012 | Jelinek |
| 8,092,021 B1 | 1/2012 | Northcott et al. |
| 8,132,912 B1 | 3/2012 | Northcott et al. |
| 8,159,328 B2 | 4/2012 | Luckhardt |
| 8,170,295 B2 | 5/2012 | Fujii et al. |
| 8,181,858 B2 | 5/2012 | Carter et al. |
| 8,195,044 B2 | 6/2012 | Hanna |
| 8,212,870 B2 | 7/2012 | Hanna |
| 8,214,175 B2 | 7/2012 | Moskowitz et al. |
| 8,233,680 B2 | 7/2012 | Bringer et al. |
| 8,243,133 B1 | 8/2012 | Northcott et al. |
| 8,260,008 B2 | 9/2012 | Hanna |
| 8,279,042 B2 | 10/2012 | Beenau et al. |
| 8,280,120 B2 | 10/2012 | Hoyos |
| 8,289,390 B2 | 10/2012 | Aggarwal |
| 8,306,279 B2 | 11/2012 | Hanna |
| 8,317,325 B2 | 11/2012 | Raguin et al. |
| 8,364,646 B2 | 1/2013 | Hanna |
| 8,411,909 B1 | 4/2013 | Zhao et al. |
| 8,442,339 B2 | 5/2013 | Martin et al. |
| 8,443,202 B2 | 5/2013 | White et al. |
| 8,553,948 B2 | 10/2013 | Hanna et al. |
| 8,604,901 B2 | 12/2013 | Hoyos |

(56) References Cited

U.S. PATENT DOCUMENTS

| | | |
|---|---|---|
| 8,606,097 B2 | 12/2013 | Hanna |
| 2002/0110286 A1 | 8/2002 | Cheatle et al. |
| 2002/0131623 A1* | 9/2002 | Musgrave et al. ............ 382/117 |
| 2002/0136435 A1* | 9/2002 | Prokoski ....................... 382/118 |
| 2003/0151674 A1 | 8/2003 | Lin |
| 2004/0013288 A1 | 1/2004 | Svensson et al. |
| 2005/0084137 A1 | 4/2005 | Kim et al. |
| 2005/0084179 A1 | 4/2005 | Hanna |
| 2005/0105778 A1* | 5/2005 | Sung et al. .................... 382/115 |
| 2005/0226471 A1 | 10/2005 | Singh |
| 2005/0264758 A1* | 12/2005 | Wakamori ..................... 351/206 |
| 2005/0285943 A1* | 12/2005 | Cutler ......................... 348/207.1 |
| 2006/0028552 A1 | 2/2006 | Aggarwal |
| 2006/0029262 A1 | 2/2006 | Fujimatsu et al. |
| 2006/0073449 A1 | 4/2006 | Kumar |
| 2006/0074986 A1 | 4/2006 | Mallalieu et al. |
| 2006/0097172 A1 | 5/2006 | Park |
| 2006/0120707 A1* | 6/2006 | Kusakari et al. ................ 396/18 |
| 2006/0170813 A1 | 8/2006 | Morofuji |
| 2006/0188169 A1 | 8/2006 | Tener et al. |
| 2006/0204121 A1 | 9/2006 | Bryll |
| 2006/0279630 A1 | 12/2006 | Aggarwal |
| 2007/0098229 A1* | 5/2007 | Wu et al. ....................... 382/118 |
| 2007/0110285 A1 | 5/2007 | Hanna |
| 2007/0188613 A1 | 8/2007 | Nobori et al. |
| 2007/0206839 A1 | 9/2007 | Hanna |
| 2007/0211922 A1 | 9/2007 | Crowley et al. |
| 2007/0286462 A1* | 12/2007 | Usher et al. ................... 382/115 |
| 2008/0031610 A1 | 2/2008 | Border et al. |
| 2008/0044063 A1 | 2/2008 | Friedman et al. |
| 2008/0122578 A1 | 5/2008 | Hoyos |
| 2008/0291279 A1 | 11/2008 | Samarasekera |
| 2009/0074256 A1 | 3/2009 | Haddad |
| 2009/0097715 A1 | 4/2009 | Cottard et al. |
| 2009/0161925 A1 | 6/2009 | Cottard et al. |
| 2009/0207251 A1 | 8/2009 | Kobayashi et al. |
| 2009/0219405 A1 | 9/2009 | Kaneda et al. |
| 2009/0231096 A1 | 9/2009 | Bringer et al. |
| 2009/0232418 A1 | 9/2009 | Lolacono et al. |
| 2009/0268045 A1 | 10/2009 | Sur et al. |
| 2009/0274345 A1 | 11/2009 | Hanna |
| 2009/0278922 A1 | 11/2009 | Tinker et al. |
| 2010/0014720 A1 | 1/2010 | Hoyos |
| 2010/0021016 A1 | 1/2010 | Cottard et al. |
| 2010/0033677 A1 | 2/2010 | Jelinek |
| 2010/0074477 A1 | 3/2010 | Fujii et al. |
| 2010/0127826 A1 | 5/2010 | Saliba et al. |
| 2010/0201853 A1 | 8/2010 | Ishiga |
| 2010/0232655 A1 | 9/2010 | Hanna |
| 2010/0238407 A1 | 9/2010 | Dai |
| 2010/0246903 A1 | 9/2010 | Cottard |
| 2010/0253816 A1 | 10/2010 | Hanna |
| 2010/0278394 A1 | 11/2010 | Raguin et al. |
| 2010/0310070 A1 | 12/2010 | Bringer et al. |
| 2011/0002510 A1 | 1/2011 | Hanna |
| 2011/0007949 A1 | 1/2011 | Hanna |
| 2011/0119111 A1 | 5/2011 | Hanna |
| 2011/0119141 A1 | 5/2011 | Hoyos |
| 2011/0158486 A1 | 6/2011 | Bringer et al. |
| 2011/0194738 A1 | 8/2011 | Choi et al. |
| 2011/0211054 A1 | 9/2011 | Hanna |
| 2011/0277518 A1 | 11/2011 | Lais et al. |
| 2012/0127295 A9 | 5/2012 | Hanna |
| 2012/0187838 A1 | 7/2012 | Hanna |
| 2012/0212597 A1 | 8/2012 | Hanna |
| 2012/0219279 A1 | 8/2012 | Hanna |
| 2012/0239458 A9 | 9/2012 | Hanna |
| 2012/0240223 A1 | 9/2012 | Tu |
| 2012/0242820 A1 | 9/2012 | Hanna et al. |
| 2012/0242821 A1 | 9/2012 | Hanna |
| 2012/0243749 A1 | 9/2012 | Hanna |
| 2012/0257797 A1 | 10/2012 | Leyvand et al. |
| 2012/0268241 A1 | 10/2012 | Hanna |
| 2012/0293643 A1 | 11/2012 | Hanna |
| 2012/0300052 A1 | 11/2012 | Hanna |
| 2012/0300990 A1 | 11/2012 | Hanna |
| 2012/0321141 A1 | 12/2012 | Hoyos |
| 2012/0328164 A1 | 12/2012 | Hoyos |
| 2013/0051631 A1 | 2/2013 | Hanna |
| 2013/0093838 A1 | 4/2013 | Tan et al. |
| 2013/0108125 A1 | 5/2013 | Storm et al. |
| 2013/0110859 A1 | 5/2013 | Hanna |
| 2013/0162799 A1 | 6/2013 | Hanna |
| 2013/0182093 A1 | 7/2013 | Hanna et al. |
| 2013/0182094 A1 | 7/2013 | Hanna et al. |
| 2013/0182095 A1 | 7/2013 | Hanna et al. |
| 2013/0182913 A1 | 7/2013 | Hoyos |
| 2013/0182915 A1 | 7/2013 | Hanna |
| 2013/0194408 A1 | 8/2013 | Hanna |
| 2013/0212655 A1 | 8/2013 | Hoyos |
| 2013/0251215 A1 | 9/2013 | Coons |
| 2013/0294659 A1 | 11/2013 | Hanna |
| 2014/0064574 A1 | 3/2014 | Hanna |
| 2014/0072183 A1 | 3/2014 | Hanna |

FOREIGN PATENT DOCUMENTS

| | | |
|---|---|---|
| KR | 10-2009-0106791 A | 10/2009 |
| KR | 10-2010-0049407 | 5/2010 |
| WO | WO-2008/054396 | 5/2008 |
| WO | WO 2008/054396 | 5/2008 |
| WO | WO 2009/029757 A1 | 3/2009 |
| WO | WO 2009/029765 A1 | 3/2009 |
| WO | WO-2010/062371 | 6/2010 |
| WO | WO 2010/062371 | 6/2010 |
| WO | WO-2011/093538 | 8/2011 |
| WO | WO 2011/093538 | 8/2011 |
| WO | WO 2012/112788 A2 | 8/2012 |
| WO | WO 2013/109295 A2 | 7/2013 |

OTHER PUBLICATIONS

Belcher et al, "A Selective Feature Information Approach for Iris Image-Quality Measure", Sep. 2008, IEEE, vol. 3, No. 3, p. 572-577.*

He et al, "A fast iris image quality evaluation method based on weighted entropy", Sep. 2007, SPIE, vol. 6623, pp. 1-8.*

B. Galvin, et al., Recovering Motion Fields: An Evaluation of Eight Optical Flow Algorithms, Proc. of the British Machine Vision Conf. (1998).

International Search Report on PCT/US2012/025468 dated Sep. 14, 2012.

J. R. Bergen, et al., Hierarchical Model-Based Motion Estimation, European Conf. on Computer Vision (1993).

K. Nishino, et al., The World in an Eye, IEEE Conf. on Pattern Recognition, vol. 1, at pp. 444-451 (Jun. 2004).

Notice of Allowance on U.S. Appl. No. 12/658,706 dated Feb. 24, 2012.

Office Action on U.S. Appl. No. 12/675,189 dated Dec. 7, 2012.

R. Kumar, et al., Direct recovery of shape from multiple views: a parallax based approach, 12th IAPR Int'l Conf. on Pattern Recognition, Oct. 1994.

R. P. Wildes, Iris Recognition: An Emerging Biometric Technology, Proc. IEEE 85(9) at pp. 1348-1363 (Sep. 1997).

Written Opinion on PCT/US2012/025468 dated Sep. 14, 2012.

B Galvin, et al., Recovering Motion Fields: An Evaluation of Eight Optical Flow Algorithms, Proc. of the British Machine Vision Conf. (1998).

Final Office Action, mailed Jan. 29, 2014, in U.S. Appl. No. 13/807,256.

John Daugman, "How Iris Recognition Works," IEEE Transaction on Circuits and Systems for Video Technology, vol. 14, No. 1, pp. 21-30 (Jan. 2004).

International Application No. PCT/US2008/074737: International Preliminary Report on Patentability mailed Mar. 2, 2010.

International Application No. PCT/US2008/074737: Written Opinion mailed Jan. 23, 2009.

International Application No. PCT/US2008/074737: International Search Report dated Jan. 23, 2009.

(56) References Cited

OTHER PUBLICATIONS

International Application No. PCT/US2012/032391: International Preliminary Report on Patentability mailed Oct. 8, 2013.
International Application No. PCT/US2012/032391: Written Opinion mailed Jul. 25, 2013.
International Application No. PCT/US2012/032391: International Search Report dated Jul. 25, 2013.
International Application No. PCT/US2012/025468: International Preliminary Report on Patentability mailed Aug. 21, 2013.
International Application No. PCT/US2008/074751: International Preliminary Report on Patentability mailed Mar. 2, 2010.
International Application No. PCT/US2008/074751: Written Opinion mailed Jan. 28, 2009.
International Application No. PCT/US2008/074751: International Search Report mailed Jan. 28, 2009.
Office Action in U.S. Appl. No. 13/440,707 dated Jan. 14, 2014.
Office Action in U.S. Appl. No. 13/773,168 dated Oct. 8, 2013.
Office Action in U.S. Appl. No. 13/493,455 mailed Apr. 9, 2014.
Office Action in U.S. Appl. No. 13/493,455 mailed Sep. 19, 2013.
He, Xiaofu et al., "Contactless Autofeedback Iris Capture Design", IEEE Transactions on Instrumentation and Measurement, IEEE Service Center, Piscataway, NJ, U.S. 57(7):1369-1375 (2008).
Lu, Huiqi et al., "Iris Recognition on Low Computational Power Mobile Devices", 23 pages, (2011). Retrieved from the Internet: URL:http:jjcdn.intechopen.comjpdfs-wm/14646.pdf [retrieved on Jul. 23, 2014].
Peters, Tanya H. et al., "Effects of segmentation routine and acquisition environment on is recognition", 97 pages, (2009). Retrieved from the Internet: URL:http://etd.nd.edu/ETD-db/thesesjavailablejetd-12112009-103348/ [retrieved on Jul. 21, 2014].
Office Action in U.S. Appl. No. 13/493,462, mailed Jul. 1, 2014, 11 pages.
Office Action in U.S. Appl. No. 13/773,168, mailed Jul. 16, 2014, 19 pages.
Notice of Allowance in U.S. Appl. No. 13/493,455, mailed Jul. 18, 2014, 5 pages.
Extended European Search Report in EP Application No. EP 12866256.6, dated Aug. 1, 2014, 7 pages.
Office Action in U.S. Appl. No. 13/786,079, mailed Sep. 26, 2014, 8 pages.
Office Action in U.S. Appl. No. 13/440,707, mailed Sep. 30, 2014, 22 pages.

\* cited by examiner

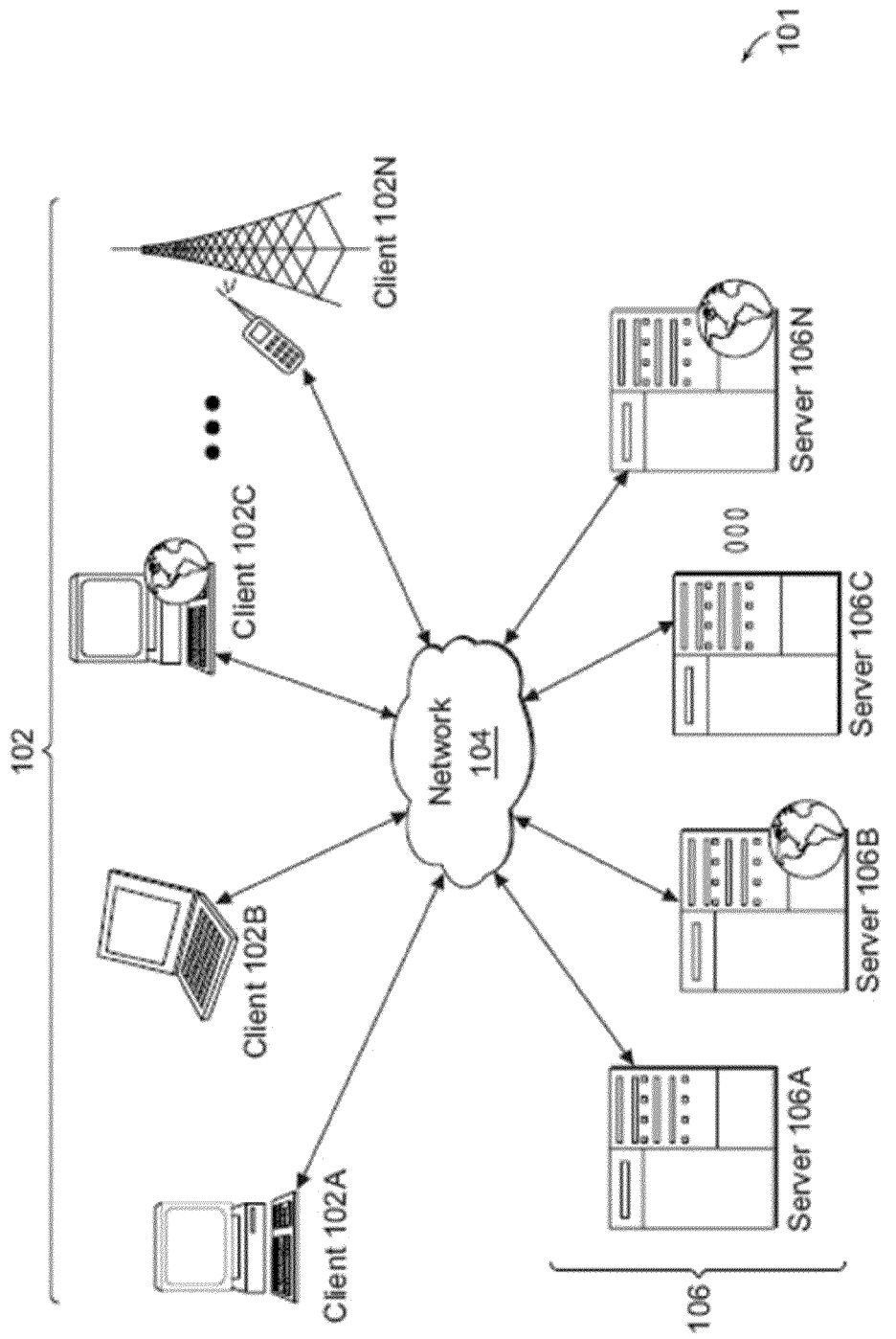

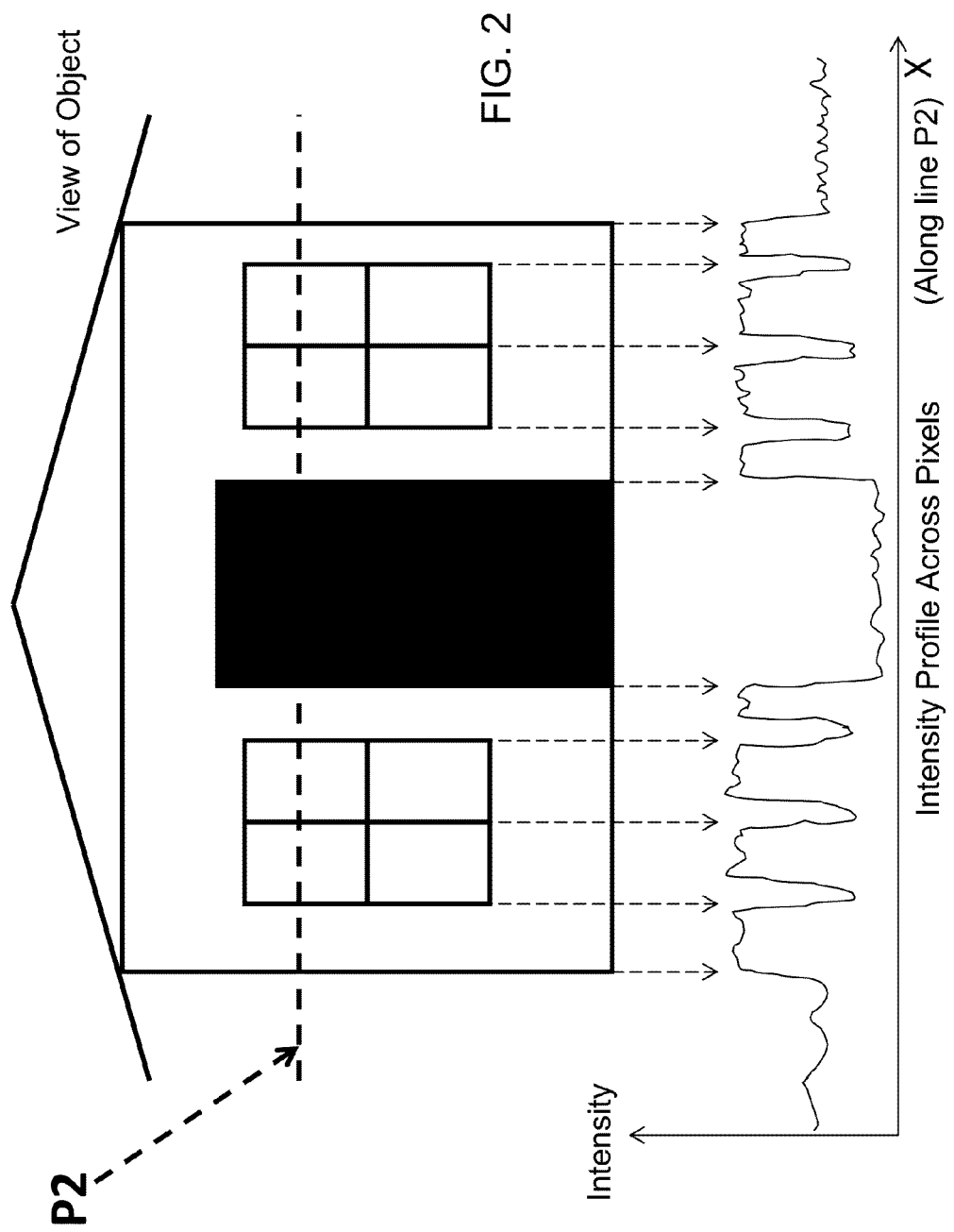

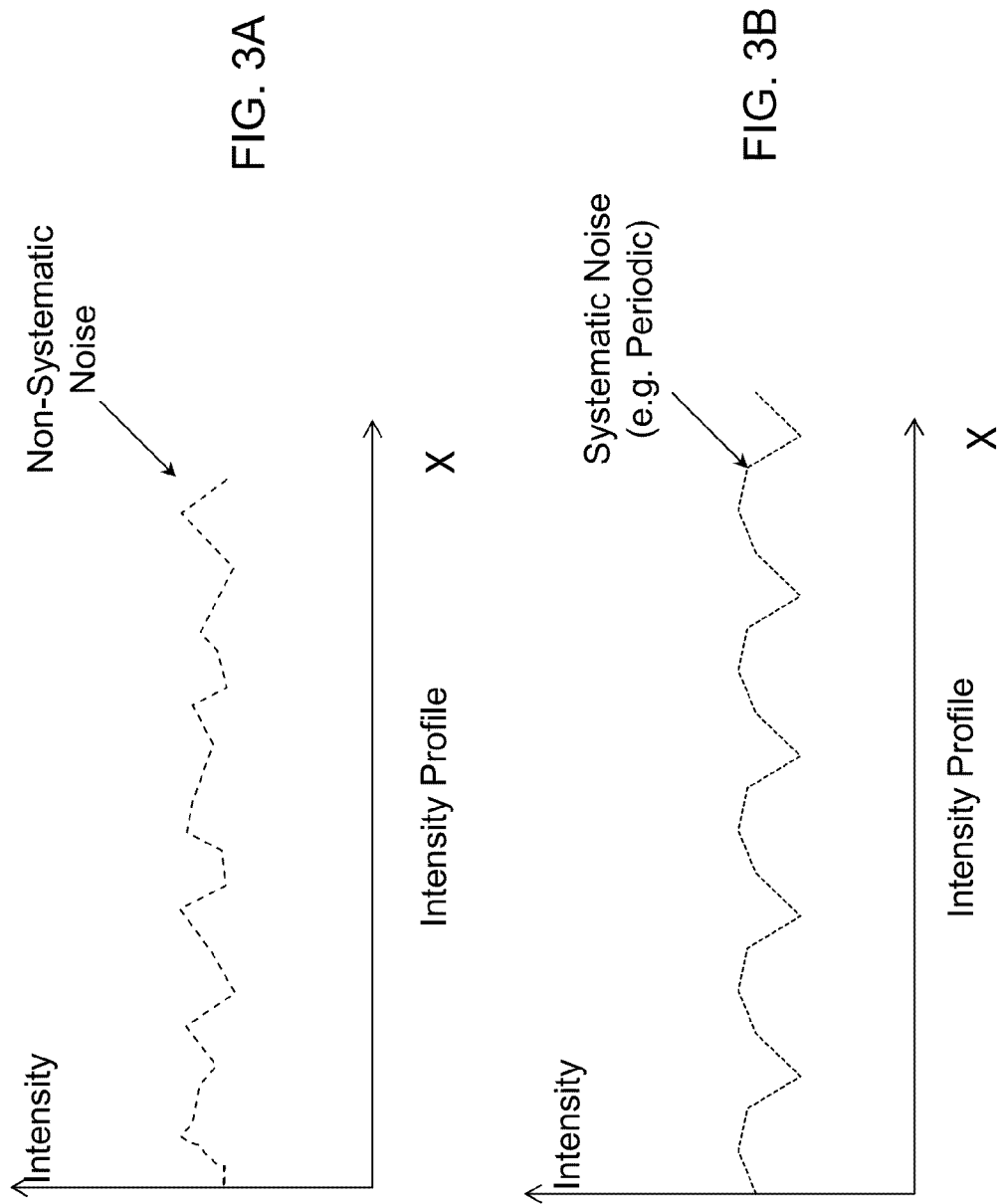

Superposition of Intensity Profiles (Noise and Iris Texture)

| case | Physical Implementation | Noise characterization | Iris Texture characterization | Iris Recognition FALSE REJECT Performance | Iris Recognition FALSE MATCH Performance | Visible Image Performance |
|---|---|---|---|---|---|---|
| 1 | Ideal theoretical | No noise | Low or High Amplitude | Excellent : Low false reject rate | Excellent : Low false match rate | Excellent: No noise |
| 2 | Sensor in picture-taking mode | Minimal noise | Minimal Amplitude | Unacceptable: False reject rate much higher compared to case 1 | Acceptable if random zero-mean noise dominates remaining noise, Unacceptable if systematic noise dominates remaining noise | Excellent: Minimal Noise |
| 3 | Sensor in iris recognition mode | Random Zero-mean noise | High Amplitude | Acceptable : False reject rate higher compared to case 1 | Excellent : Low false match rate | Unacceptable: Image Noise |
| 4 | Sensor in iris recognition mode | Random Zero-mean noise | Low Amplitude | Unacceptable : Much higher false reject rate compared to case 1 | Excellent : Low false match rate | Unacceptable: Image Noise |
| 5 | Sensor in iris recognition mode | Systematic Noise | High Amplitude | Acceptable : False reject rate higher compared to case 1 | Acceptable : Higher false match rate compared to case 1 | Unacceptable: Image Noise |
| 6 | Sensor in iris recognition mode | Systematic Noise | Low Amplitude | Unacceptable: False reject rate much higher compared to case 1 | Unacceptable : Higher false match rate compared to case 1 | Unacceptable: Image Noise |

FIG. 12

| | Configuration | One or Two-Eye Capture | Iris Diameter | Dominant Eye Uncertainty |
|---|---|---|---|---|
| 1 | | 2 | Small | No |
| 2 | | 2 | Small | No |
| 3 | | 2 | Small | Yes |
| 4 | | 1 | Small | Yes |
| 5 | | 1 | Large | No |

FIG. 32

Camera centering with Dominant Right Eye

Camera centering with Dominant Left Eye

MOBILE IDENTITY PLATFORM

RELATED APPLICATION

The present application is a continuation of and claims priority to U.S. patent application Ser. No. 13/440,707, entitled "Mobile Identity Platform", filed Apr. 5, 2012, which itself
  claims the benefit of and priority to U.S. Provisional Patent Application No. 61/472,270, entitled "Mobile Identity Platform", filed Apr. 6, 2011, and claims the benefit of and priority to Provisional Patent Application No. 61/472,279, entitled "Efficient Method and System for the Acquisition of Face and Iris Imagery", filed Apr. 6, 2011, and
is a continuation-in-part of and claims priority to U.S. patent application Ser. No. 13/398,562, entitled "Efficient Method and System for the Acquisition of Scene Imagery and Iris Imagery using a Single Sensor", filed Feb. 16, 2012, which itself
  claims the benefit of and priority to U.S. Provisional Patent Application No. 61/443,757, entitled "Method and System for Iris Recognition and Face Acquisition", filed Feb. 17, 2011, and
is a continuation-in-part of and claims priority to U.S. patent application Ser. No. 12/675,189, entitled "System and Method for Iris Data Acquisition for Biometric Identification", filed Feb. 25, 2010, which itself
  is a National Stage Entry of PCT Application Number PCT/US08/74737, entitled "System and Method for Iris Data Acquisition for Biometric Identification", filed Aug. 29, 2008, which itself
    claims priority to U.S. Provisional Patent Application No. 60/969,607, entitled "Methodology for Acquiring Biometric Data Large Volumes", filed Sep. 1, 2007,
all of which are incorporated herein by reference in their entireties for all purposes.

FIELD OF THE DISCLOSURE

The present invention relates to image processing and identity verification technologies, and more specifically to systems and methods directed to a mobile platform for biometric acquisition and processing.

BACKGROUND

Typical systems for acquiring iris images for biometric matching are not optimized for compactness. Many different form factors of biometric systems exist. For iris biometric, such devices are typically hand-held, desk-top or of a fixed installation. One of the problems with hand-held iris biometric devices is that they are bulky and they have been designed only for an operator to carry as a special purpose piece of bulky equipment. Desk-top devices are easy to remove and steal, and fixed installations limit the mobility of where the biometric authentication can be performed.

In addition, Biometric systems are typically designed to acquire optimal images by considering specific constraints of the type of biometric in question. If other data is to be acquired (e.g. face or background imagery), then typically different sensors are used since requirements for different types of imagery are very different. However, such an approach can add cost to the overall solution and may also increase the size or footprint of the system. In addition, the number of components required for image acquisition and processing (e.g., illuminators, sensors, positioning systems, storage for images, etc) create complexity in the design of an integrated device that is both mobile and compact. Moreover, the ability to acquire high quality biometric images in a compact device for efficient processing provides further challenges.

SUMMARY

Certain aspects of the design of an embedded iris image acquisition device can optimize performance. These may include a means for positioning the user in the camera field of view; a means for ensuring that the illumination is pointed optimally at the user; a means for enabling the acquisition of both high-quality and visible and infra-red images using the same sensor; a means for pointing the embedded device at the face of the user without having to pick up the device; an optimal configuration of components that maximizes the likelihood of acquiring high quality imagery when the user holds the device; a means to acquire successively higher-quality images of the iris in order to reduce memory requirements which are limited on a small embedded device, while at the same time ensuring that poorer quality images are matched when the accuracy requirements of the application permits it; a means to use successively higher-quality images acquired, to perform matching on limited numbers of images on the device; a means to use the successively higher-quality acquired images to perform successive matching on limited numbers of images on the device while at the same time encrypting the results; and a means to use the successively higher-quality acquired images in order to send a reduced number of images over a network or other connection, encrypted or un-encrypted, in order to reduce bandwidth across the connection.

In one aspect, the present systems and methods are directed to a compact, mobile apparatus for iris image acquisition. The apparatus may be adapted to address effects of ocular dominance in the subject and to guide positioning of the subject's iris for the image acquisition. The apparatus may include a sensor for acquiring an iris image from a subject. A compact mirror may be oriented relative to a dominant eye of the subject. The mirror may be sized to present an image of a single iris to the subject when the apparatus is positioned at a suitable distance for image acquisition. The mirror may assist the subject in positioning the iris for iris image acquisition. The mirror may be positioned between the sensor and the iris during iris image acquisition. The mirror may transmit a portion of light reflected off the iris to the sensor.

In some embodiments, the apparatus includes a connector for connecting to a computing device. The connector may extend from a lower end of the apparatus below the grasp of the subject's hand when operating the apparatus. In certain embodiments, the apparatus includes an articulated connector for connecting the apparatus to a computing device. The articulated connector may adjustably maintain a position of the apparatus for iris image acquisition. In some embodiments, the apparatus includes an infra-red illuminator integrated with a display screen of the apparatus. In certain embodiments, the apparatus includes a second mirror to present an image of a second iris to the subject when positioned at the suitable distance for image acquisition. In certain embodiments, the apparatus includes a contact region or button for a thumb or finger of the subject to initiate image acquisition while holding the apparatus.

In some embodiments, the mirror is located near one end of a body of the apparatus, the subject holding at least a portion of the other end while operating the apparatus. The mirror may include an adjustable or rotatable mount for tilting the mirror with respect to the dominant eye of the subject. In some embodiments, the apparatus includes at least one illuminator may provide at least one of: infra-red illumination and visible illumination to illuminate a feature of the subject. The illuminator may be oriented to focus illumination primarily on the iris. In certain embodiments, the sensor is used to acquire an infra-red image of the iris and a non-infra-red image of a feature of the subject. The apparatus may include a filter array for filtering light to the sensor. The filter array may include a plurality of infra-red cut regions and a plurality of infra-red pass regions.

The sensor may acquire a plurality of images within a period of time. The apparatus may include an image processing module for selecting an iris image from the plurality of images. The selected iris image may be of better quality for biometric matching than at least some of the other images in the plurality of images. The image processing module may store the selected iris image in a buffer while acquiring or processing additional images. In some embodiments, the image processing module overwrites a previously-selected image stored in a buffer with the selected iris image. The image processing module may perform biometric matching on the selected iris image. The image processing module may send the selected iris image to a computer via a physical or wireless connection. In certain embodiments, the apparatus includes a display having an image of a portion of the subject's face. The display may move an image of the subject's eye towards a physical location of the sensor to guide the subject's gaze towards the sensor.

In another aspect, the present systems and methods are directed to a compact, mobile apparatus for iris image acquisition. The apparatus may be adapted to address effects of ocular dominance in the subject and to guide positioning of the subject's iris for the image acquisition. The apparatus may include a sensor. The apparatus may include a display for displaying an image of a portion of the subject's face. The display may move or shift an image of the subject's eye towards a physical location of the sensor to draw the subject's gaze towards the sensor. The sensor may acquire an image of the subject's iris for biometric matching when the subject's gaze is drawn to or near the sensor.

In yet another aspect, the present systems and methods are directed to a compact, mobile apparatus for iris image acquisition. The apparatus may include a sensor for acquiring a plurality of images of a subject over a period of time. The apparatus may include an image processing module for selecting an image of the subject's iris from the plurality of acquired images for further processing. The selected image may be of better quality for biometric matching than at least some of the other images in the plurality of acquired images.

In some embodiments, the image processing module selects the iris image based at least in part on a predetermined image quality threshold. The image processing module may store the selected iris image in a buffer while acquiring or processing additional images. The image processing module may overwrite a previously-selected image stored in a buffer with the selected iris image. The image processing module may perform biometric matching on the selected iris image. In certain embodiments, the image processing module encrypts the selected iris image. The image processing module may send the selected iris image to a computer via a physical or wireless connection.

In still another aspect, the present systems and methods are directed to a compact apparatus for iris image acquisition. The apparatus may include a sensor for acquiring an infra-red image of a subject's iris and a non-infra-red image of a feature of the subject. The apparatus may include a filter array for selectively filtering light to the sensor. The filter array may include a plurality of infra-red cut regions for sampling non-infra-red data for the non-infra-red image. The filter array may include a plurality of infra-red pass regions for sampling infra-red data for the infra-red image. The plurality of infra-red pass regions may sample infra-red data substantially at or below a corresponding Nyquist limit for the infra-red pass regions. In some embodiments, the plurality of infra-red pass regions sample infra-red data substantially at or below a corresponding Nyquist limit for the infra-red pass regions, by de-focusing the light being filtered.

In some embodiments, the plurality of infra-red cut regions samples visible data substantially at or below a corresponding Nyquist limit for the infra-red cut regions. The apparatus may include a look-up table or calculator for determining pixels of the sensor exposed to infra-red light passing through the filter array. In certain embodiments, the apparatus may include an interpolator for interpolating the sampled infra-red data to produce the infra-red image. The apparatus may include an interpolator for interpolating the sampled non-infra-red data to produce the non-infra-red image.

BRIEF DESCRIPTION OF THE DRAWINGS

The following figures depict certain illustrative embodiments of the methods and systems described herein, where like reference numerals refer to like elements. Each depicted embodiment is illustrative of these methods and systems and not limiting.

FIG. 1A is a block diagram illustrative of an embodiment of a networked environment with a client machine that communicates with a server;

FIG. 2 depicts an embodiment of an image intensity profile corresponding to a portion of an image;

FIG. 3A depicts an image intensity profile of one embodiment of non-systematic noise;

FIG. 3B depicts an image intensity profile of one embodiment of systematic noise;

FIG. 12 depicts a chart showing the effect of noise on acquired images;

FIG. 32 depicts embodiments of sensor and mirror configuration;

DETAILED DESCRIPTION

Figure 1B:
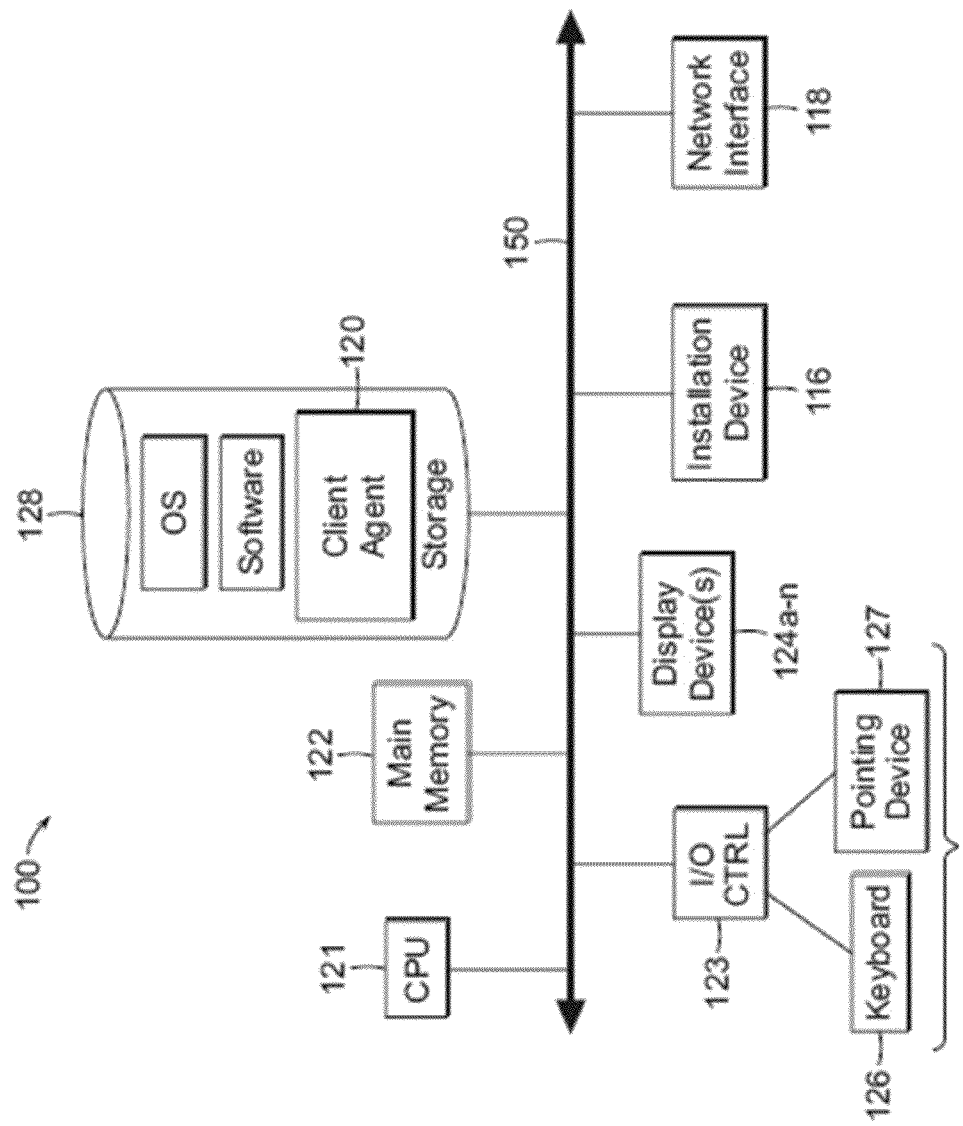
FIGS. 1B and 1C are block diagrams illustrative of embodiments of computing machines for practicing the methods and systems described herein.

Before addressing other aspects of the mobile identity platform, a description of system components and features suitable for use in the present systems and methods may be helpful. FIG. 1A illustrates one embodiment of a computing environment 101 that includes one or more client machines 102A-102N (generally referred to herein as "client machine(s) 102") in communication with one or more servers 106A-106N (generally referred to herein as "server(s) 106"). Installed in between the client machine(s) 102 and server(s) 106 is a network.

In one embodiment, the computing environment 101 can include an appliance installed between the server(s) 106 and client machine(s) 102. This appliance can mange client/server connections, and in some cases can load balance client connections amongst a plurality of backend servers. The client machine(s) 102 can in some embodiment be referred to as a single client machine 102 or a single group of client machines 102, while server(s) 106 may be referred to as a single server 106 or a single group of servers 106. In one embodiment a single client machine 102 communicates with more than one server 106, while in another embodiment a single server 106 communicates with more than one client machine 102. In yet another embodiment, a single client machine 102 communicates with a single server 106.

A client machine 102 can, in some embodiments, be referenced by any one of the following terms: client machine(s) 102; client(s); client computer(s); client device(s); client computing device(s); local machine; remote machine; client node(s); endpoint(s); endpoint node(s); or a second machine. The server 106, in some embodiments, may be referenced by any one of the following terms: server(s), local machine; remote machine; server farm(s), host computing device(s), or a first machine(s).

The client machine 102 can in some embodiments execute, operate or otherwise provide an application that can be any one of the following: software; a program; executable instructions; a virtual machine; a hypervisor; a web browser; a web-based client; a client-server application; a thin-client computing client; an ActiveX control; a Java applet; software related to voice over internet protocol (VoIP) communications like a soft IP telephone; an application for streaming video and/or audio; an application for facilitating real-time-data communications; a HTTP client; a FTP client; an Oscar client; a Telnet client; or any other set of executable instructions. Still other embodiments include a client device 102 that displays application output generated by an application remotely executing on a server 106 or other remotely located machine. In these embodiments, the client device 102 can display the application output in an application window, a browser, or other output window. In one embodiment, the application is a desktop, while in other embodiments the application is an application that generates a desktop.

The computing environment 101 can include more than one server 106A-106N such that the servers 106A-106N are logically grouped together into a server farm 106. The server farm 106 can include servers 106 that are geographically dispersed and logically grouped together in a server farm 106, or servers 106 that are located proximate to each other and logically grouped together in a server farm 106. Geographically dispersed servers 106A-106N within a server farm 106 can, in some embodiments, communicate using a WAN, MAN, or LAN, where different geographic regions can be characterized as: different continents; different regions of a continent; different countries; different states; different cities; different campuses; different rooms; or any combination of the preceding geographical locations. In some embodiments the server farm 106 may be administered as a single entity, while in other embodiments the server farm 106 can include multiple server farms 106.

In some embodiments, a server farm 106 can include servers 106 that execute a substantially similar type of operating system platform (e.g., WINDOWS NT, manufactured by Microsoft Corp. of Redmond, Wash., UNIX, LINUX, or SNOW LEOPARD.) In other embodiments, the server farm 106 can include a first group of servers 106 that execute a first type of operating system platform, and a second group of servers 106 that execute a second type of operating system platform. The server farm 106, in other embodiments, can include servers 106 that execute different types of operating system platforms.

The server 106, in some embodiments, can be any server type. In other embodiments, the server 106 can be any of the following server types: a file server; an application server; a web server; a proxy server; an appliance; a network appliance; a gateway; an application gateway; a gateway server; a virtualization server; a deployment server; a SSL VPN server; a firewall; a web server; an application server or as a master application server; a server 106 executing an active directory; or a server 106 executing an application acceleration program that provides firewall functionality, application functionality, or load balancing functionality. In some embodiments, a server 106 may be a RADIUS server that includes a remote authentication dial-in user service. Some embodiments include a first server 106A that receives requests from a client machine 102, forwards the request to a second server 106B, and responds to the request generated by the client machine 102 with a response from the second server 106B. The first server 106A can acquire an enumeration of applications available to the client machine 102 and well as address information associated with an application server 106 hosting an application identified within the enumeration of applications. The first server 106A can then present a response to the client's request using a web interface, and communicate directly with the client 102 to provide the client 102 with access to an identified application.

Client machines 102 can, in some embodiments, be a client node that seeks access to resources provided by a server 106. In other embodiments, the server 106 may provide clients 102 or client nodes with access to hosted resources. The server 106, in some embodiments, functions as a master node such that it communicates with one or more clients 102 or servers 106. In some embodiments, the master node can identify and provide address information associated with a server 106 hosting a requested application, to one or more clients 102 or servers 106. In still other embodiments, the master node can be a server farm 106, a client 102, a cluster of client nodes 102, or an appliance.

One or more clients 102 and/or one or more servers 106 can transmit data over a network 104 installed between machines and appliances within the computing environment 101. The network 104 can comprise one or more sub-networks, and can be installed between any combination of the clients 102, servers 106, computing machines and appliances included within the computing environment 101. In some embodiments, the network 104 can be: a local-area network (LAN); a metropolitan area network (MAN); a wide area network (WAN); a primary network 104 comprised of multiple sub-networks 104 located between the client machines 102 and the servers 106; a primary public network 104 with a private sub-network 104; a primary private network 104 with a public sub-network 104; or a primary private network 104 with a private sub-network 104. Still further embodiments include a network 104 that can be any of the following network types: a point to point network; a broadcast network; a telecommunications network; a data communication network; a computer network; an ATM (Asynchronous Transfer Mode) network; a SONET (Synchronous Optical Network) network; a SDH (Synchronous Digital Hierarchy) network; a wireless network; a wireline network; or a network 104 that includes a wireless link where the wireless link can be an infrared channel or satellite band. The network topology of the network 104 can differ within different embodiments, possible network topologies include: a bus network topology; a star network topology; a ring network topology; a repeater-based network topology; or a tiered-star network topology. Additional embodiments may include a network 104 of mobile telephone networks that use a protocol to communicate among mobile devices, where the protocol can be any one of the following: AMPS; TDMA; CDMA; GSM; GPRS UMTS; 3G; 4G; or any other protocol able to transmit data among mobile devices.

Illustrated in FIG. 1B is an embodiment of a computing device 100, where the client machine 102 and server 106 illustrated in FIG. 1A can be deployed as and/or executed on any embodiment of the computing device 100 illustrated and described herein. Included within the computing device 100 is a system bus 150 that communicates with the following components: a central processing unit 121; a main memory 122; storage memory 128; an input/output (I/O) controller 123; display devices 124A-124N; an installation device 116; and a network interface 118. In one embodiment, the storage memory 128 includes: an operating system, software routines, and a client agent 120. The I/O controller 123, in some embodiments, is further connected to a key board 126, and a pointing device 127. Other embodiments may include an I/O controller 123 connected to more than one input/output device 130A-130N.

Figure 1C:
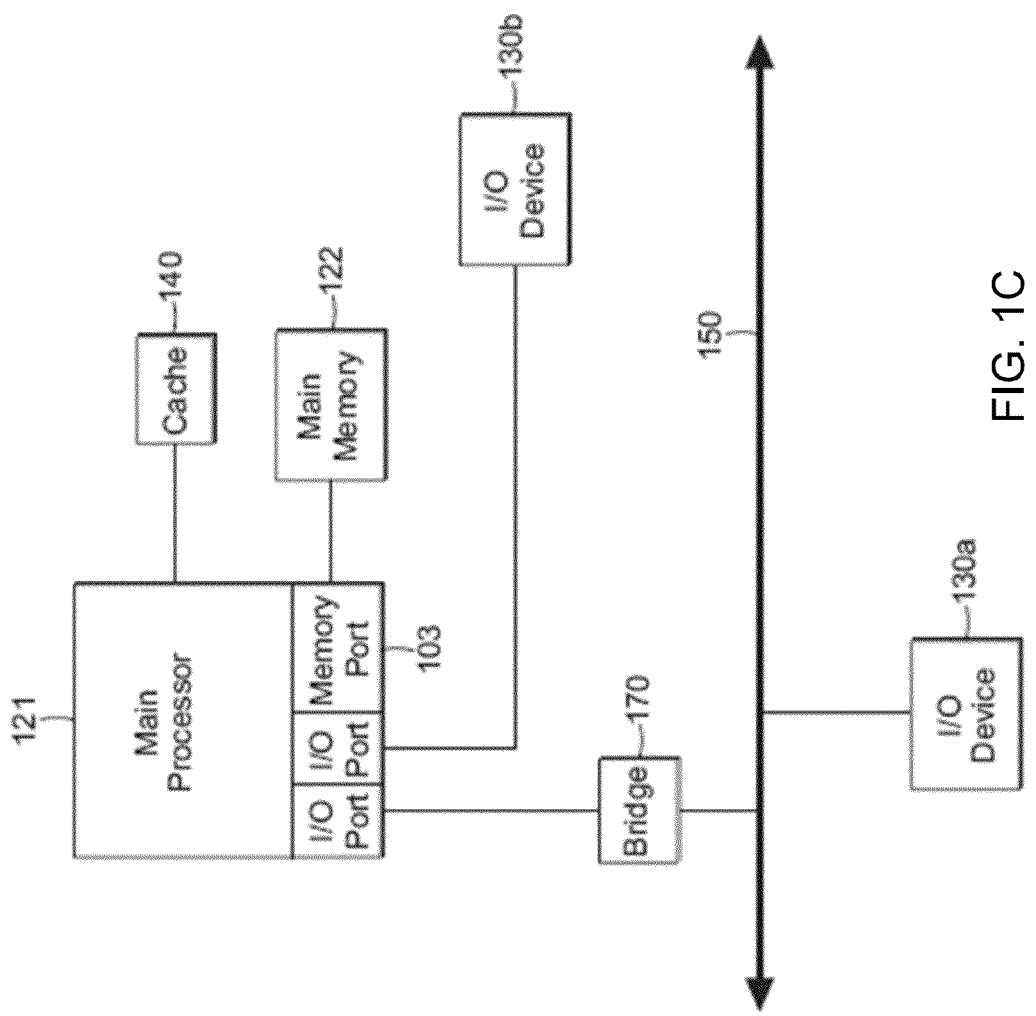

FIG. 1C illustrates one embodiment of a computing device 100, where the client machine 102 and server 106 illustrated in FIG. 1A can be deployed as and/or executed on any embodiment of the computing device 100 illustrated and described herein. Included within the computing device 100 is a system bus 150 that communicates with the following components: a bridge 170, and a first I/O device 130A. In another embodiment, the bridge 170 is in further communication with the main central processing unit 121, where the central processing unit 121 can further communicate with a second I/O device 130B, a main memory 122, and a cache memory 140. Included within the central processing unit 121, are I/O ports, a memory port 103, and a main processor.

Embodiments of the computing machine 100 can include a central processing unit 121 characterized by any one of the following component configurations: logic circuits that respond to and process instructions fetched from the main memory unit 122; a microprocessor unit, such as: those manufactured by Intel Corporation; those manufactured by Motorola Corporation; those manufactured by Transmeta Corporation of Santa Clara, Calif.; the RS/6000 processor such as those manufactured by International Business Machines; a processor such as those manufactured by Advanced Micro Devices; or any other combination of logic circuits. Still other embodiments of the central processing unit 122 may include any combination of the following: a microprocessor, a microcontroller, a central processing unit with a single processing core, a central processing unit with two processing cores, or a central processing unit with more than one processing core.

While FIG. 1C illustrates a computing device 100 that includes a single central processing unit 121, in some embodiments the computing device 100 can include one or more processing units 121. In these embodiments, the computing device 100 may store and execute firmware or other executable instructions that, when executed, direct the one or more processing units 121 to simultaneously execute instructions or to simultaneously execute instructions on a single piece of data. In other embodiments, the computing device 100 may store and execute firmware or other executable instructions that, when executed, direct the one or more processing units to each execute a section of a group of instructions. For example, each processing unit 121 may be instructed to execute a portion of a program or a particular module within a program.

In some embodiments, the processing unit 121 can include one or more processing cores. For example, the processing unit 121 may have two cores, four cores, eight cores, etc. In one embodiment, the processing unit 121 may comprise one or more parallel processing cores. The processing cores of the processing unit 121 may in some embodiments access available memory as a global address space, or in other embodiments, memory within the computing device 100 can be segmented and assigned to a particular core within the processing unit 121. In one embodiment, the one or more processing cores or processors in the computing device 100 can each access local memory. In still another embodiment, memory within the computing device 100 can be shared amongst one or more processors or processing cores, while other memory can be accessed by particular processors or subsets of processors. In embodiments where the computing device 100 includes more than one processing unit, the multiple processing units can be included in a single integrated circuit (IC). These multiple processors, in some embodiments, can be linked together by an internal high speed bus, which may be referred to as an element interconnect bus.

In embodiments where the computing device 100 includes one or more processing units 121, or a processing unit 121 including one or more processing cores, the processors can execute a single instruction simultaneously on multiple pieces of data (SIMD), or in other embodiments can execute multiple instructions simultaneously on multiple pieces of data (MIMD). In some embodiments, the computing device 100 can include any number of SIMD and MIMD processors.

The computing device 100, in some embodiments, can include an image processor, a graphics processor or a graphics processing unit. The graphics processing unit can include any combination of software and hardware, and can further input graphics data and graphics instructions, render a graphic from the inputted data and instructions, and output the rendered graphic. In some embodiments, the graphics processing unit can be included within the processing unit 121. In other embodiments, the computing device 100 can include one or more processing units 121, where at least one processing unit 121 is dedicated to processing and rendering graphics.

One embodiment of the computing machine 100 includes a central processing unit 121 that communicates with cache memory 140 via a secondary bus also known as a backside bus, while another embodiment of the computing machine 100 includes a central processing unit 121 that communicates with cache memory via the system bus 150. The local system bus 150 can, in some embodiments, also be used by the central processing unit to communicate with more than one type of I/O device 130A-130N. In some embodiments, the local system bus 150 can be any one of the following types of buses: a VESA VL bus; an ISA bus; an EISA bus; a Micro-Channel Architecture (MCA) bus; a PCI bus; a PCI-X bus; a PCI-Express bus; or a NuBus. Other embodiments of the computing machine 100 include an I/O device 130A-130N that is a video display 124 that communicates with the central processing unit 121. Still other versions of the computing machine 100 include a processor 121 connected to an I/O device 130A-130N via any one of the following connections: HyperTransport, Rapid I/O, or InfiniBand. Further embodiments of the computing machine 100 include a processor 121 that communicates with one I/O device 130A using a local interconnect bus and a second I/O device 130B using a direct connection.

The computing device 100, in some embodiments, includes a main memory unit 122 and cache memory 140. The cache memory 140 can be any memory type, and in some embodiments can be any one of the following types of memory: SRAM; BSRAM; or EDRAM. Other embodiments include cache memory 140 and a main memory unit 122 that can be any one of the following types of memory: Static random access memory (SRAM), Burst SRAM or Synch-Burst SRAM (BSRAM); Dynamic random access memory (DRAM); Fast Page Mode DRAM (FPM DRAM); Enhanced DRAM (EDRAM), Extended Data Output RAM (EDO RAM); Extended Data Output DRAM (EDO DRAM); Burst Extended Data Output DRAM (BEDO DRAM); Enhanced DRAM (EDRAM); synchronous DRAM (SDRAM); JEDEC SRAM; PC100 SDRAM; Double Data Rate SDRAM (DDR SDRAM); Enhanced SDRAM (ESDRAM); SyncLink DRAM (SLDRAM); Direct Rambus DRAM (DRDRAM); Ferroelectric RAM (FRAM); or any other type of memory. Further embodiments include a central processing unit 121 that can access the main memory 122 via: a system bus 150; a memory port 103; or any other connection, bus or port that allows the processor 121 to access memory 122.

One embodiment of the computing device 100 provides support for any one of the following installation devices 116: a CD-ROM drive, a CD-R/RW drive, a DVD-ROM drive, tape drives of various formats, USB device, a bootable medium, a bootable CD, a bootable CD for GNU/Linux distribution such as KNOPPIX®, a hard-drive or any other device suitable for installing applications or software. Applications can in some embodiments include a client agent 120, or any portion of a client agent 120. The computing device 100 may further include a storage device 128 that can be either one or more hard disk drives, or one or more redundant arrays of independent disks; where the storage device is configured to store an operating system, software, programs applications, or at least a portion of the client agent 120. A further embodiment of the computing device 100 includes an installation device 116 that is used as the storage device 128.

The computing device 100 may further include a network interface 118 to interface to a Local Area Network (LAN), Wide Area Network (WAN) or the Internet through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can also be established using a variety of communication protocols (e.g., TCP/IP, IPX, SPX, NetBIOS, Ethernet, ARCNET, SONET, SDH, Fiber Distributed Data Interface (FDDI), RS232, RS485, IEEE 802.11, IEEE 802.11a, IEEE 802.11b, IEEE 802.11g, CDMA, GSM, WiMax and direct asynchronous connections). One version of the computing device 100 includes a network interface 118 able to communicate with additional computing devices 100' via any type and/or form of gateway or tunneling protocol such as Secure Socket Layer (SSL) or Transport Layer Security (TLS), or the Citrix Gateway Protocol manufactured by Citrix Systems, Inc. Versions of the network interface 118 can comprise any one of: a built-in network adapter; a network interface card; a PCMCIA network card; a card bus network adapter; a wireless network adapter; a USB network adapter; a modem; or any other device suitable for interfacing the computing device 100 to a network capable of communicating and performing the methods and systems described herein.

Embodiments of the computing device 100 include any one of the following I/O devices 130A-130N: a keyboard 126; a pointing device 127; mice; trackpads; an optical pen; trackballs; microphones; drawing tablets; video displays; speakers; inkjet printers; laser printers; and dye-sublimation printers; or any other input/output device able to perform the methods and systems described herein. An I/O controller 123 may in some embodiments connect to multiple I/O devices 103A-130N to control the one or more I/O devices. Some embodiments of the I/O devices 130A-130N may be configured to provide storage or an installation medium 116, while others may provide a universal serial bus (USB) interface for receiving USB storage devices such as the USB Flash Drive line of devices manufactured by Twintech Industry, Inc. Still other embodiments include an I/O device 130 that may be a bridge between the system bus 150 and an external communication bus, such as: a USB bus; an Apple Desktop Bus; an RS-232 serial connection; a SCSI bus; a FireWire bus; a FireWire 800 bus; an Ethernet bus; an AppleTalk bus; a Gigabit Ethernet bus; an Asynchronous Transfer Mode bus; a HIPPI bus; a Super HIPPI bus; a SerialPlus bus; a SCI/LAMP bus; a FibreChannel bus; or a Serial Attached small computer system interface bus.

In some embodiments, the computing machine 100 can execute any operating system, while in other embodiments the computing machine 100 can execute any of the following operating systems: versions of the MICROSOFT WINDOWS operating systems; the different releases of the Unix and Linux operating systems; any version of the MAC OS manufactured by Apple Computer; OS/2, manufactured by International Business Machines; Android by Google; any embedded operating system; any real-time operating system; any open source operating system; any proprietary operating system; any operating systems for mobile computing devices; or any other operating system. In still another embodiment, the computing machine 100 can execute multiple operating systems. For example, the computing machine 100 can execute PARALLELS or another virtualization platform that can execute or manage a virtual machine executing a first operating system, while the computing machine 100 executes a second operating system different from the first operating system.

The computing machine 100 can be embodied in any one of the following computing devices: a computing workstation; a desktop computer; a laptop or notebook computer; a server; a handheld computer; a mobile telephone; a portable telecommunication device; a media playing device; a gaming system; a mobile computing device; a netbook, a tablet; a device of the IPOD or IPAD family of devices manufactured by Apple Computer; any one of the PLAYSTATION family of devices manufactured by the Sony Corporation; any one of the Nintendo family of devices manufactured by Nintendo Co; any one of the XBOX family of devices manufactured by the Microsoft Corporation; or any other type and/or form of computing, telecommunications or media device that is capable of communication and that has sufficient processor power and memory capacity to perform the methods and systems described herein. In other embodiments the computing machine 100 can be a mobile device such as any one of the following mobile devices: a JAVA-enabled cellular telephone or personal digital assistant (PDA); any computing device that has different processors, operating systems, and input devices consistent with the device; or any other mobile computing device capable of performing the methods and systems described herein. In still other embodiments, the computing device 100 can be any one of the following mobile computing devices: any one series of Blackberry, or other handheld device manufactured by Research In Motion Limited; the iPhone manufactured by Apple Computer; Palm Pre; a Pocket PC; a Pocket PC Phone; an Android phone; or any other handheld mobile device. Having described certain system components and features that may be suitable for use in the present systems and methods, further aspects are addressed below.

FIG. 2 depicts an illustrative image of a typical scene or object (e.g., house), acquired by a typical image sensor. An image sensor may include, for example, a digital charge-coupled device (CCD) or complementary metal-oxide-semiconductor (CMOS) active pixel sensor, although not limited to these. The graph or intensity profile corresponding to the image shows, for a cross sectional region indicated by line P2, the intensity value I of pixels on the vertical axis and the corresponding spatial position X. Bright and dark points in the intensity profile correspond to bright and dark points in the image as shown. Typically, there may be substantial noise in the signal, represented by fluctuations in intensity even within uniformly illuminated areas (e.g., regions corresponding to the door of the house). Noise may be derived from several sources, for example amplifier noise and shot-noise, anisotropic (systematic) noise, and sporadic noise. Shot noise relates to the quantum effect of having a finite number of photons being collected in a particular pixel-well in a finite period of time. The smaller the pixel size, the larger the shot noise may result. This is because there may be fewer photons from which to infer a measurement of incident illumination. As pixel dimensions get smaller, the focal length of associated optics for a given image resolution may also drop linearly. This may reduce the thickness of the lens/sensor component combination. However, as requirements for sensor resolution increase, and as space constraints for sensors and their associated optics become tighter, sensor and image pixel sizes have to be correspondingly reduced to accommodate the requirements and constraints. A result of the reduction in pixel size is a substantial increase in noise in the sensor. This type of noise, as well as amplifier noise, may be characterized as being time-varying, and non-systematic as depicted in FIG. 3A.

Figure 4:
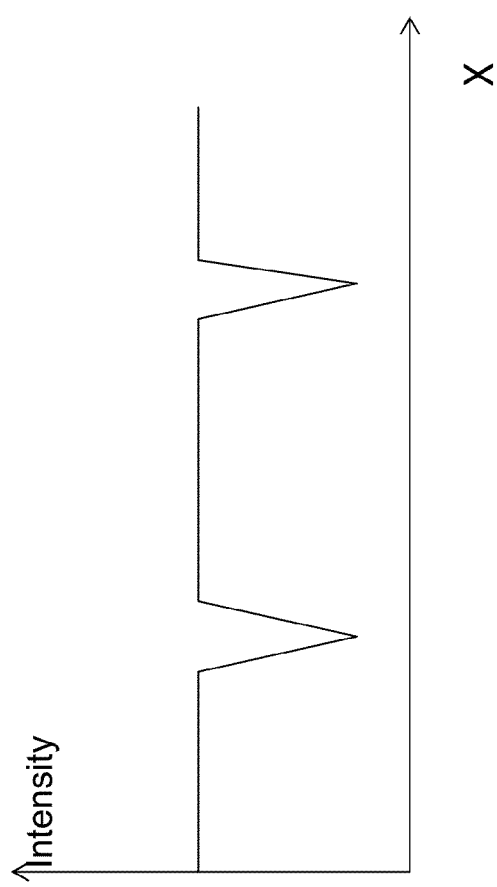
FIG. 4 depicts an image intensity profile of one embodiment of sporadic noise.

Another type of noise is anisotropic, or systematic/periodic noise. Periodic noise can be caused, for example, by differences in amplifier gains in the read-out path of the image sensor. For example, different rows and columns may pass through different amplifiers with slightly different gains. This type of systematic noise is depicted in FIG. 3B, where an intensity profile that should be uniformly flat is in fact fluctuating periodically in one dimension (e.g., across an image). FIG. 4 depicts an example of sporadic noise introduced into an image, which may be evident across multiple images. For example, occasional pixels in an array of sensor nodes may have degraded sensitivity, is non-functional or have limited or excessive gain, resulting in pixels that are brighter or darker as shown.

Figure 5:
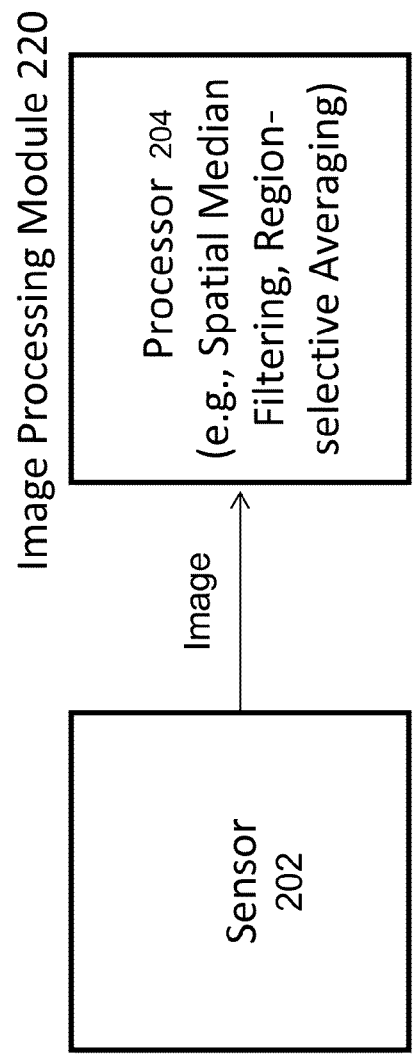
FIG. 5 depicts one embodiment of a system for performing noise reduction.
Figure 6:
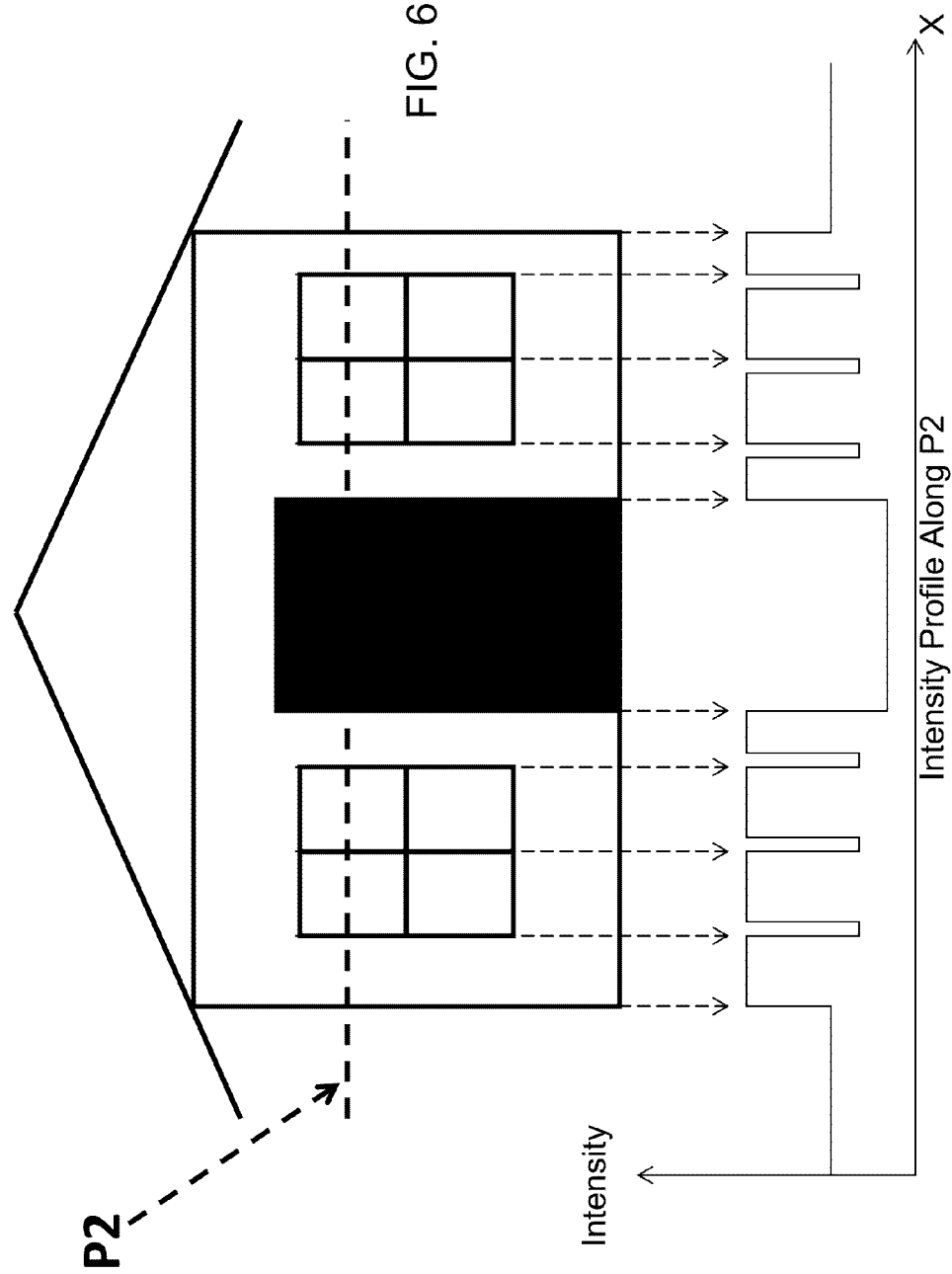
FIG. 6 depicts an embodiment of an image intensity profile corresponding to a portion of an image that have undergone noise reduction.

Problems arising from noise are typically addressed by performing noise reduction in an image processing module 220. The image processing module 220 may employ any type of spatial median filtering or region-selective averaging, as depicted in FIG. 5. There are many methods for performing noise reduction, and we identify median filtering and region-selective averaging merely for illustration. FIG. 6 depicts an intensity profile which may result from noise reduction. Although noise reduction may have essentially removed the noise, the image processing module 220 maintained features (e.g. bright and dark points) corresponding to actual objects and edges in the scene. From a user's perspective, the image quality is typically unacceptable in FIG. 1 (e.g., noisy), whereas that in FIG. 6 is considered of better quality.

Figure 7:
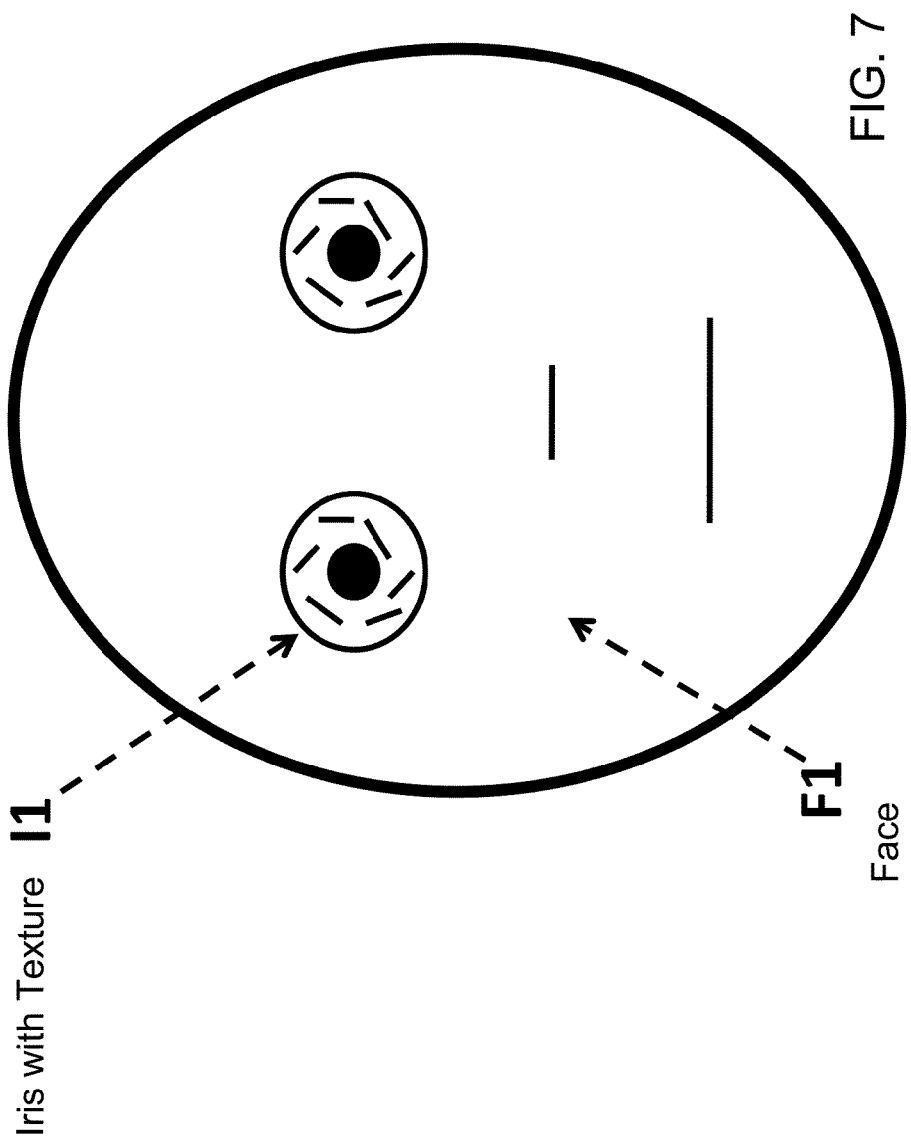
FIG. 7 is a diagram of an embodiment of an image of a view of a face including iris texture.
Figure 8:
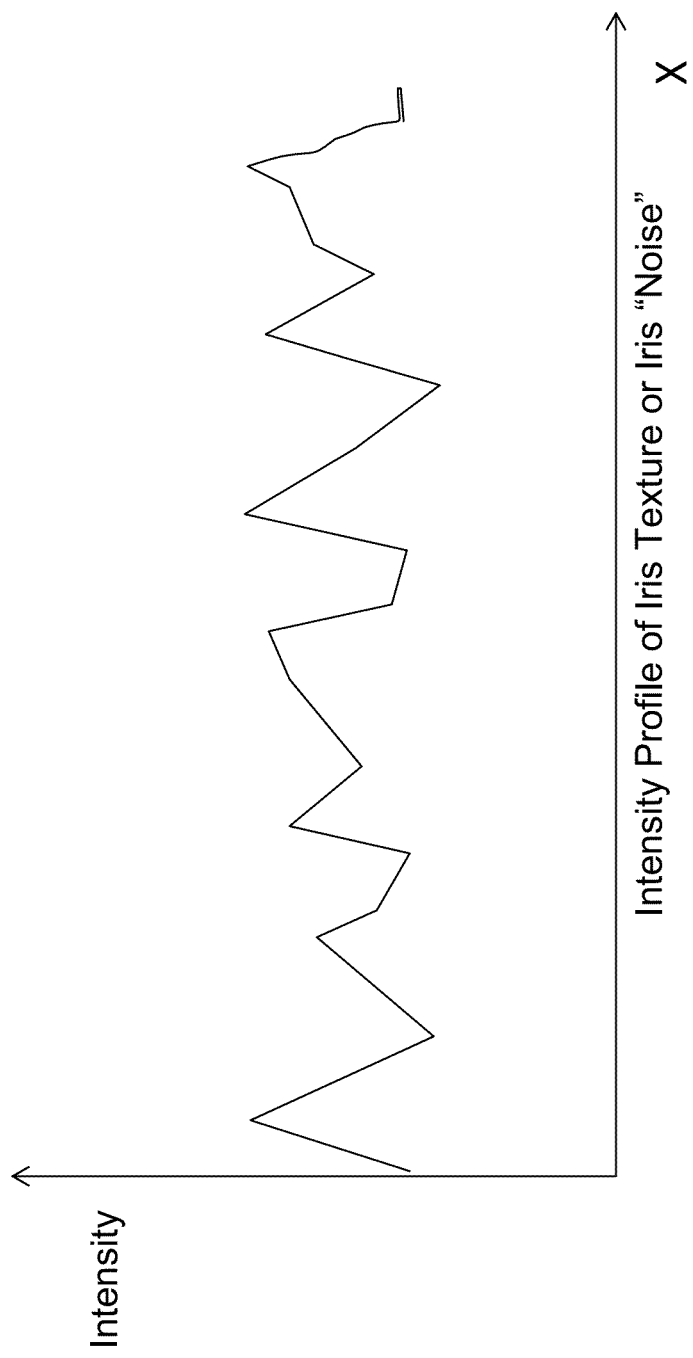
FIG. 8 depicts one embodiment of an image intensity profile representing iris texture.

FIG. 7 depicts an image of an iris I1 and a face F1. The image may be acquired using an optimal iris image acquisition system, for example, according to specifications described in the National Institute of Standards and Technology (NIST) standards. These specifications may include that described in ANSI/INCITS 379-2004, Iris Image Interchange Format. Referring to FIG. 7, the texture of the iris is represented by the lines inside the circular region indicated by I1. FIG. 8 depicts one representation of the intensity profile of the iris' texture. In some embodiments, the similarity between FIG. 8 (intensity profile of iris texture pattern) and FIG. 2 (intensity profile of noise signal) can be quite apparent. A reason for such similarity is that the source of each signal/pattern is characterized by a random process. In the case of the iris, the signal is created by the tearing of iris tissue before birth, much like the process by which a paper tear is different each time it occurs. In the case of sensor noise, shot noise and other noises are created by random time-varying physical processes.

Frequency characteristics of the iris signal "texture" has been characterized to some degree in NIST standards [ANSI/INCITS 379-2004, Iris Image Interchange Format], for example, the minimum resolution values corresponding to line/pairs per millimeter (mm) may be designated for different iris diameter ranges. The iris diameter may be dependent on a particular optical configuration. By way of illustration, for an iris diameter between 100-149 pixels, the defined pixel resolution may be a minimum of 8.3 pixels per mm, with an optical resolution at 60% modulation of a minimum of 2.0 line-pairs per mm. For an iris diameter between 150-199 pixels, the defined pixel resolution may be a minimum of 12.5 pixels per mm with an optical resolution at 60% modulation of a minimum of 3.0 line-pairs per mm. For an iris diameter with 200 or more pixels, the defined pixel resolution may be a minimum of 16.7 pixels per mm, with an optical resolution at 60% modulation of a minimum of 4.0 line-pairs per mm. Other diameter, defined pixel resolution and/or optical resolution combinations may be suitable in certain embodiments.

Figure 9:
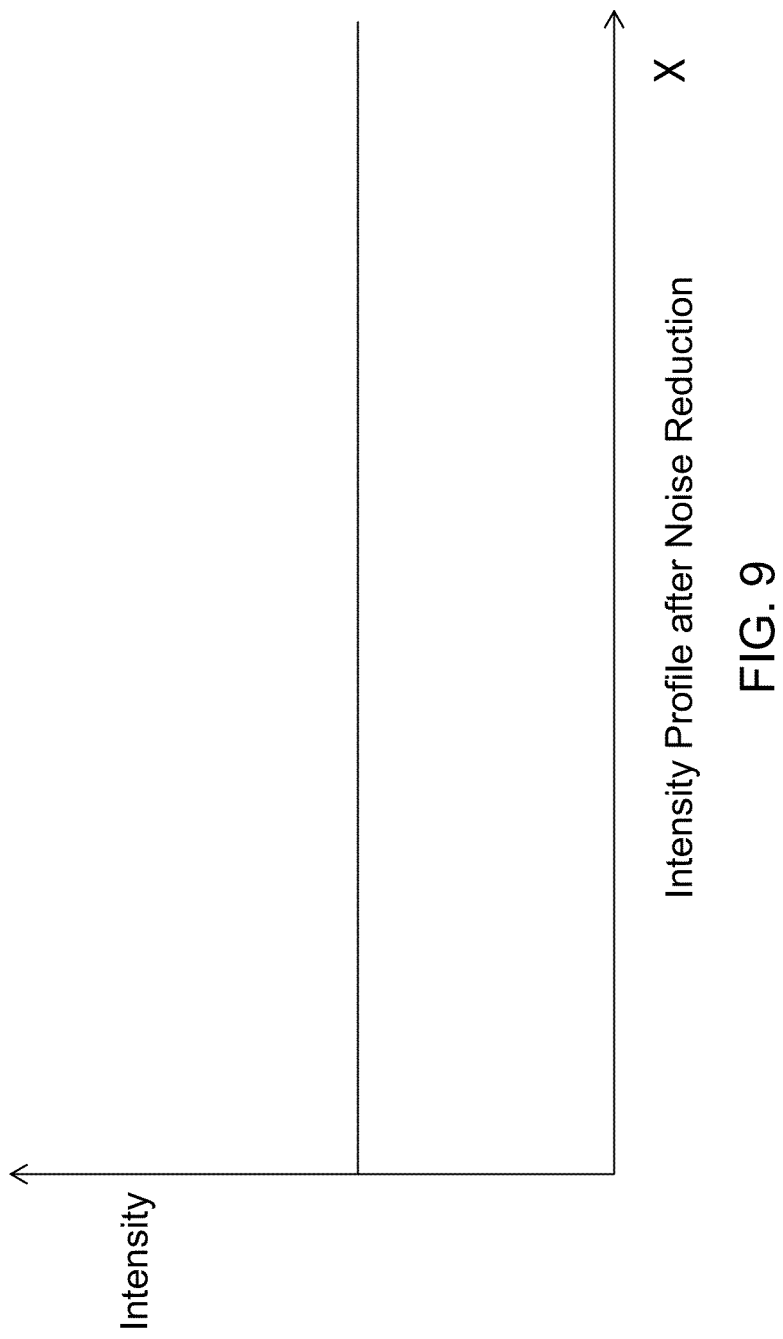
FIG. 9 depicts one embodiment of an image intensity profile representing iris texture after noise reduction.

FIG. 9 depicts an intensity profile of iris texture after undergoing some of the noise reduction processing described above. In this illustrative case, iris texture are essentially removed by the noise reduction. This is because the noise reduction algorithms, such as region-specific averaging, may be unable to differentiate between iris texture and noise. As such, noise reduction, which is standard or typical in most image-capturing devices, can be a limitation when adapted to perform iris recognition.

Figure 10:
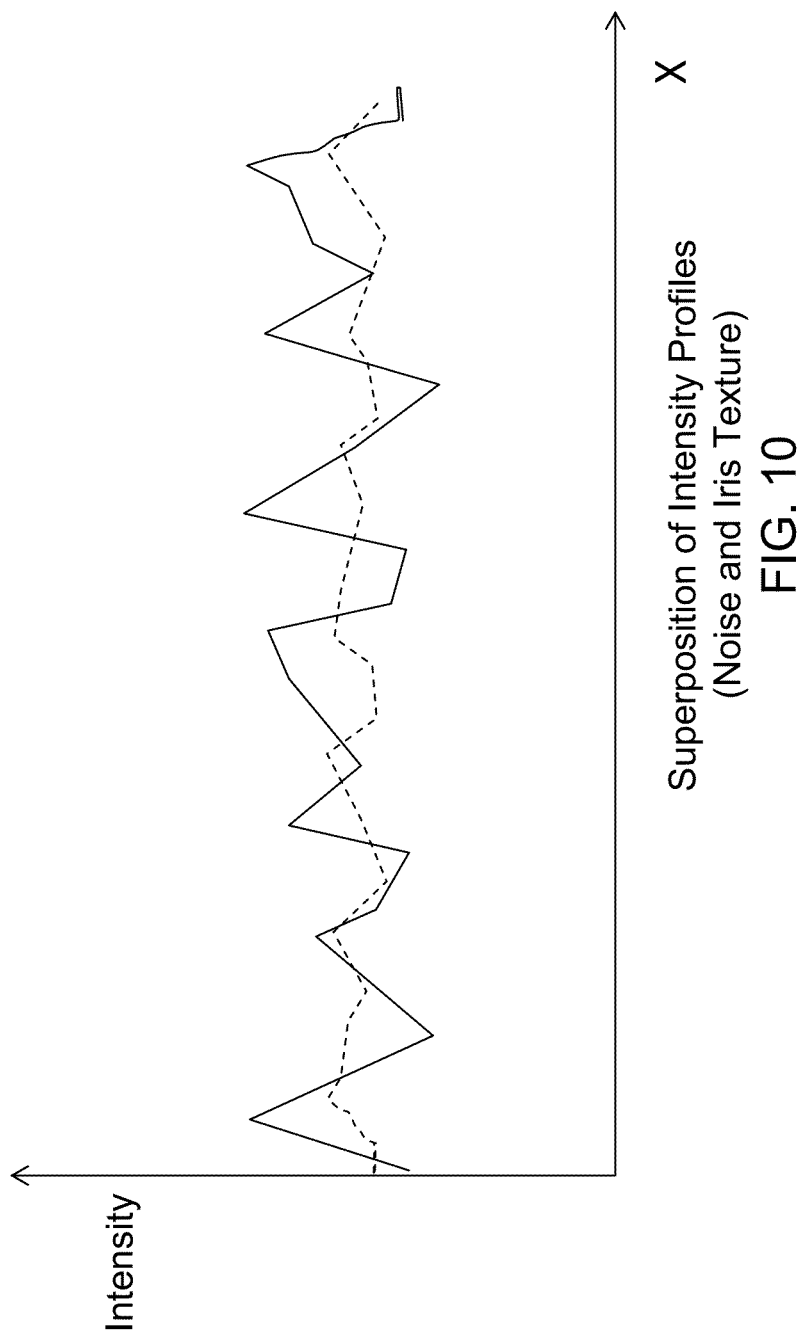
FIG. 10 depicts one embodiment of an image intensity profile representing iris texture and noise.

The present systems and methods can address this problem by recognizing particular characteristics related to iris recognition. FIG. 10 illustrates, in one embodiment, an intensity profile of iris texture acquired optimally (for example as in NIST standards [ANSI/INCITS 379-2004, Iris Image Interchange Format]), together with an intensity profile of sensor noise in dotted lines. Certain iris recognition processes involve identifying the lack of statistical independence between an enrolled signal and a probe signal. One significance may be that a match is typically declared by a comparison yielding a result that is unlikely to be achieved by a random process. As such, adding significant random and time-varying noise to a pristine iris signal may therefore: 1) not significantly increase the false match rate since false matches result from non-random matching, 2) may have limited impact on the false rejection rate for an individual if the texture of the iris signal generally or essentially exceeds that of the sensor noise (e.g., even if the images themselves appear noisy to an observer), and 3) may increase the false reject rate for the user (with limited other consequences) if the texture of the iris signal has a similar or lesser magnitude compared to the magnitude of the sensor noise.

Adding systematic noise, however, to the pristine iris signal, as shown in FIG. 3 for example, could trigger a false match because a comparison between two data sets could yield a result that would not have been achieved by a random process. As such, certain embodiments of the methods and systems may prefer (e.g., counter-intuitively) the presence of noise (e.g., even significant levels of noise) in a captured iris image, to improve performance in iris identification as compared to images having reduced noise levels (e.g., through noise reduction). In some embodiments, the present systems may reduce or eliminate the level of non-systematic noise reduction applied to an image when the image is meant for iris recognition. The resultant images may potentially appear extremely noisy to an observer as compared to a processed imagery (e.g., with noise reduction applied). However, the performance in iris recognition may be significantly improved if a noisy imagery is used instead for iris recognition. In some particular hardware implementations, noise reduction algorithms are enabled and hard-coded, and may not be turned off. Some embodiments of the present methods and systems allow control over noise reduction algorithms so as to avoid reducing noise in frequency bands expected for iris texture, as described elsewhere in the specification.

Figure 11:
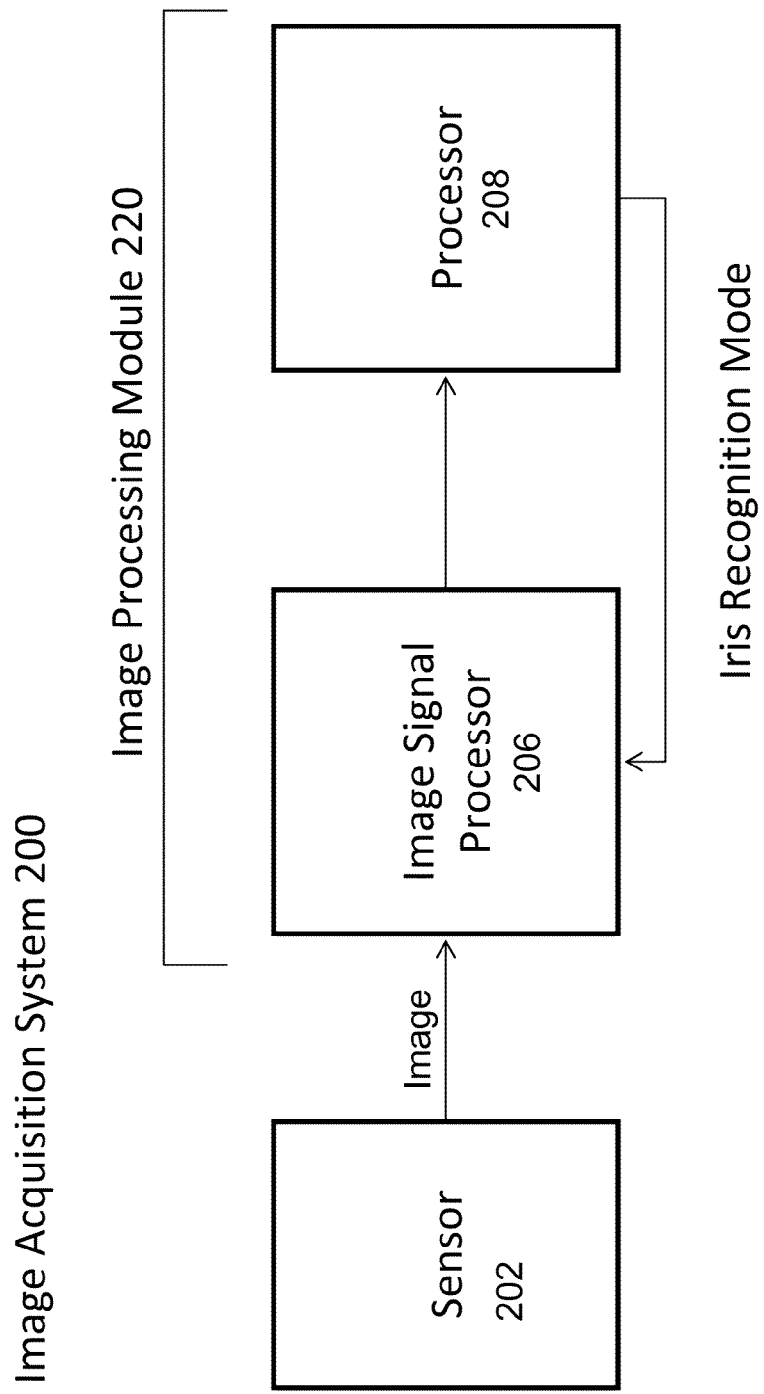
FIG. 11 depicts one embodiment of a system for acquisition of scene imagery and iris imagery using a single sensor.
Figure 13:
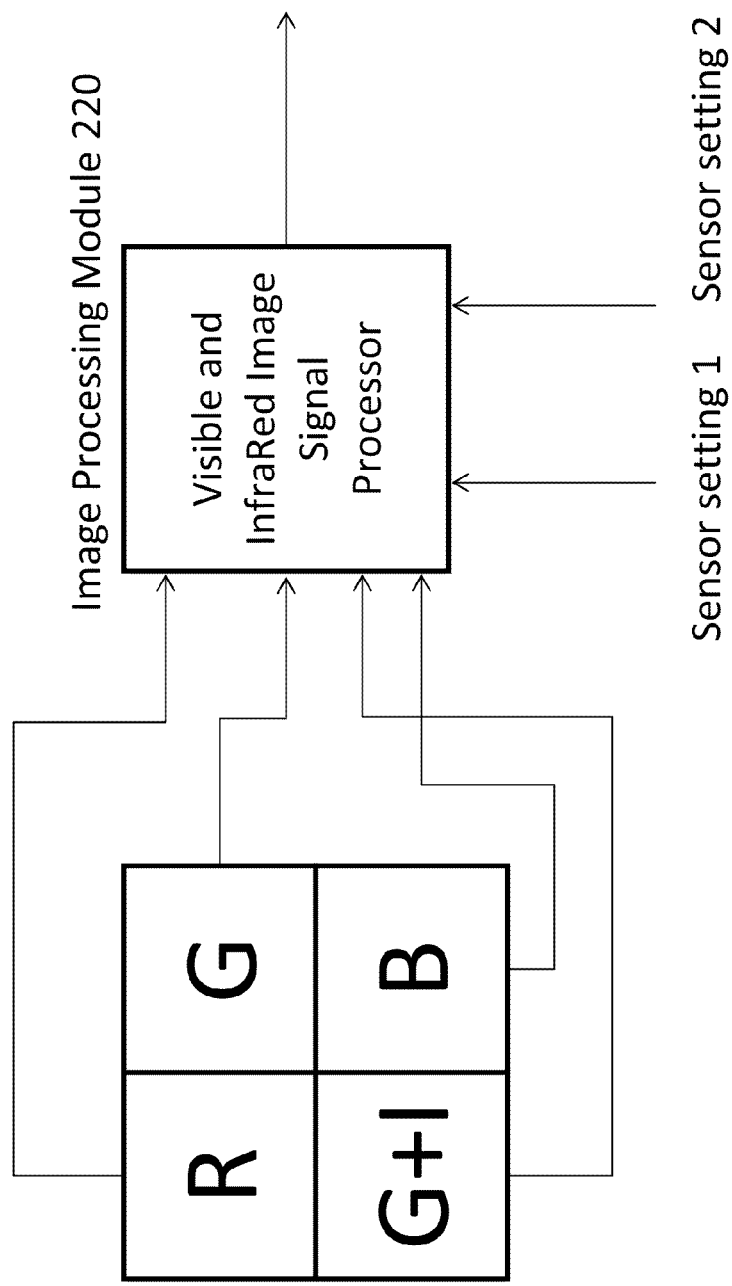
FIG. 13 depicts another embodiment of a system for acquisition of scene imagery and iris imagery using a single sensor.

FIG. 11 depicts an example implementation of an approach whereby a main processor may control an image signal processor, e.g., a low-level image signal processor. In a mode in which iris recognition is performed, a signal may transmitted to the image signal processor to modify the noise reduction process as described earlier. Depending on the magnitude of systematic noise, then such noise may be removed (e.g., using dynamic row calibration whereby pixels at an edge of the sensor are covered and can be used for sensor calibration) or can be left untouched if the magnitude of the noise is substantially smaller than the signal magnitude of iris texture. By way of illustration, FIG. 12 shows a table summarizing a number of scenarios, and describes how different types of noise may affect the performance of iris recognition and/or the quality of visible imagery, in different image acquisition modes.

Another challenge relating to acquiring optimal standard scene imagery and iris imagery on the same sensor relates to the wavelength of the illumination required for standard imagery and for iris imagery. Iris imagery typically requires infra-red illumination, while standard imagery typically requires visible illumination. There are sometimes conflicting constraints. Some embodiments of the present systems may be configured to address this by interleaving filters having different responses to infra-red and visible light. These systems may use one of a plurality of different configurations of such filters against an image sensor, when capturing an image. One example of a filter that may be incorporated or modified to produce an interleaved filter is one having a Bayer RGB (red, green, blue) filter pattern (see, e.g., U.S. Pat. No. 3,971,065). Filters that (primarily, significantly or only) pass infra-red may be interleaved with other filters that (primarily, significantly or only) passes colored or visible light. Some embodiments of filters that provide selected filtering are described in U.S. Pat. Pub. 20070145273, and U.S. Pat. Pub. 20070024931. Some embodiments of the present system and methods use a R,G,(G+I),B interleaved array instead. Some of these systems have the ability to maintain full (or substantially full) resolution of the G (green) signal to which the human visual system is typically most sensitive.

In iris recognition mode, the magnitude of the G (green) response is typically much less than that of the infra-red response due to incident infra-red illumination. In some embodiments, an estimate of the infra-red signal response (I) in iris recognition mode can be recovered by subtracting the (G) signal from the adjacent (G+I) signal. In standard image acquisition mode, the R,G,(G+I),B signal may be processed to recover an estimate G' of G in the pixel in which G+I was recovered. Various methods may be used for generating such estimates, such as when an R,G,T,B pixel array is used, where T is totally transparent. The T pixel in such an implementation may contain signals of the R,G,B and I signals accumulated or superimposed together. This can be problematic. If the T pixel filter is truly transparent, then for effective performance, the sum of the R,G,B,I responses must still lie within the dynamic range of the pixel. For a given integration time and pixel area throughout an entire imager, this means that the dynamic range of the R,G,B pixels cannot be fully utilized since saturation of the T pixel (R+G+B+I) could occur. Setting different pixel areas or gain for the T pixel compared to the other R,G,B pixels may be possible but may be expensive to implement. One improvement, which may be incorporated into the present systems, is to use a neutral density filter in place of the transparent filter. The neutral density filter may reduce the magnitude of the illumination of all wavelengths (R,G,B and I) at that pixel, and may allow a full or wide range of pixel capacities to be exploited in the R,G,B pixels, thereby reducing noise. A neutral density filter with value of 0.5 to 0.6 can be selected as an example. A green signal may typically contribute to approximately 60% of a luminance signal comprised of R,G and B combined together.

If a T filter is truly transparent, the overall dynamic range of the sensor will typically need to be reduced to accommodate the range of the T pixel and maintain it to be within a linear range, at the expense of the signal to noise ratio of the R,G,B pixels. By incorporating a R,G,G+I,B filter array in some embodiments of our systems, and since red and blue signals are not present in the G+I pixel, the overall dynamic range of the sensor may be increased compared to that of a R,G,T,B array, thereby increasing the signal to noise ratio.

Figure 14:
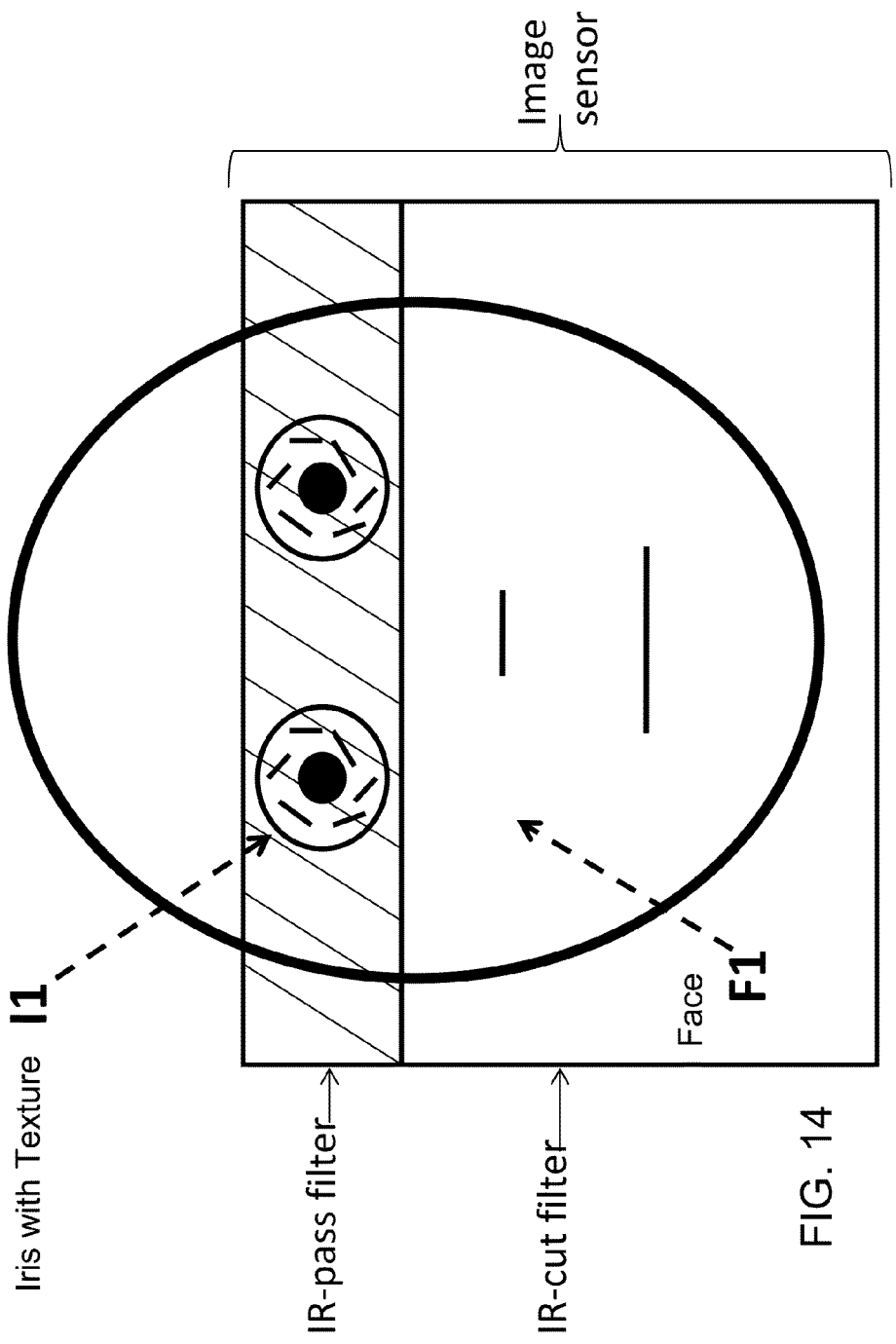
FIG. 14 depicts an embodiment of a system for acquisition of face imagery and iris imagery using a single sensor.

Another approach incorporated in some embodiments of our methods and systems for acquiring optimal standard scene imagery and iris imagery on the same sensor, relating to the wavelength of the illumination, involves multiplexing or positioning an infra-red cut filter over a standard image sensor or lens. In one embodiment, a portion of the sensor (for example, 20% of the sensor or sensor nodes) may be designated primarily for iris recognition, while the remaining (e.g., 80%) portion may be used for standard image acquisition, for example as shown in FIG. 14. A lower portion (e.g., 80%) of the sensor, as in this example, may be covered by a standard IR-cut filter. The remaining 20% of the sensor may remain uncovered. In iris recognition mode, the covered region may be ignored. For example, an iris recognition application executing on the image capturing device may guide the user to position their eyes within the sensing region of the uncovered 20% area. Feedback mechanisms can guide the user to move the image capturing device to locate the user's irises within an appropriate capture region. For example, since the face will be visible in the remaining 80% of the imager, this can be used for user guidance feedback, optionally with icons appearing in place of the eye region. In some embodiments, the image sensor may adjust its orientation to capture an image of the user's iris using the uncovered region.

Figure 15:
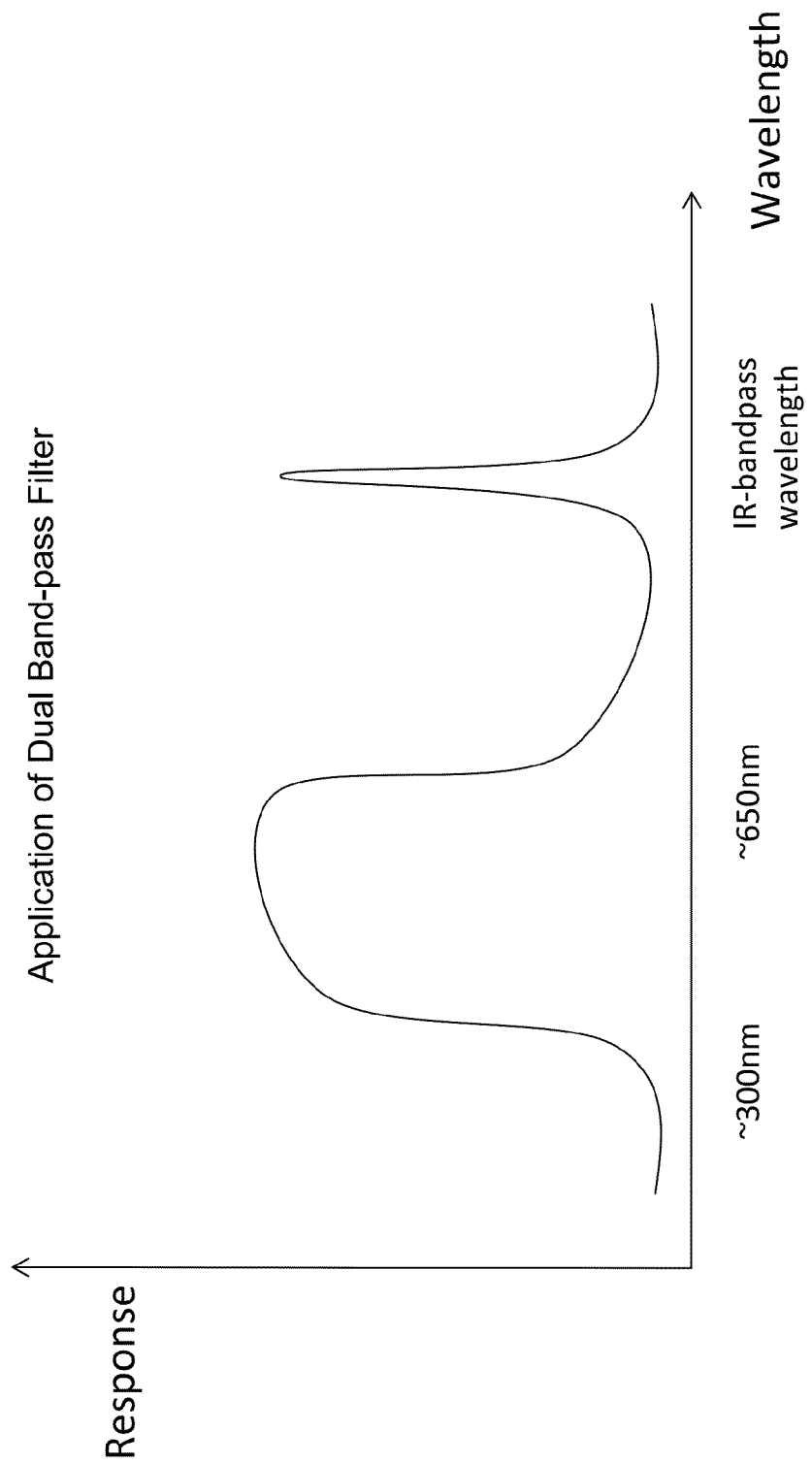
FIG. 15 depicts a response profile based on a dual band-pass filter.

Another approach incorporated within some embodiments of the present systems and methods uses a dual band-pass filter over the entire or a substantial portion of a color imager or sensor. Such a filter may pass both R,G,B signals and infra-red signals within select bands, such as bands around 850 nm or 940 nm, and may yield a frequency response as depicted in FIG. 15. In yet another embodiment, an image acquisition system may use an IR-cut filter that can be automatically or manually positioned or slid into place over at least a portion of an image sensor when the device is in standard image capture mode. For example, the IR-cut filter may cover a portion of the image sensor to be aligned with a user's eye for capturing iris imagery. The other portions of the image sensor may capture parts of a user's face, for example. Placement of the IR-cut filter may be at one end of the sensor, thereby allowing the sensor and the correspondingly-captured image to have two distinct regions (IR-cut and non-IR-cut) rather than 3 or more regions (e.g., non-IR-cut, IR-cut and non-IR-cut). This allows a larger and more contiguous non-iris portion of a scene (e.g., face) to be acquired, which may in turn be used for face identification for example. In some embodiments, a visible light filter or IR pass filter may be placed over the image sensor (e.g., optionally) when the device is in iris image capture mode.

Figure 16:
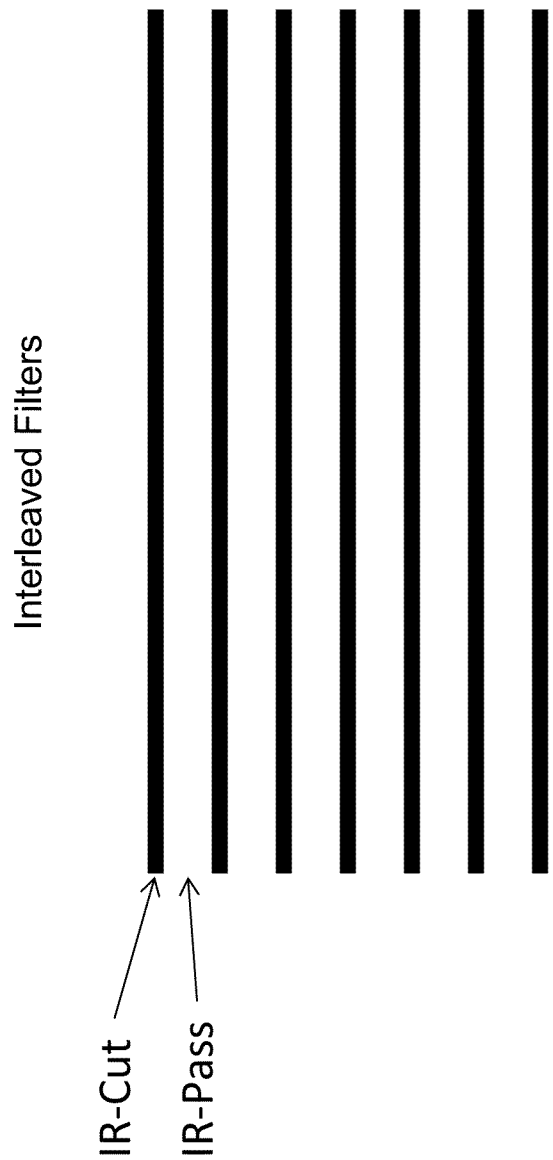
FIG. 16 depicts an embodiment of a configuration of interleaved filters.

In some embodiments, the image acquisition system may interleave infra-red cut and infra-red pass filters across the sensor, for example as shown in FIG. 16. An interleaved filter may be configured in various other ways, such as using a checker-box arrangement, stripes of various widths, or other alternating and/or repeatable patterns. In iris recognition mode, the response from sensor pixels/nodes underneath the IR-pass filter bands is used for iris recognition, while the response from sensor pixels/nodes underneath the IR-cut filter bands is used in standard image acquisition mode. In some embodiments, both standard and iris images may be acquired with a single image capture, for example, by separating IR and non-IR image components corresponding to the interleaving pattern.

Figure 17:
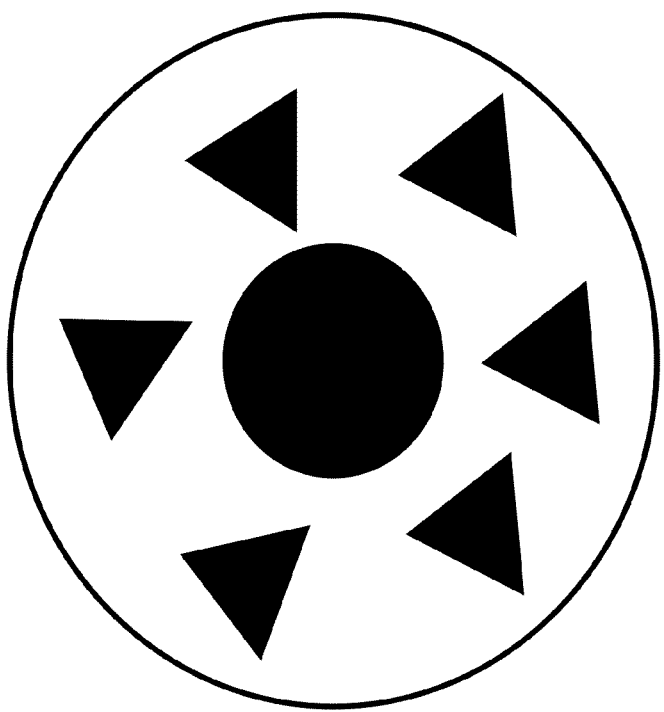
FIG. 17 depicts one embodiment of an image with artifacts reflected off an eye surface.
Figure 18:
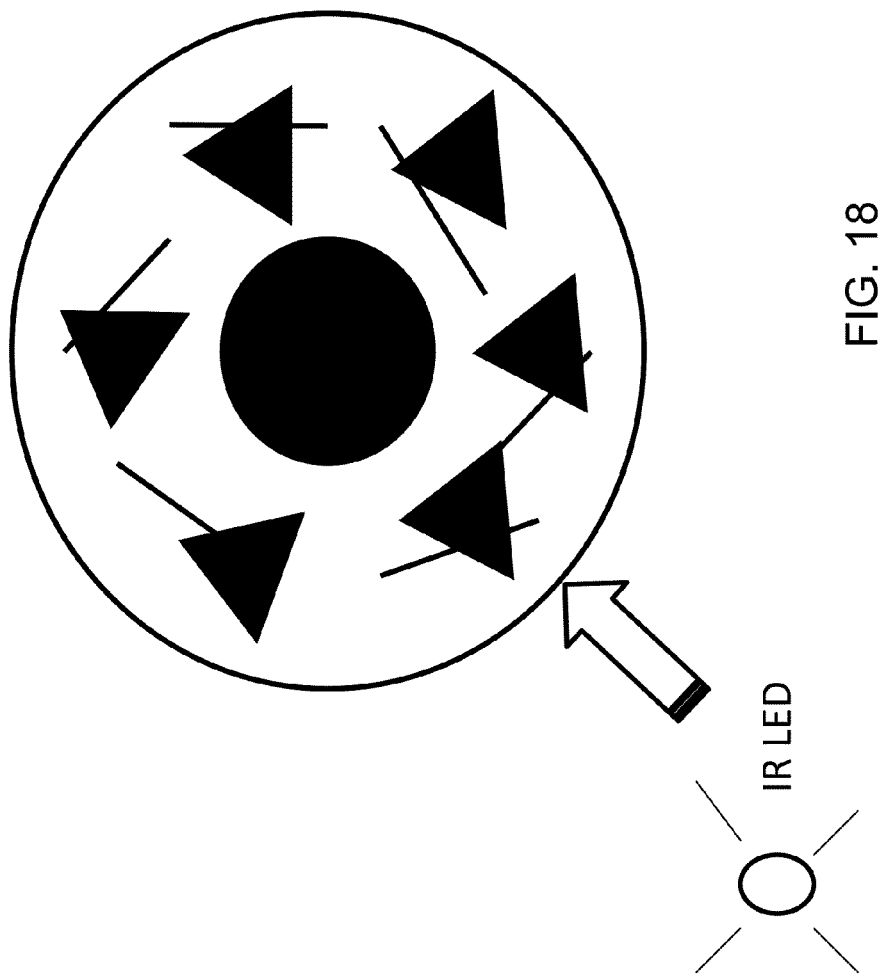
FIG. 18 depicts one embodiment of an image with iris texture and artifacts reflected off an eye surface.
Figure 19:
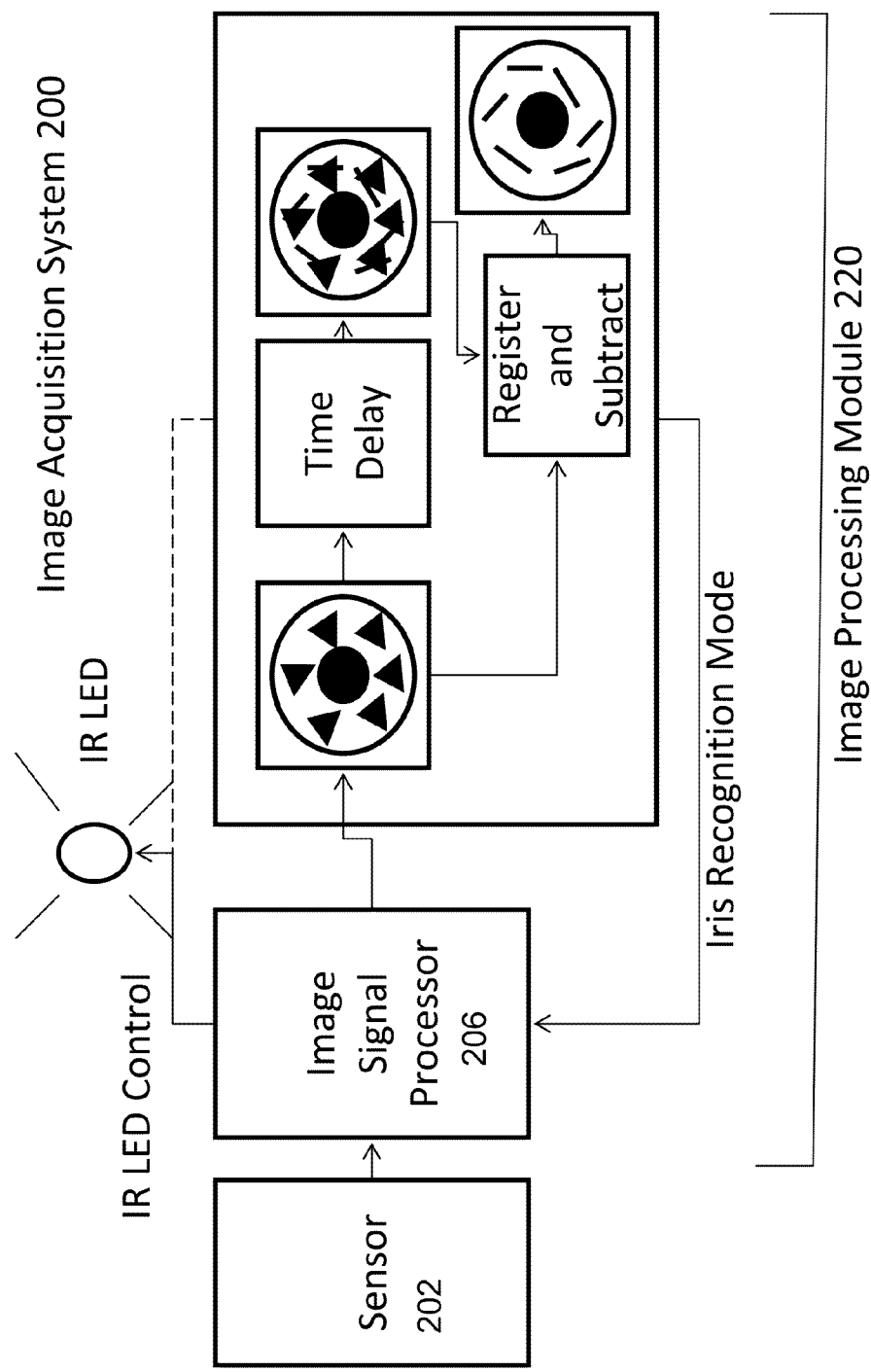
FIG. 19 depicts yet another embodiment of a system for acquisition of face imagery and iris imagery using a single sensor.
Figure 20:
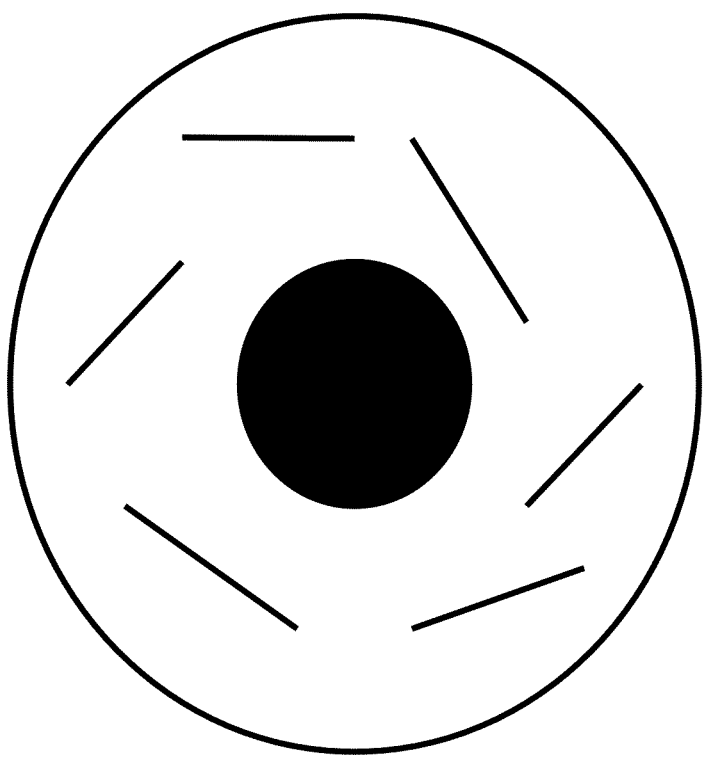
FIG. 20 depicts one embodiment of an image showing iris texture with artifacts removed.

In some embodiments, an image acquired by an image sensor may be affected or corrupted by ambient illumination. For example, in some embodiments, where infra-red filtering and/or illumination is not optimal, images of a scene can be reflected off a surface of an eye (e.g., the cornea) during acquisition of iris imagery. An example of this is shown in FIG. 17. The reflection of imagery (e.g., on the cornea of the eye) may be a reflection of a scene comprising houses surrounding the user, as an example. Such reflections may be referred to as artifacts. We have described, above, how systematic noise can severely impact the performance of iris recognition. The artifacts may be overcome using similar methods: acquire at least two images, one with controlled infra-red illumination turned on, as shown in FIG. 18, and at least a second image with controlled infra-red illumination turned off, as shown in FIG. 17. The image processing module can process these at least 2 images to reduce or remove the artifacts. For example and in some embodiments, the image processing module can align the images and then subtract the images from each other, as shown in the processing diagram in FIG. 19. Since the artifactual illumination is essentially unchanged between the two images, whereas the iris texture is illuminated by the infra-red illumination, the artifact may be removed by taking a difference, whereas the iris texture remains. The remaining iris texture is illustrated by the lines within the iris in FIG. 20. The system may further overcome non-linearities in the sensor by, for example, identifying pixels that are close to or at the non-linear operating range of the sensor (for example saturated or dark). The image processing module may eliminate the identified pixels from subsequent iris recognition processing. Since the image subtraction process in those regions may be non-linear, artifacts may still remain using the subtraction approach.

Figure 21:
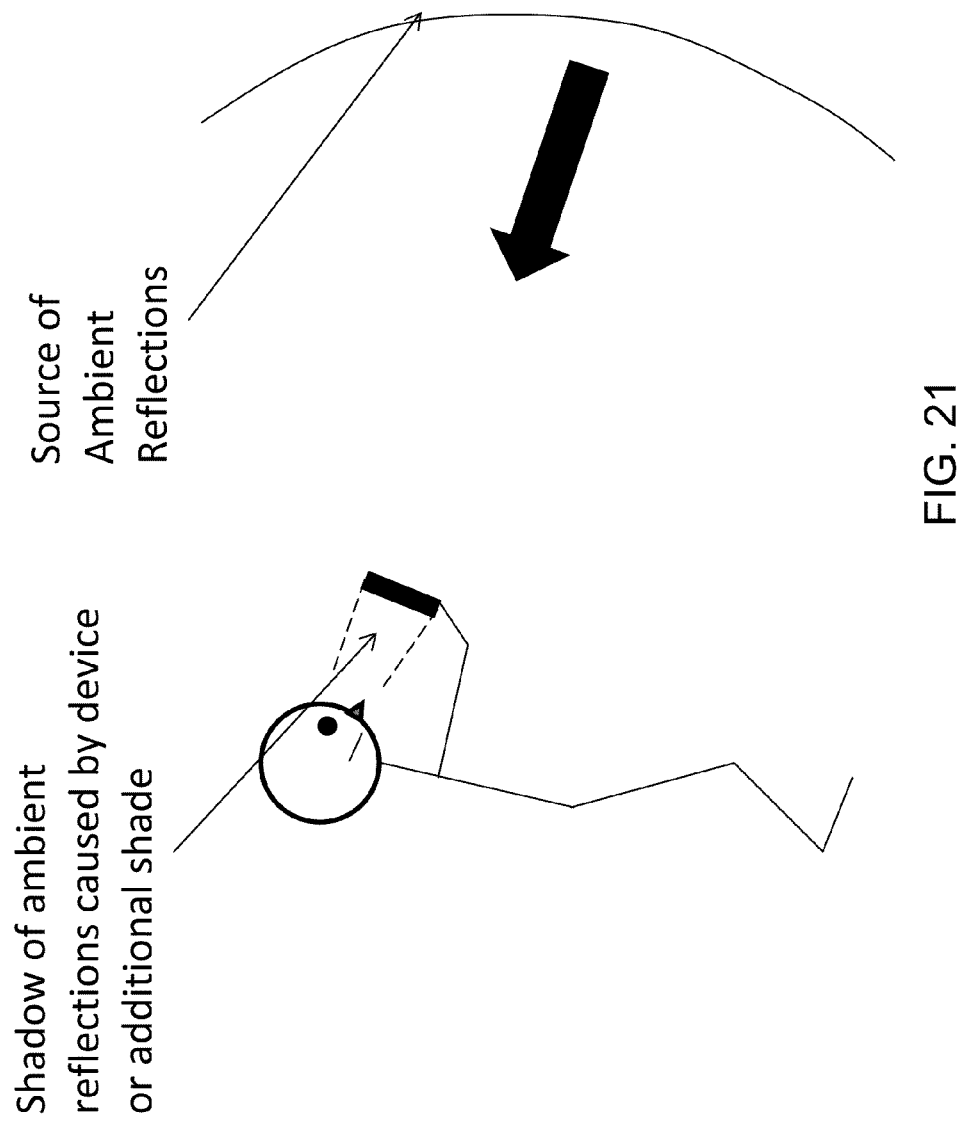
FIG. 21 depicts one scenario for acquisition of face and iris imagery.
Figure 22:
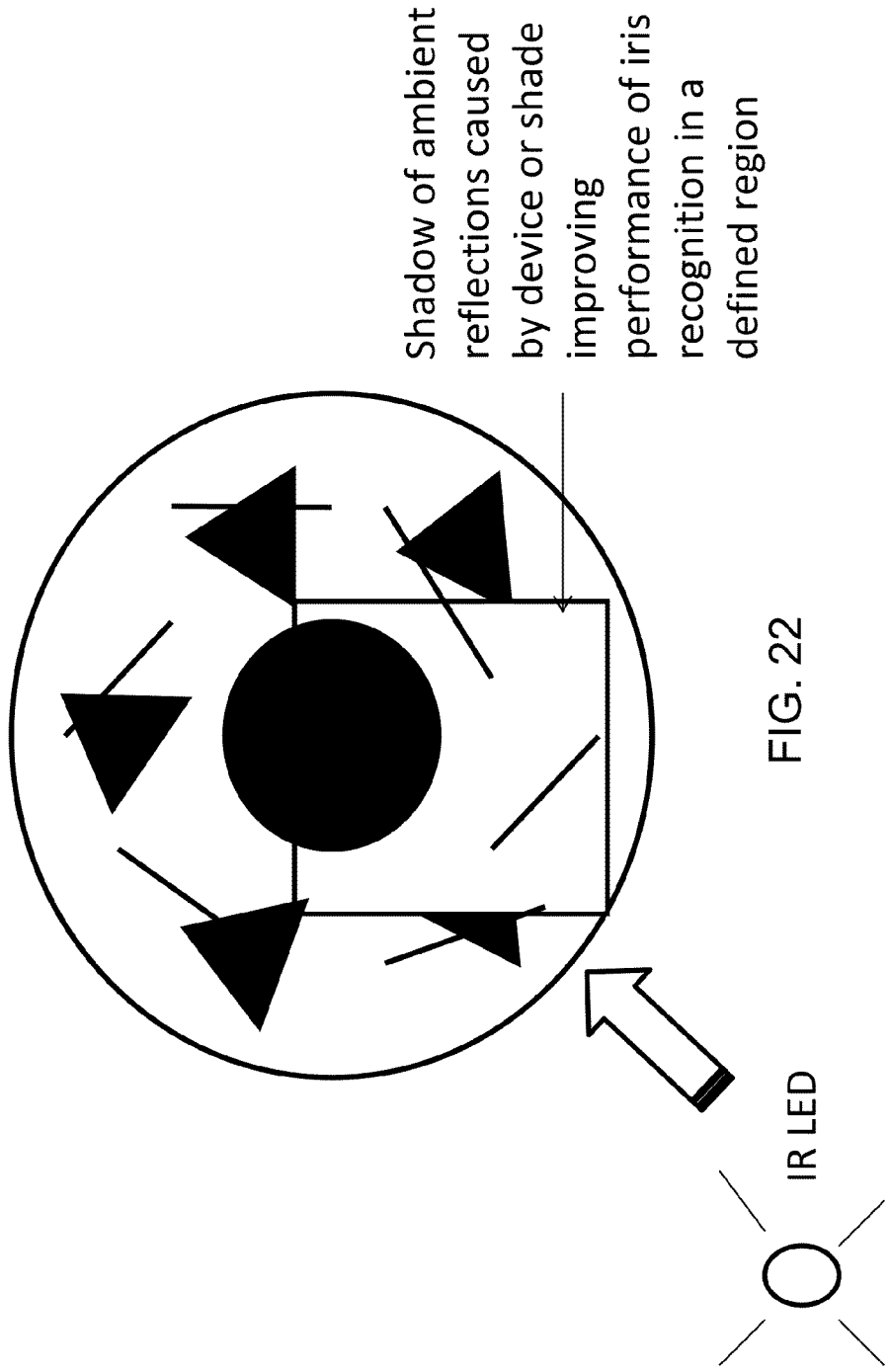
FIG. 22 depicts another embodiment of an image with iris texture and artifacts reflected off an eye surface.

Another embodiment of the present methods manages corruption of images by exploiting particular geometrical constraints of the position of the user, the image-capturing device and the source of the corruption or artifacts. The image processing module may be configured to recognize that as the user holds the image-capturing device in front of the user's face during iris acquisition mode, the image-capturing device may reduce or even block sources of corrupting ambient illumination within one sector of the acquired iris imagery, for example as shown in FIG. 21. The image processing module may limit iris recognition primarily or solely to this sector, thereby avoiding issues related to image corruption, as depicted in FIG. 22. In some embodiments, iris recognition based on this sector of the image may be weighted higher than other sectors in deciding a biometric match.

Figure 23:
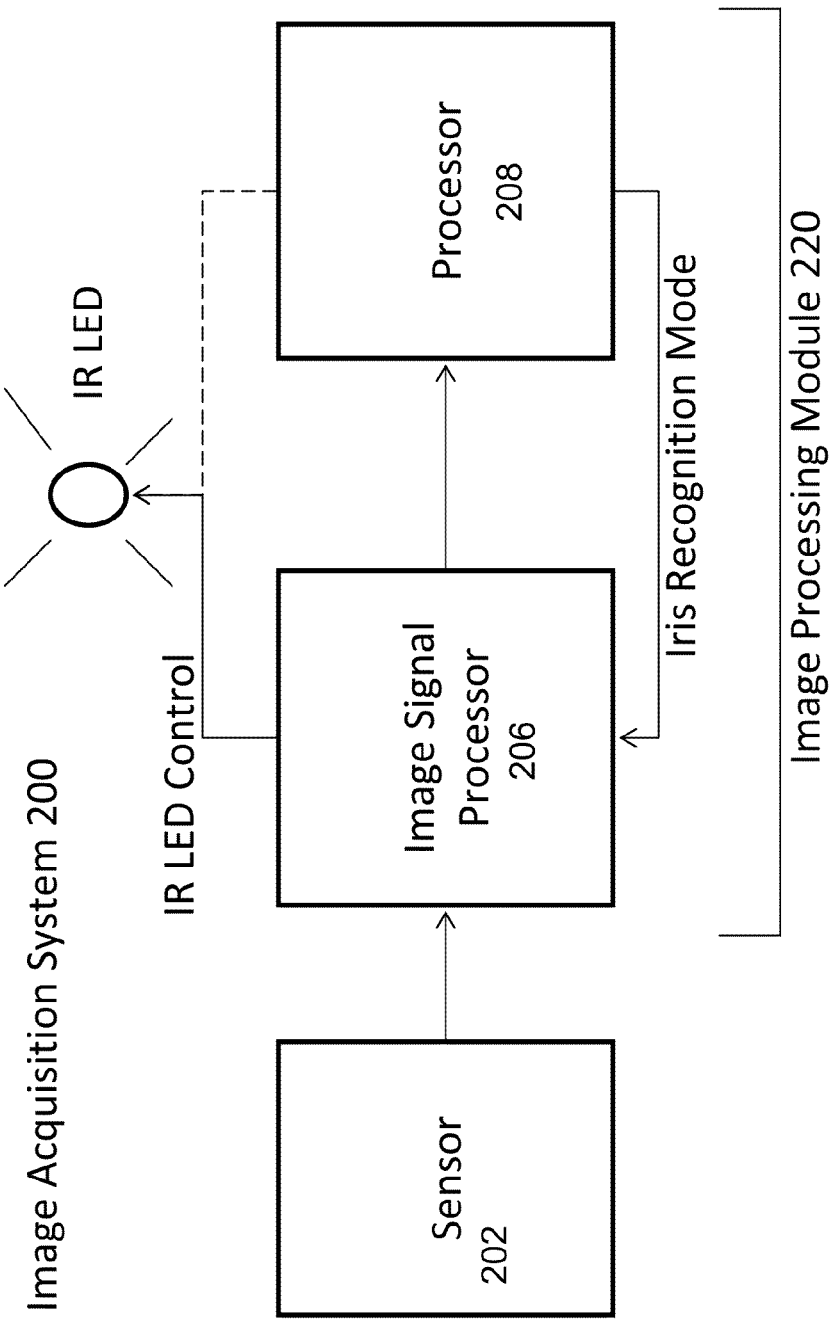
FIG. 23 depicts still another embodiment of a system for acquisition of face imagery and iris imagery using a single sensor.

In some embodiments, infra-red illumination is not readily available or guaranteed during image capture. The image acquisition system 200 may be configured to control and/or provide infra-red illumination. The image acquisition system may reduce power usage by illuminating the infra-red source (e.g., LEDs) when the device is in iris recognition mode, as shown in FIG. 23.

Figure 24:
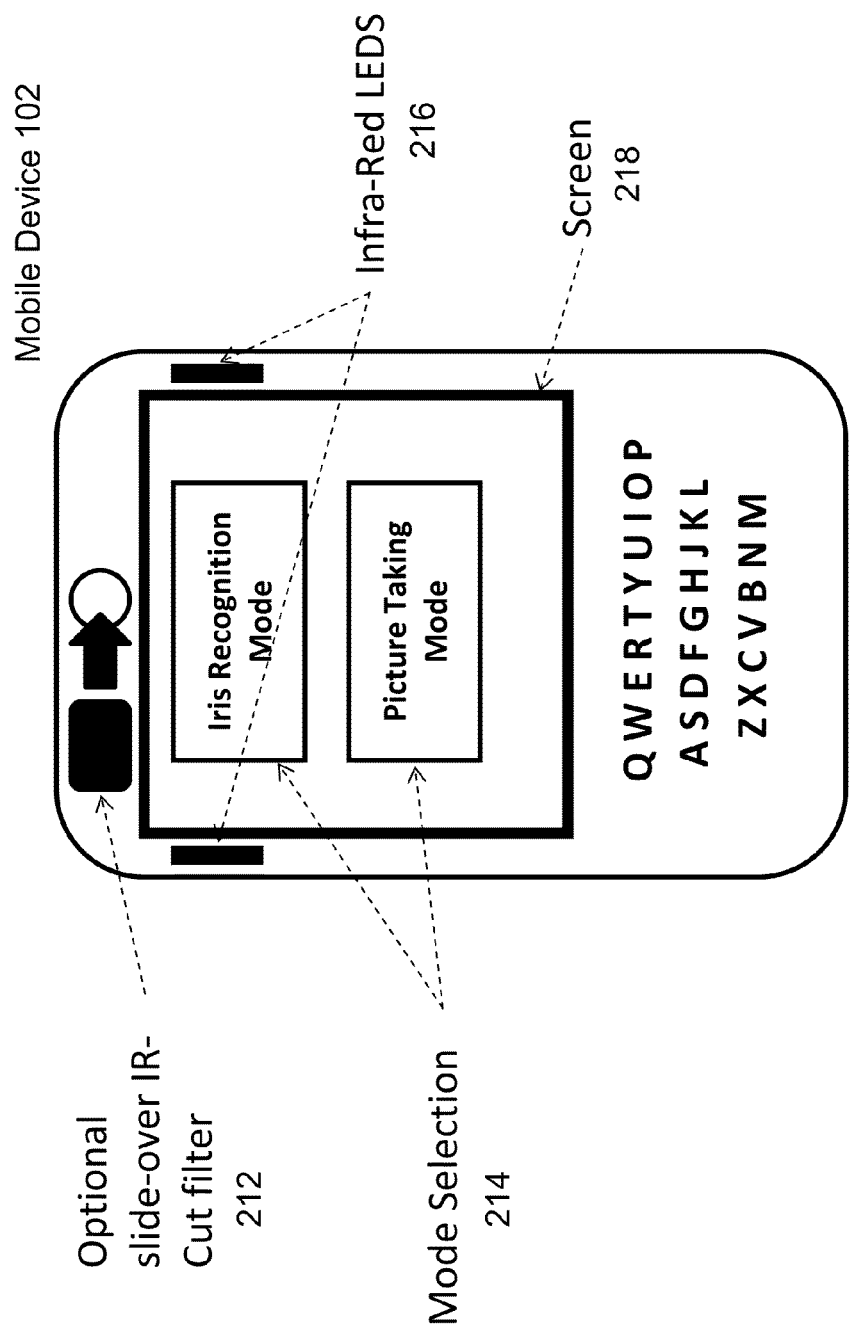
FIG. 24 depicts another embodiment of a system for acquisition of face imagery and iris imagery using a single sensor.

FIG. 24 depicts one embodiment of the image acquisition system 200 using some features of the systems and methods disclosed herein. The image acquisition system 200 may be embodied in a device, such as a mobile and/or compact device. The device may include a screen with a sensor. Infra-red LEDs may provide illumination. A user may use a touch screen or other input device (e.g., keyboard, button or voice command recognition) to switch between iris recognition mode and standard picture-taking mode. The device may include an application, through which a user may activate an image capturing mode. The application may further provide a feedback or guidance mechanism to automatically locate the iris of the user, or guide the user to move the user's iris within a suitable region of capture. In some embodiments, an optional IR-cut filter may be activated or moved over the image sensor, either manually or automatically, when in iris image capture mode. Other filters (e.g., IR-pass filter) may be incorporated and/or activated in the appropriate mode(s). In certain embodiments, certain features of the image acquisition system 200 may be contained in an add-on accessory or sleeve for a mobile or existing device. As an example, such features may include an infra-red illuminator, one or more filters, and/or an interface (e.g., wireless or physical) to the mobile or existing device.

In some embodiments, the image acquisition system 200 may include infra-red illuminators embedded into a screen of the image acquisition system 200, for illuminating a user's eye with infra-red illumination. Screens and displays typically use white LED illumination under an LCD matrix. By adding to or replacing some portion of the visible light LEDs with near infra-red illuminators, a source of IR illumination may be provided by the display itself. In such an embodiment, the image acquisition system 200 may not require an additional fixture or area on the image acquisition system 200 to provide infra-red illumination, thereby saving space.

In certain embodiments, the image acquisition system 200 may include a visible illuminator, for example with two illumination strengths. The visible illuminator may be turned on at low power during iris image acquisition mode. The low power illumination may be chosen so as to not distract or cause discomfort to the user. In some embodiments, brightness level in the low power mode can be at least a factor of 2 darker then the full brightness of the visible illuminator. The latter brightness level may, for example, be used to illuminate a wider scene. The low power visible illuminator may be used to constrict the iris and increase iris area, regardless of whether the user is in the dark or not. However, since the visible illuminator may be close to the eye, some of the filters described above may still pass significant visible light into the sensor. Therefore, in some embodiments, the visible light is turned off before images of the iris is acquired while the near infra-red illuminator turned on. In an alternate embodiment, the screen itself can be used as a source of visible illumination.

In some embodiments, one advantage of using a single sensor in the image acquisition system 200 is that space occupied by the system can be minimized compared to the use of dual sensor. However, in either case, an important consideration is the ability of the user and/or operator to use the single-sensor or dual-sensor device effectively.

Figure 25:
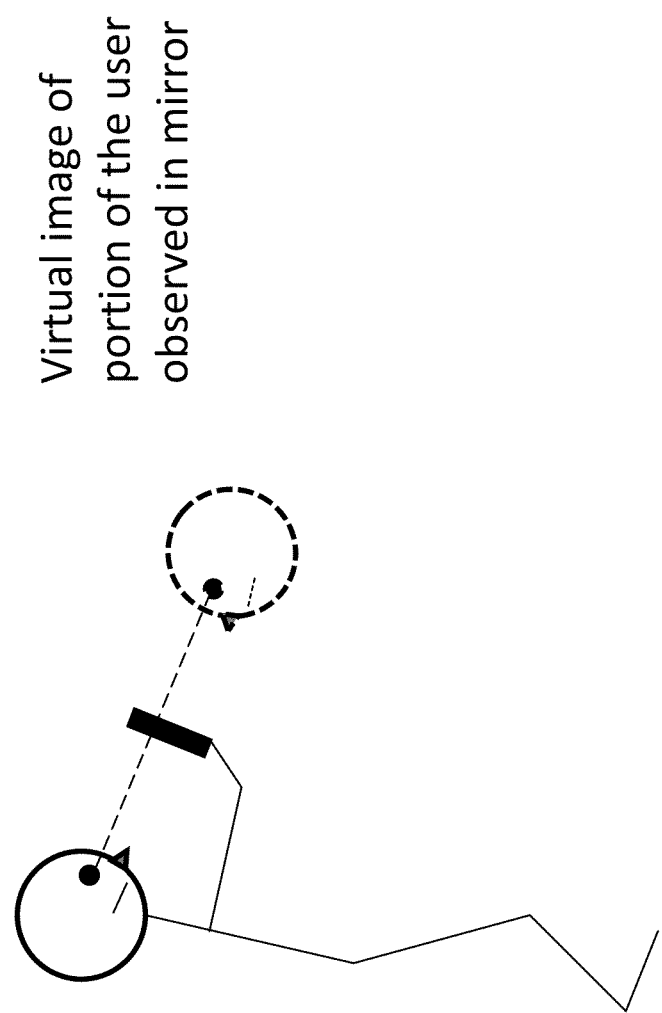
FIG. 25 depicts one embodiment of a system for acquisition of face imagery and iris imagery using a single sensor and a mirror.

In some embodiments, a mirrored surface may be used to help guide an user in aligning the user's iris with a suitable capture zone of the image sensor. A mirrored surface can provide feedback to the user of the user's position, as depicted in FIG. 25, where a user is holding a device in front of them and a virtual image of a portion of the user's face is viewed at twice the distance from the user to the device. However, because of a property of the human visual system, ocular dominance, and the requirements of our iris recognition system, the optimal size of the mirror may not scale linearly with the distance of the user to the mirror as might be expected. In fact, under some conditions, an increase in the size of the mirror to try and improve iris recognition performance may degrade performance or cause difficulty in alignment.

Ocular dominance is a tendency to prefer visual input from one eye or the other. It occurs in most individuals, with ⅔ of individuals having right-eyed dominance and ⅓ of individuals having left-eyed dominance. The present systems and methods address ocular dominance and combine properties of ocular dominance with constraints of iris recognition in order to maximize the size of recovered iris imagery while minimizing the size of a mirror used to guide the user.

Figure 26:
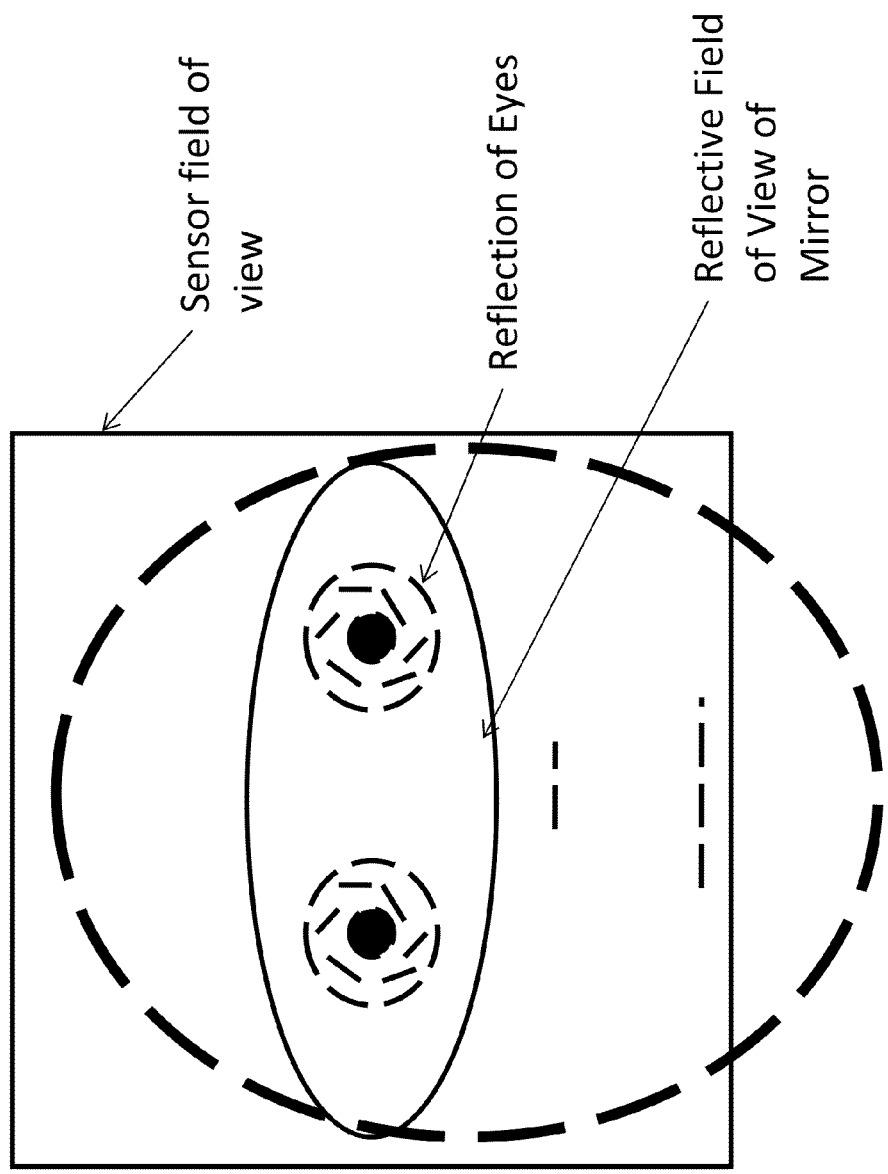
FIG. 26 depicts one embodiment of a method for acquisition of face imagery and iris imagery using a single sensor and a mirror.
Figure 27:
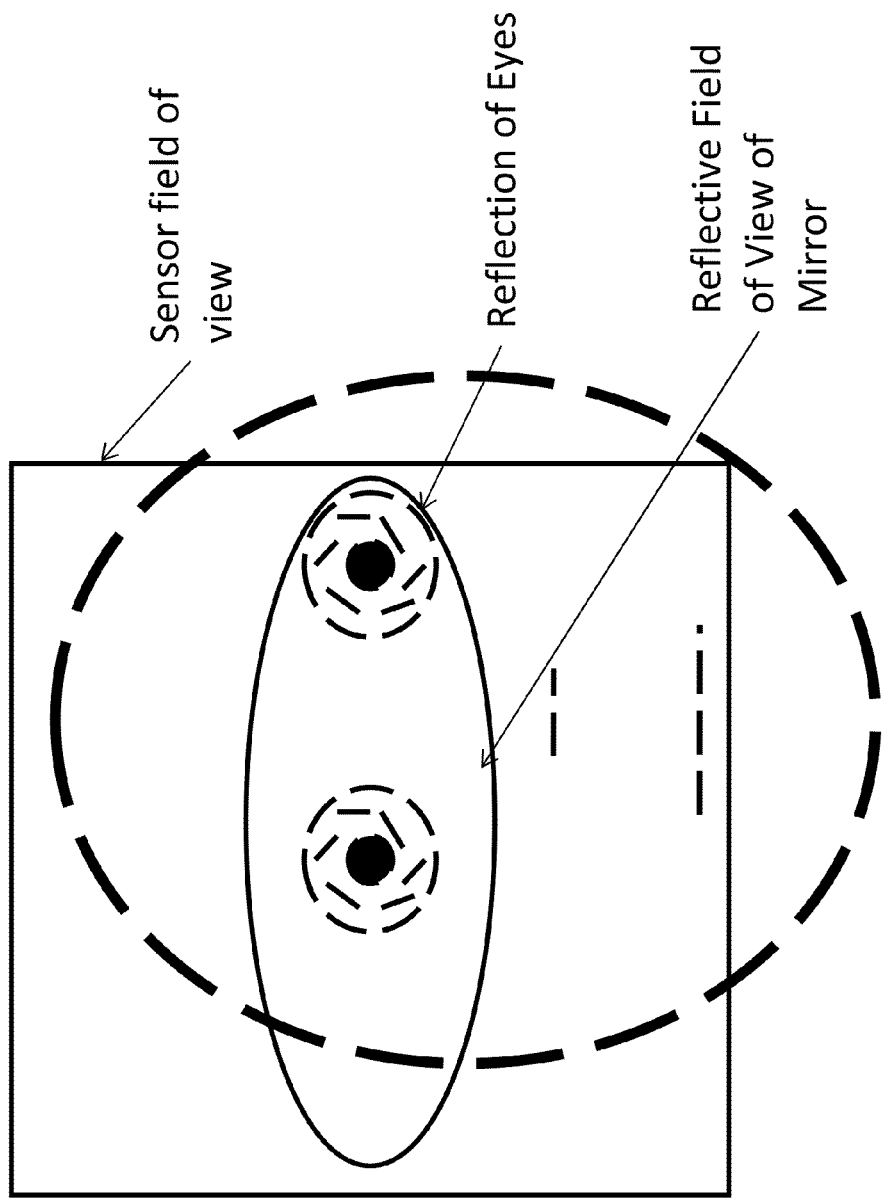
FIG. 27 depicts an effect of ocular dominance on the acquisition of face imagery and iris imagery.

FIG. 26 depicts a reflective field of view of a mirror of a size such that both eyes occupy comfortably the field of view. In some embodiments, the width of the mirror is such that at the viewing distance of the image acquisition device 200, the reflective field of view may be at least approximately 50% wider than the reflection of the eye separation. For illustrative purposes, the user is shown in the middle of the mirror. FIG. 27 however shows that in practice, due to ocular dominance, a user typically is positioned to one side of the mirror, such that their dominant eye is closer to the center of the mirror. If the width of the field of view of the mirror is greater than 50% of the field of view of a typical eye separation for users (6.5-7 cm), then the eyes may remain in the field of view. Therefore, both eyes may be acquired by the image acquisition system 200 for people with ocular dominance since both eyes may remain in the field of view of the image sensor in such a case. However, the iris diameter in the captured image may be relatively small since a lens for the sensor is typically chosen to cover a wide field of view.

Figure 28:
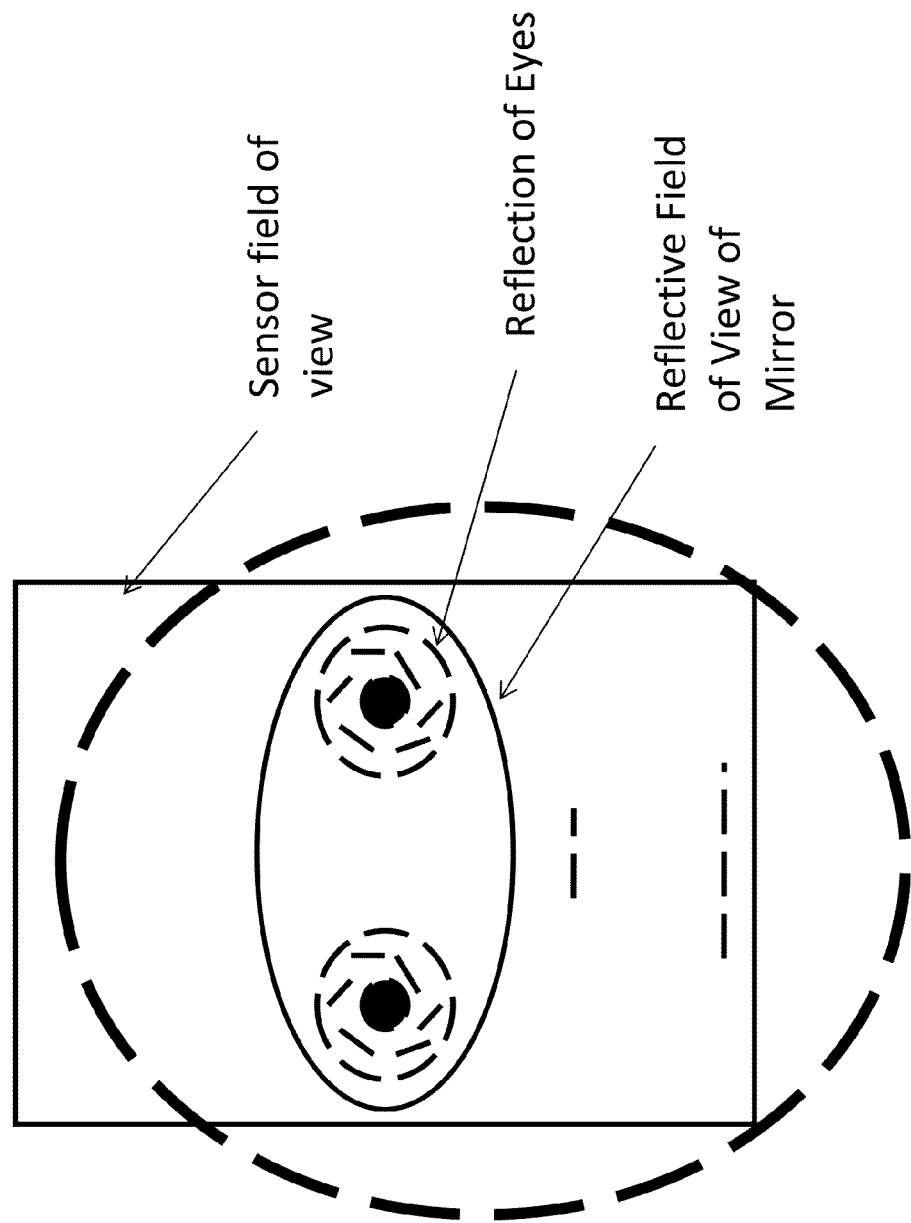
FIG. 28 depicts another embodiment of a system for acquisition of face imagery and iris imagery using a single sensor and a mirror.
Figure 29:
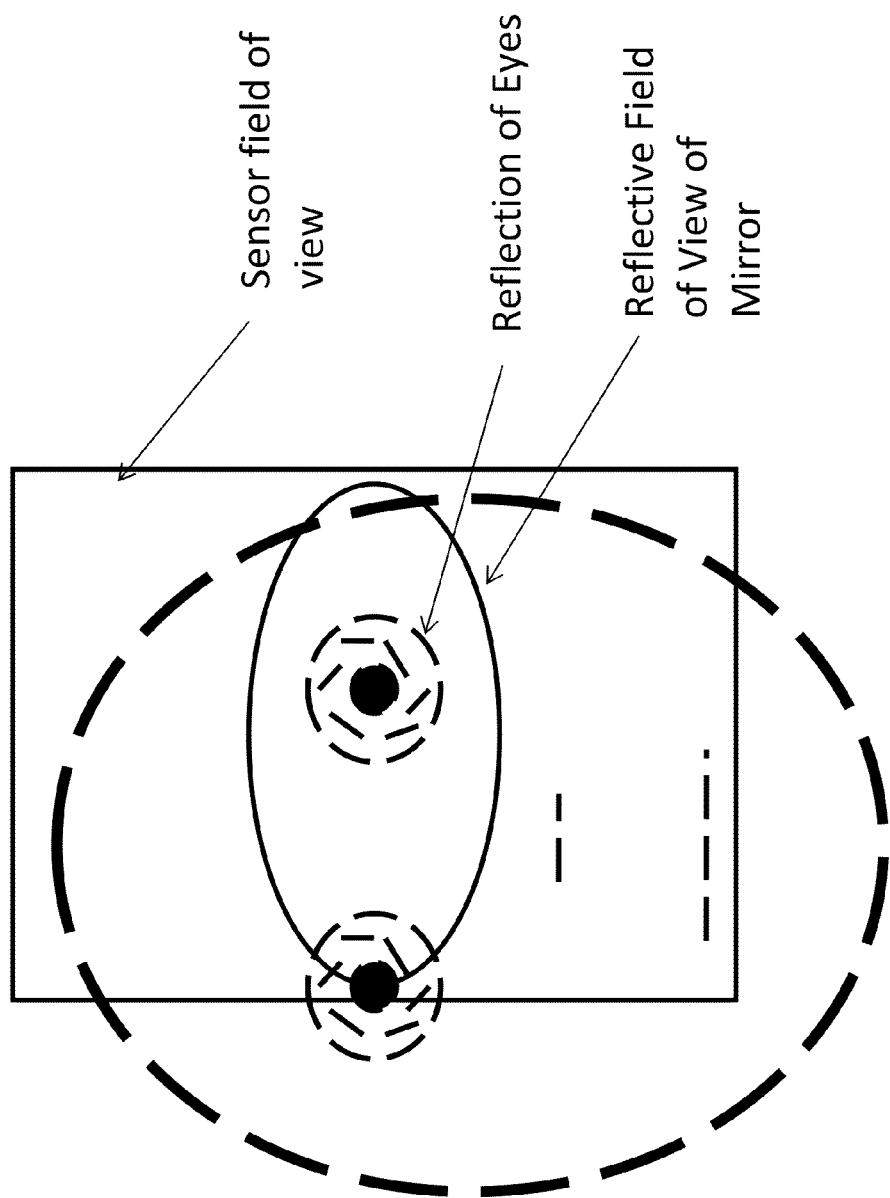
FIGS. 29 and 30 depict the effect of ocular dominance on the acquisition of face imagery and iris imagery.
Figure 30:
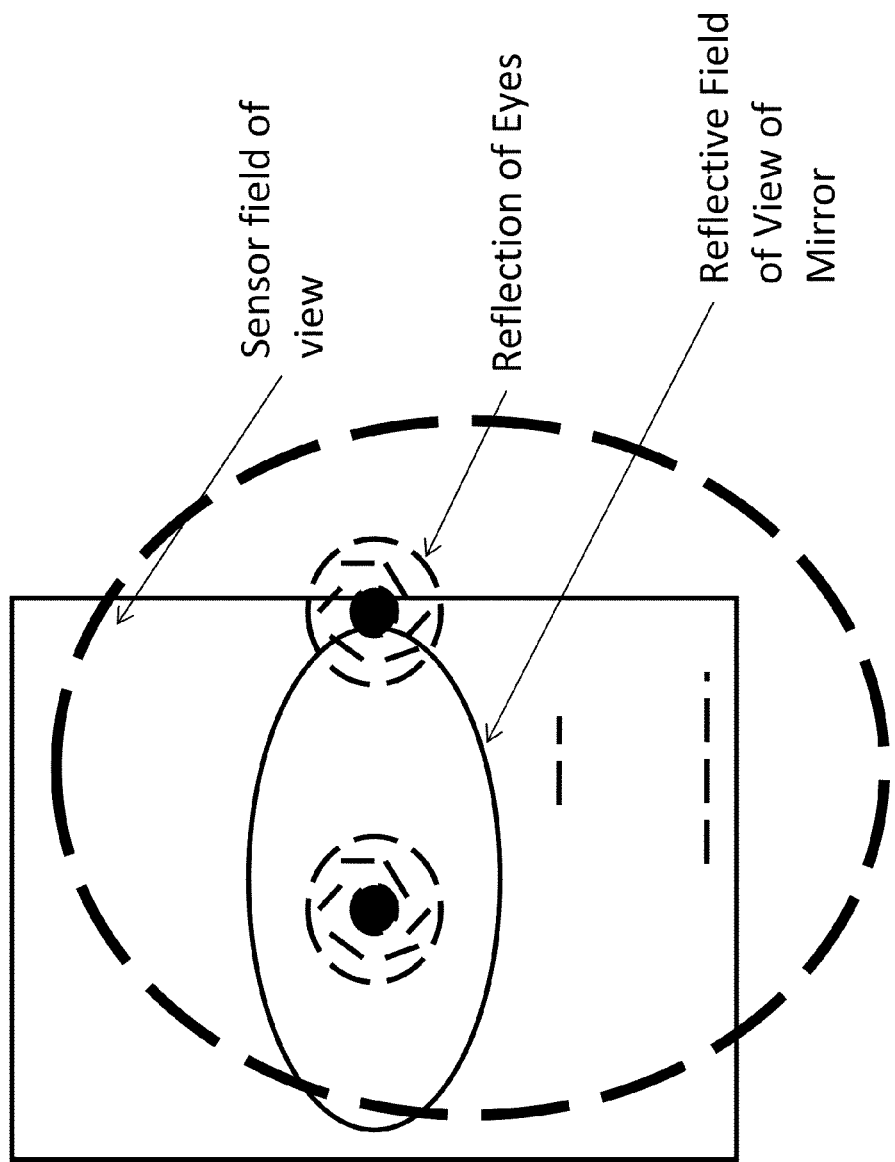

FIG. 28 depicts, without consideration of ocular dominance, a configuration for acquiring images of both eyes using a smaller mirror. The field of view of the mirror is smaller thereby minimizing its area on any image acquisition system 200. Both eyes may be acquired if the user is positioned in the center of the mirror. However as described above, due to ocular dominance, the user is typically positioned to the right or to the left of this optimal position, as shown in FIGS. 29 and 30. In this scenario, one of the eyes may be out of the field of view of the camera. Thus, although this configuration has a moderately large mirror, and even if the lens may be configured to acquire both eyes (when in a central position), due to ocular dominance, the image acquisition system 200 may only acquire a single eye reliably in practice.

Figure 31:
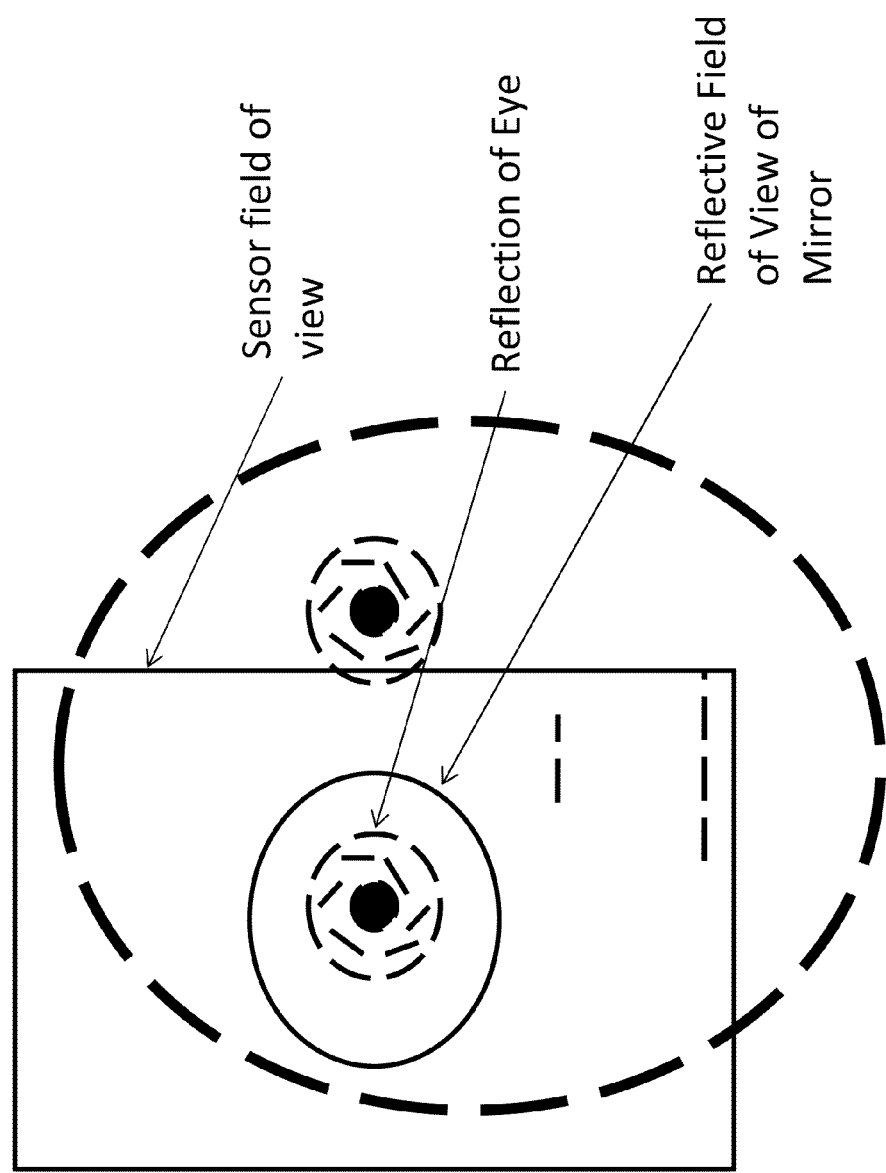
FIG. 31 depicts yet another embodiment of a system for acquisition of face imagery and iris imagery using a single sensor and a mirror.

FIG. 31 depicts a design that acquires higher resolution iris imagery compared to FIG. 30 (, i.e., improving iris recognition performance) yet uses a smaller mirror such that only the dominant eye is observed by the user. By limiting the size of the mirror so that only the dominant eye is in the field of view, the tendency for the user's visual system to choose the left or the right eye is forced to be a binary response (e.g., left or right eye), as oppose to a variable or unpredictable response (e.g., eyes shifted to the left or right) in the field of view. In a some embodiments, the image acquisition system 200 may operate or include a mirror with a diameter of about 14 mm at an operating distance of approximately 9", such that the reflective field of view of the mirror corresponds to approximately 2 typical iris diameters (2×10.5 mm). FIG. 32 summarizes and illustrates the size of the effective field of view of the mirror and its relationship to 1 or 2-eye capture and also the size of the acquired iris imagery.

Figure 33:
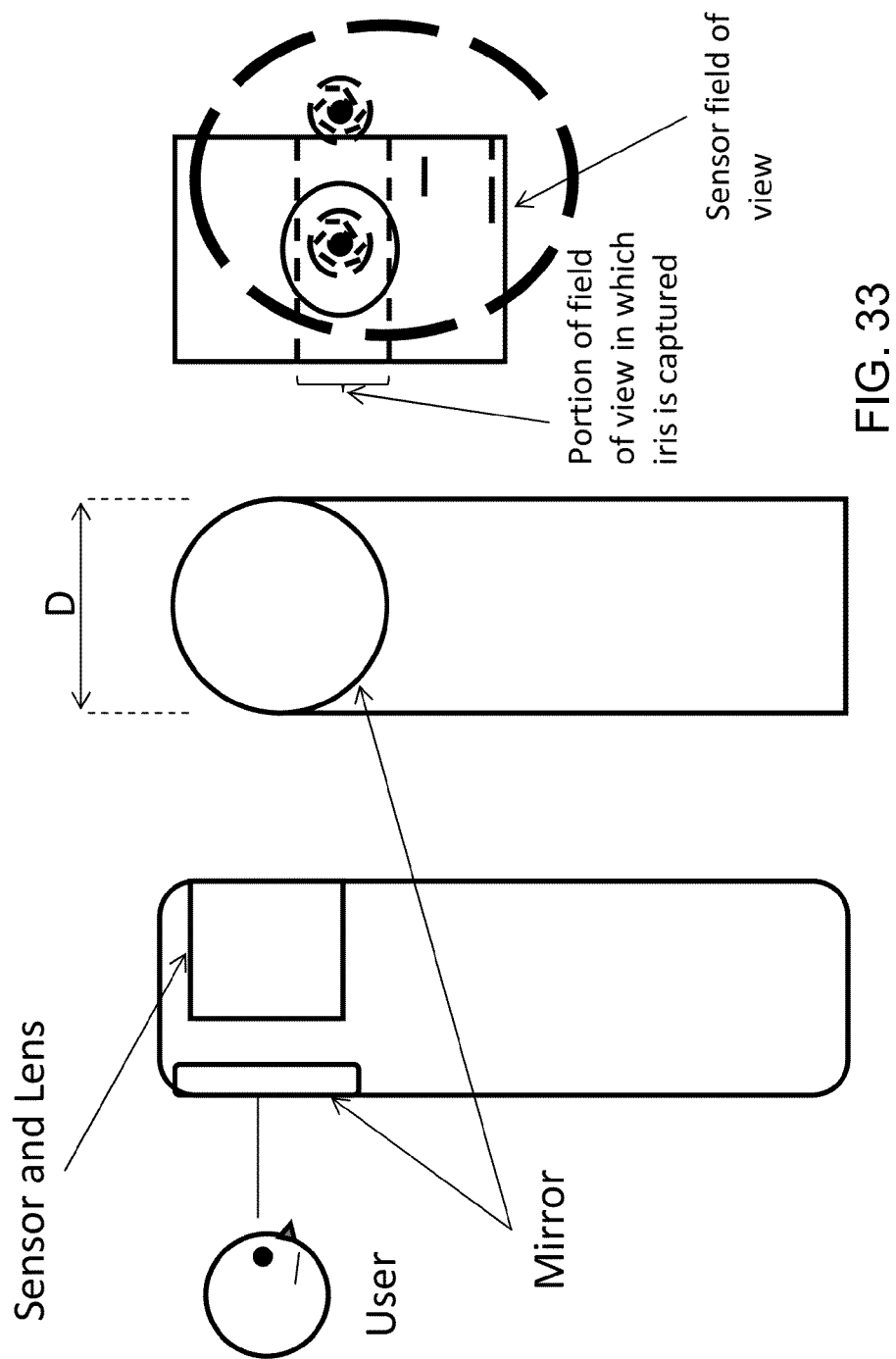
FIG. 33 depicts another embodiment of a system for acquisition of face imagery and iris imagery using a single sensor and a mirror.
Figure 34:
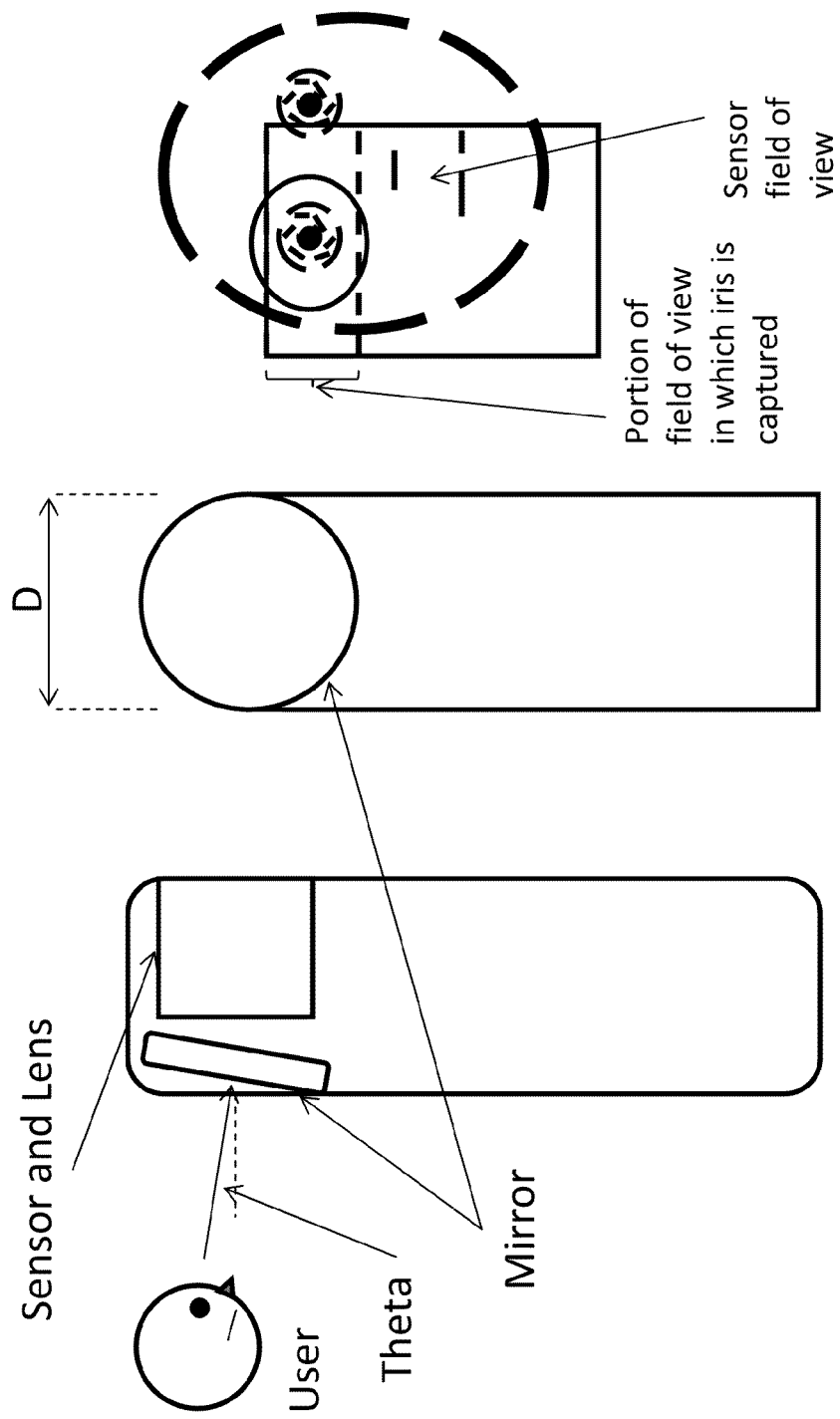
FIG. 34 depicts still another embodiment of a system for acquisition of face imagery and iris imagery using a single sensor and a mirror.

FIG. 33 depicts one embodiment of the image acquisition system 200 whereby an IR-cut filter is placed over a portion of the sensor. A face or other imagery can be acquired by a portion of the sensor while imagery for iris recognition is acquired by a portion covered by the IR-cut filter. Ocular dominance tends to provide uncertainty in a horizontal direction due to the horizontal configuration of human eyes, and therefore the image acquisition system 200 may be correspondingly configured with a horizontally shaped filter region over the sensor. FIG. 34 depicts another embodiment in which the mirror is tilted such that the user observes the sensor/lens assembly at an angle, and the eyes are close to the top of the sensor rather than in the middle of the sensor. This configuration may allow placement of the IR-cut filter at one end of the sensor, thereby allowing the sensor to have two distinct regions (IR-cut and non-IR-cut) rather than 3 regions (non-IR-cut, IR-cut and non-IR-cut), which is the case illustrated in FIG. 33. This allows a larger and more contiguous non-iris portion of a scene to be acquired.

Figure 35:
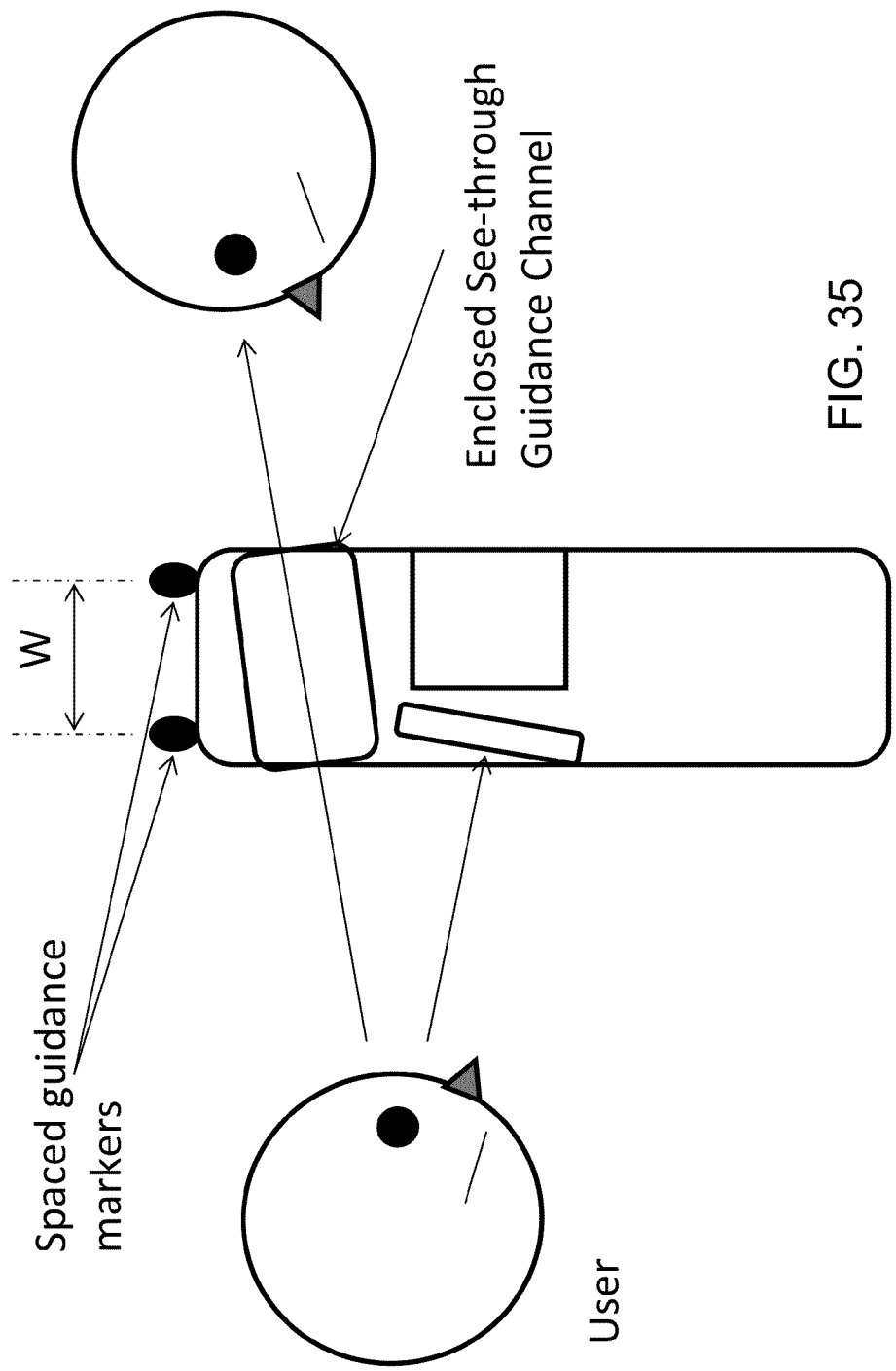
FIG. 35 depicts another embodiment of a system for acquisition of face imagery and iris imagery using a single sensor.
Figure 36:
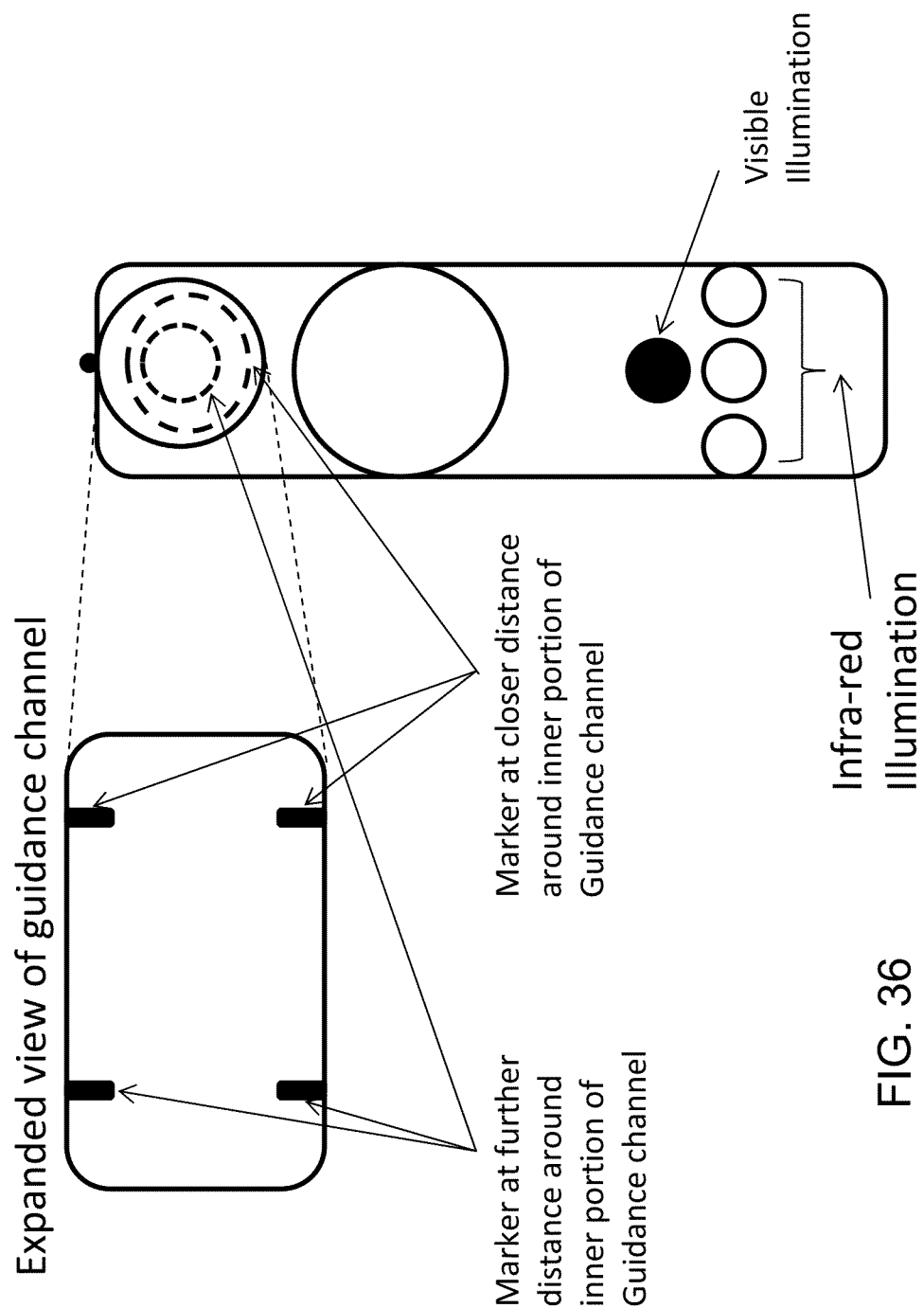
FIG. 36 depicts yet another embodiment of a system for acquisition of face imagery and iris imagery using a single sensor.
Figure 37:
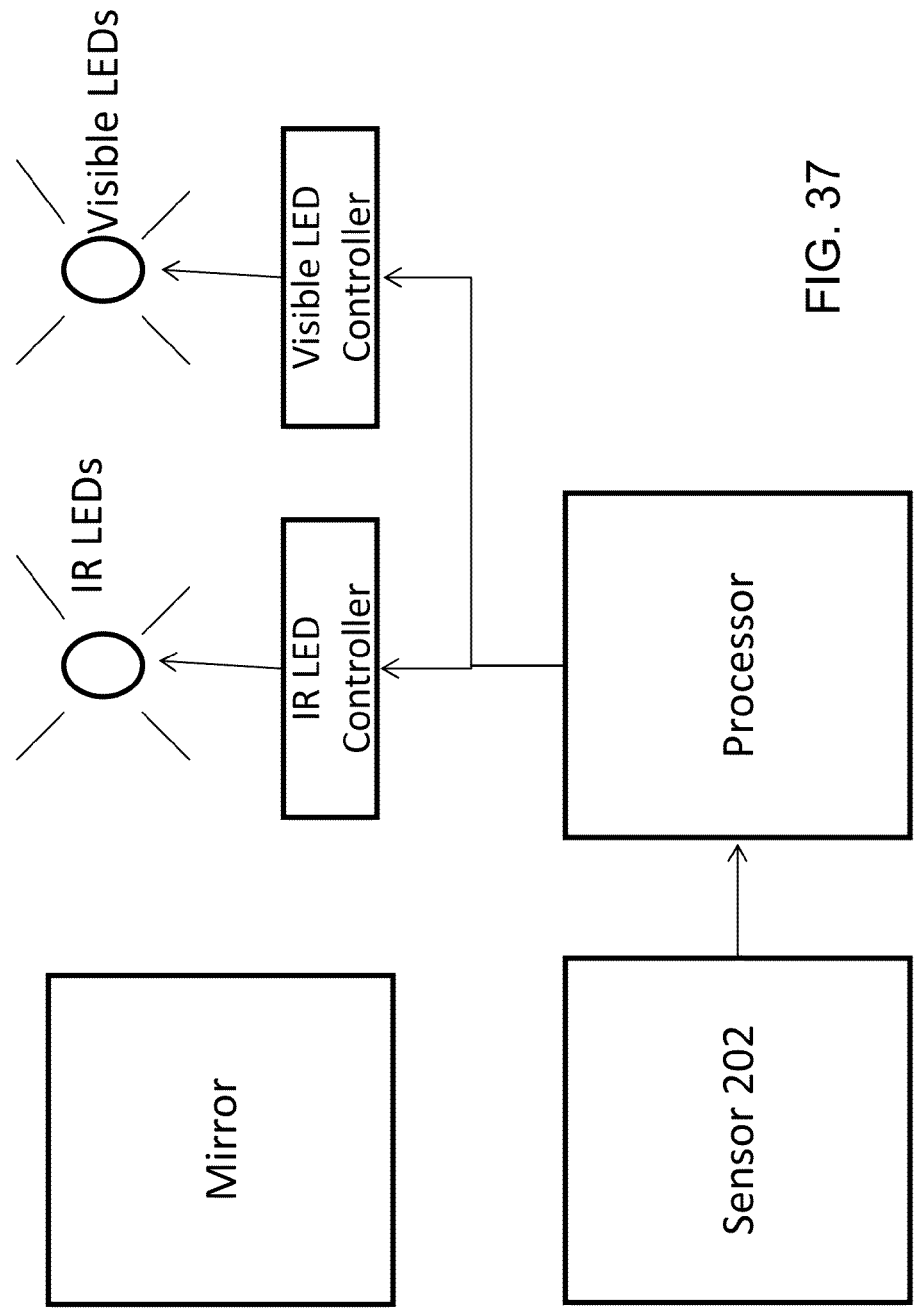
FIG. 37 depicts still another embodiment of a system for acquisition of face imagery and iris imagery using a single sensor.

FIG. 35 shows another embodiment of the image acquisition system 200 whereby an operator may be holding the image acquisition device 200, in order to acquire iris imagery of the user. In this embodiment, there is a see-through guidance channel through which the operator can look to line up with the user's eye. In addition or alternatively, spaced guidance markers can be placed on top of the image acquisition device 200, so that the operator lines up the user's eye with two markers for example. FIG. 36 shows an expanded view of one embodiment of a guidance channel. In this embodiments, circular rings may be printed on the inner portion of the guidance channel, at the back and front of the guidance channel as shown. When the user is aligned, these rings may appear to be concentric to the operator. Otherwise, they will be non-concentric (user's eye is misaligned). FIG. 36 also shows a visible illuminator (LED) on the device, as well as Infra-red illuminators which may used for the purposes of the iris recognition. FIG. 37 depicts another embodiment of the image acquisition system. In this embodiment, the LEDs are controlled by controllers that are in turn connected to a processor that is also connected to the sensor used for iris recognition.

Figure 38:
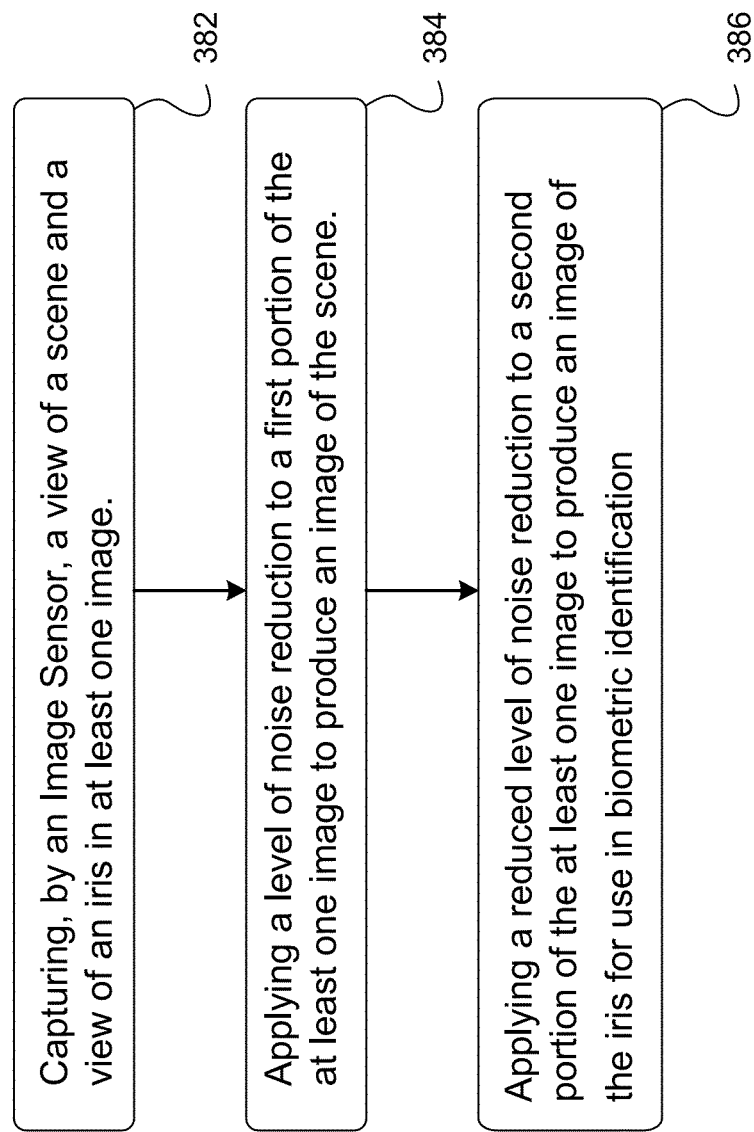
FIG. 38 is a flow diagram illustrative of one embodiment of a method for acquisition of scene imagery and iris imagery using a single sensor.

Illustrated in FIG. 38 is one embodiment of a method for capturing images of an iris and a scene using a single image sensor. An image sensor captures a view of a scene and a view of an iris in at least one image (382). An image processing module applies a level of noise reduction to a first portion of the at least one image to produce an image of the scene (384). The image processing module applies a reduced level of noise reduction to a second portion of the at least one image to produce an image of the iris for use in biometric identification (Step 386).

Further referring to FIG. 38, and in more detail, an image sensor 202 of an image acquisition system 200 captures a view of a scene and a view of an iris in at least one image (382). The image sensor may capture the view of the scene in one image and the view of the iris in another image. In some embodiments, the image sensor may capture the view of the scene and the view of the iris in a single image. For example, the view of the scene may include at least a portion of the iris. The image sensor may capture the view of the scene and the view of the iris in a plurality of images. The image sensor may capture the view of the scene in some images and the view of the iris in other images. The image sensor may capture the view of the scene and the view of the iris in some images. The image sensor may capture two or more images over a period of time. The image sensor may capture two or more images within a short timeframe of each other, e.g., for later comparison or processing. The image sensor may capture two or more images under different conditions, for example, with and without infra-red illumination, or with or without using any type of filter discussed herein.

In some embodiments, the image acquisition system 200 may comprise an iris capturing mode and a picture (e.g., non-iris) capturing mode. The image sensor may capture an image of the view of the scene in picture capturing mode. The image sensor may capture an image of the view of the iris in iris capturing mode. In certain embodiments, the image acquisition system 200 may perform concurrent capture of iris and non-iris imagery in another mode. A user may select a mode for image acquisition, for example, via an application executing on the image acquisition device 200. In some embodiments, the image acquisition system may capture the view of the scene and the view of the iris as separable components within a single image. The image acquisition system may capture the view of the scene and/or the view of the iris using any embodiment and/or combination of the interleaved filter, IR-cut filter, IR-pass filter, and other types of filters described herein.

In some embodiments, the image sensor comprises a plurality of sensor nodes of the image sensor. The image sensor may activate a first subset of the sensor nodes adapted primarily for capturing an image of the iris suitable for biometric identification. The image sensor may activate a second subset of the sensor nodes adapted primarily for capturing a non-iris image. An IR-pass, (G+I) filter (e.g., allowing G+I to pass), or other filter may be applied over a sensor node adapted primarily for capturing an image of the iris. An IR-cut, visible-pass, specific bandpass or color filter may be applied over a sensor node adapted primarily for capturing a non-iris image.

In some embodiments, the image sensor captures at least one image of the iris while illuminating the iris with infra-red illumination. The image sensor may capture at least one image of the iris without infra-red illumination. The image sensor may capture at least one image of the iris upon turning off a visible light illuminator. The image sensor may capture at least one image of the iris using illumination from a screen of the image acquisition system 200. The image sensor may capture at least one image of the iris when the iris is aligned with a portion of the sensor using a mirror of the image acquisition system 200 for guidance. The image sensor may capture at least one image of the iris when the iris is aligned with a portion of the sensor by an operator using a see-through guidance channel and/or markers.

Further referring to (384), an image processing module may apply a level of noise reduction to a first portion of the at least one image to produce an image of the scene. The image acquisition system 200 may apply noise reduction on an image captured by the image sensor. The image acquisition system 200 may apply noise reduction on an image stored in the image acquisition system 200, e.g., in a storage device or buffer. The image acquisition system 200 may apply noise reduction comprising applying an averaging or median function or filter over some pixels of an images, e.g., over a 3×3 pixel window. The image acquisition system 200 may apply noise reduction comprising reduction of one of, or both of time-varying and time-invariant noise from a captured image. The image acquisition system 200 may account for or exclude a known faulty pixel while performing image processing and/or noise reduction. The image acquisition system 200 may apply noise reduction using an image processing module which may include one or more image signal processors 206 and/or other processor 208. The image acquisition system 200 may apply noise reduction by identifying, accounting for and/or compensating for the presence of systematic noise.

In some embodiments, the image processing module may apply noise reduction on an image captured in non-iris capturing mode. The image processing module may apply a level of noise reduction to a portion of an image not for iris biometric identification, e.g., a portion corresponding to an IR-cut filter. The image processing module may apply noise reduction or filtering on a general or non-iris image. The image processing module may generate an image of a general scene that is perceptibly better (e.g., to a human) than an image before noise reduction.

Further referring to (386), the image processing module may apply a reduced level of noise reduction to a second portion of the at least one image to produce an image of the iris for use in biometric identification. In some embodiments, the image processing module may disable noise reduction on an image for use in iris biometric identification. The image processing module may determine that the noise level does not overwhelm the captured iris texture. The image processing module may perform iris biometric identification based on a raw or unprocessed image captured by the image sensor. The image processing module may perform iris biometric identification based on image captured by the image sensor after some processing, e.g., removal of artifacts, sporadic noise and/or systematic noise.

In some embodiments, the image processing module may apply a reduced level of noise reduction to an image for use in iris biometric identification. The image processing module may apply a reduced level of noise reduction to an image captured while in iris capturing mode. The image processing module may perform noise reduction for systematic and/or sporadic noise. The image processing module may disable noise reduction for non-systematic noise. The image processing module may apply a reduced level of noise reduction to a portion of an image extracted for iris biometric identification, e.g., a portion corresponding to an IR-pass filter. The image processing module may apply reduction of systematic noise to a portion of an image extracted for iris biometric identification, e.g., a portion corresponding to an IR-pass filter.

In some embodiments, the image processing module 220 subtracts noise from one image of the iris with noise from another image of the iris. Such subtraction may result in reduced systematic noise and/or sporadic noise. The image processing module 220 may align two images together to perform the subtraction. The image processing module 220 may align two images using common points of reference (e.g., edge of shapes). The image processing module 220 may align two images by using pattern recognition/matching, correlation and/or other algorithms. The image processing module 220 may subtract noise corresponding to overlapping portion of two images. The image processing module 220 may reduce ambient noise in one image using ambient noise from another image. Ambient noise may comprise signals from ambient light or illumination. Ambient noise may comprise artifacts from surrounding illumination sources or reflections of surrounding objects off a surface of the eye. In some embodiments, the image processing module 220 may reduce ambient noise from one image captured in the presence of infra-red illumination, using ambient noise from another image captured without infra-red illumination.

In certain embodiments, the image processing module 220 may recover an infra-red component from one or more (G+I) pixels imaged on a sensor node array. The image processing module 220 may subtract the G component from (G+I) using a G intensity value in a neighboring pixel. In some embodiments, the image processing module 220 may subtract the G component using an estimated G intensity value. The image processing module 220 may use the estimated G intensity value in processing a non-iris (e.g., general scene) portion of an image. In some embodiments, the image processing module 220 may perform gain or brightness control or adjustment on a portion of the at least one image, to produce an image of the iris for use in biometric identification. In some embodiments, the amount of infra-red illumination may be insufficient or sub-optimal, so that gain or brightness control or adjustment can improve iris image quality. In certain embodiments, gain or brightness control or adjustment may be preferable to adding infra-red illuminators, drawing power to provide infra-red illumination, and/or controlling infra-red illumination (e.g., under different conditions). Since infra-red signals are captured by a fraction of the sensor nodes/pixels (e.g., in a RGB(G+I) array), compensation via gain or brightness control or adjustment may be appropriate.

In some aspects, the present systems and methods is directed to a compact, mobile biometric system. The compact, mobile biometric system may acquire imagery primarily to determine or verify the identity of an individual person. The mobile biometric system may use biometric recognition using the iris. The mobile biometric system may capture pictures of faces for subsequent biometric recognition or viewing by a human.

In some embodiments, the biometric device is designed so that a user can not only use it without help from an operator, but can also carry it with the user. In this way there is no equipment at a location for a thief to steal, and also no equipment to be maintained at a location. Compact, mobile devices exist for the fingerprint biometric, whereby a fingerprint reader is embedded onto a USB key device. A user places their finger on the device and the fingerprint is read. However we have found that this approach is not suitable for the iris or face biometric. For example, if the mobile fingerprint reader device is plugged into a USB (or other) socket of a computer, then a user can easily contort their finger to swipe the reader of a fingerprint reader device, but it is much more difficult and very inconvenient to orientate their eye and body to orientate towards an iris or face biometric acquisition device. We have developed a mobile biometric device that enables acquisition of the iris and/or iris by a user very easily and effectively, but also in a platform that is simple to carry.

Figure 39:
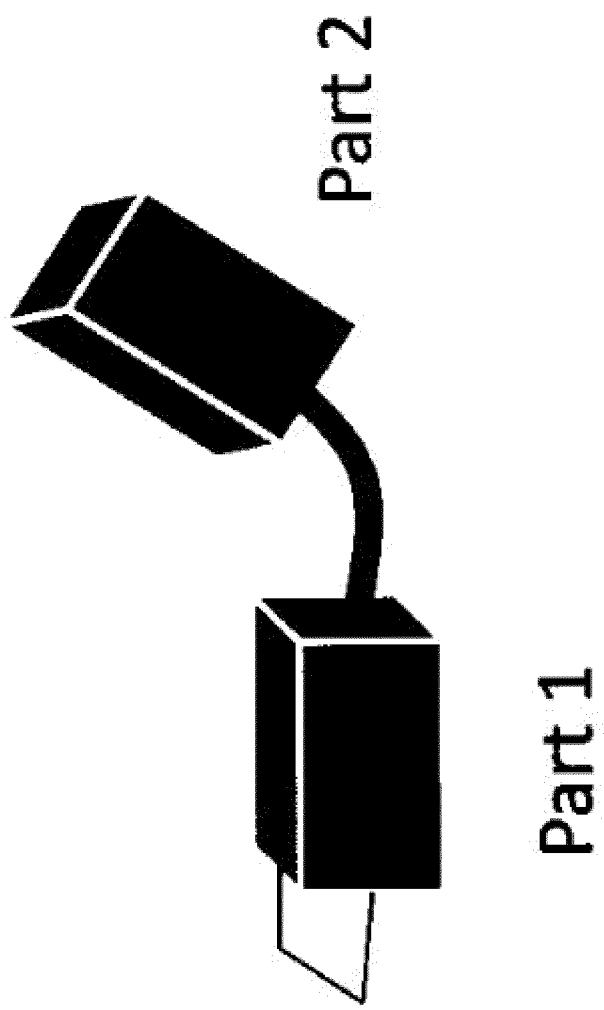
FIG. 39 depicts one embodiment of an articulated arm for connecting a casing of some of the present systems to a computing device.

The first aspect of the invention is a means to easily orientate the device towards the user. Methods exist for this, including cradles and other mechanical orientating assemblies. However these are bulky and not easily carried by a user. We have developed a method that allows the orientation of the device to be adjusted and then maintained, even while the device is rigidly plugged into a USB or other socket of a computer. One preferred means we use to perform this is to articulate the device into two parts. The first part contains at least the USB (or other) plug and the second part contains at least the optical component, as shown in FIG. 39. These two parts are connected by an assembly that allows changes in orientation between the two parts but such that the orientation stays fixed once manipulated by the user to an appropriate position. One preferred way of achieving this assembly is a stiff wire assembly, wherein the wire can be bent and then it stays in a particular position as shown in FIG. 39. Other mechanisms such as a ball-and-socket joint can be used also. A second optional aspect of the invention is to have a retractable cable between the two parts of the device, thereby allowing the device to be manually pulled towards the user, or clipped onto the screen of a laptop for example.

A further aspect of the invention relates to improving the user experience while enhancing performance at the same time. More specifically, many biometric iris devices have a mirror on them to guide the user towards them. We have found that devices where such centering mechanisms have the approximate size of the distance between the eyes (approximately 5-7 cm, "Variation and extrema of human interpupillary distance", Neil A Dodgson, Proc. SPIE Vol. 5291, Stereoscopic Displays and Virtual Reality Systems XI, 19-22 Jan. 2004, San Jose, Calif., ISSN 0277-786x, pp 36-46), and where the distance to the device is at least 50 cm, then a user is typically able to center themselves in front of the device. However, we have found that as the device gets smaller than the eye separation in size, and as the distance to the device decreases to 50 cm or less, then for a device used by a user (as oppose to an operator), then an effect resulting from ocular dominance becomes very typical. Approximately ⅔s of the population has ocular dominance (or eyedness) in the right eye, and the remaining ⅓rd have ocular dominance in the left eye (Chaurasia B D, Mathur B B (1976). "Eyedness". Acta Anat (Basel) 96 (2): 301-5). Under the conditions just described, then the user naturally begins to bring the device not towards the middle of the face, but towards one eye or the other depending on their ocular dominance. The user experience can be very confusing therefore since the feedback from the mirror is encouraging the user to center themselves, but the natural human response due to the ocular dominance is to do exactly the opposite.

Rather than overcoming ocular dominance, we take advantage of it in our invention. We do this in two parts: First, we still use a centering device such as a mirror that a user can use for feedback (other centering mechanisms such as an inverted cone with different colored circles in the cone can also be used). In the case of the mirror, we actually reduce its size so that it is impossible for two eyes to appear in the field of view and therefore confuse the user. In the case of a hand-held device, then the length of the arm limits the distance of the device from the user. With these parameters we have found that a mirrored surface of 0.5 cm-5 cm in diameter depending on the device achieves this purpose. The second component of this aspect of the invention is that we choose a lens and imager such that even though the user is holding up the device centered on one eye, then we are sure to capture imagery of the second eye even though the device is not even in front of it. Therefore while the user believes that the device is acquiring data only from one eye, in fact data is being acquired from the second eye also. There are many means for detecting two eyes from a single acquired image. For example, the specular reflections of an illuminator reflected off the cornea can be detected in the image and used to mark the locations of the eyes.

Figure 40:
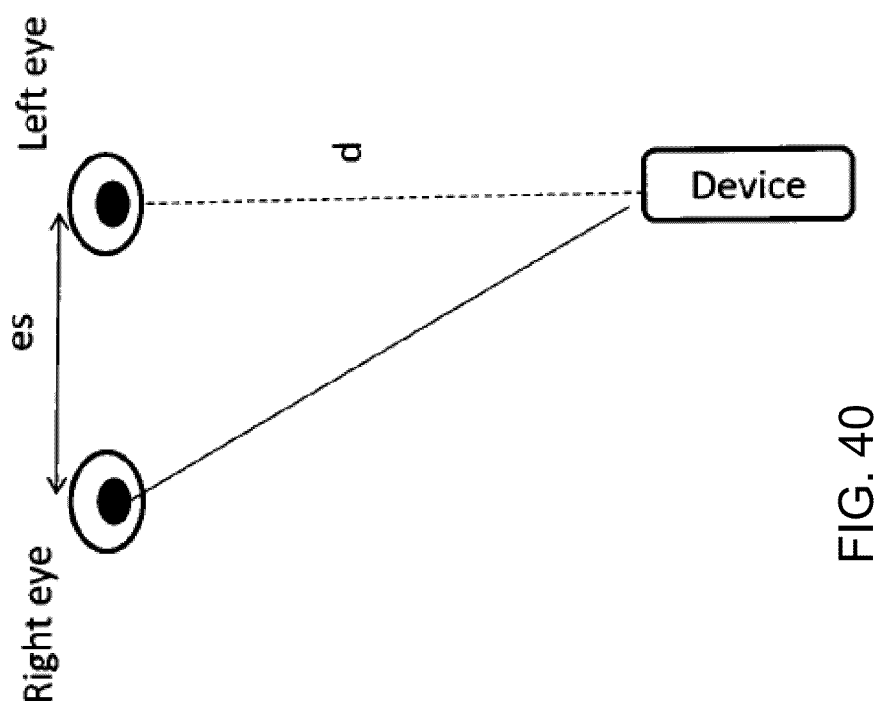
FIGS. 40-42 depict embodiments of a system using a mirror as a centering mechanism for a user with ocular dominance in either the left or right eye.
Figure 41:
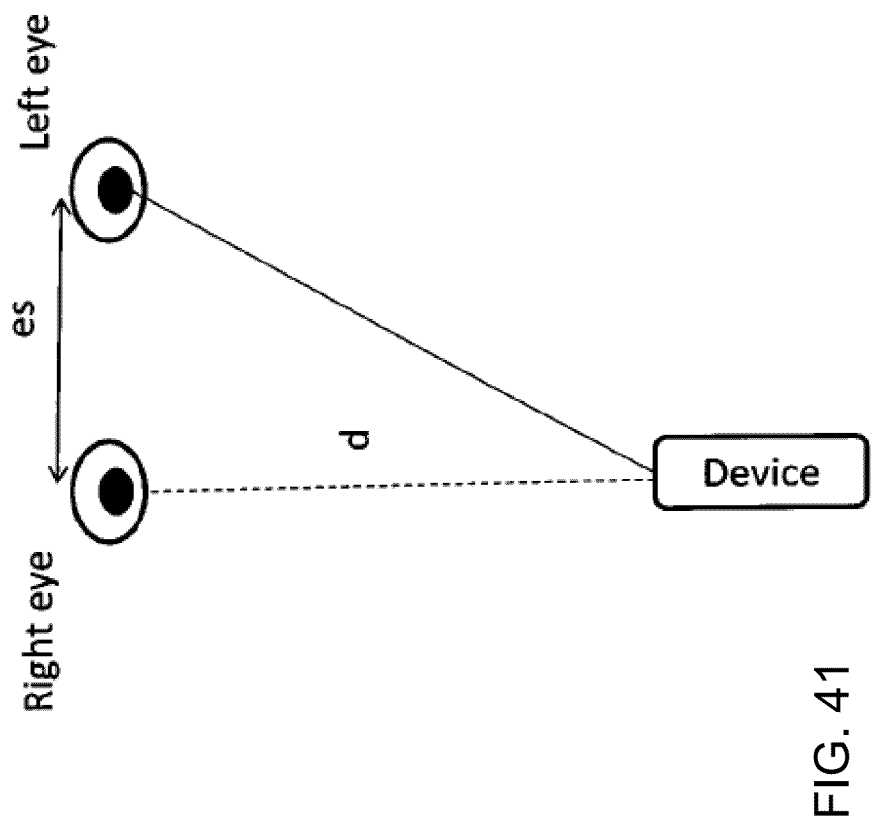
Figure 42:
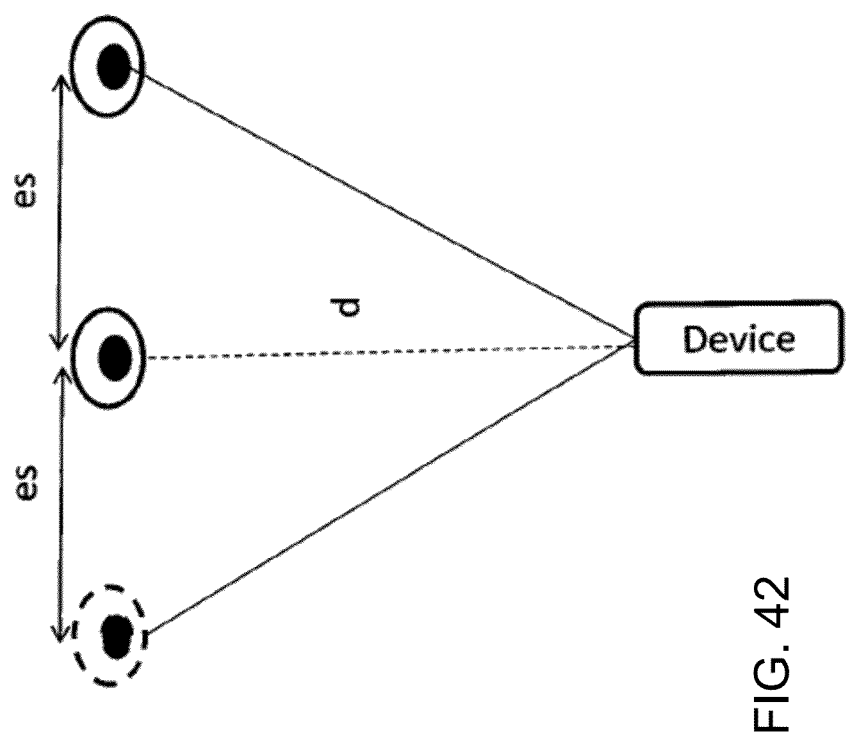
Figure 43:
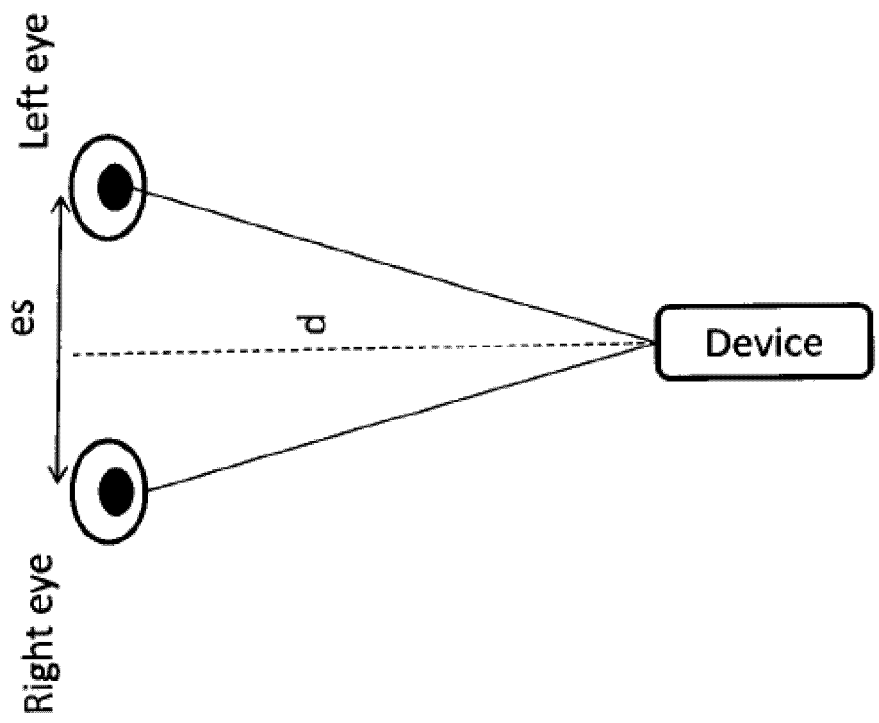
FIG. 43 depicts one embodiment of a system using a mirror as a centering mechanism for a user where ocular dominance is not assumed.

FIG. 40 shows the geometry of such an approach that uses a mirror as a centering mechanism for a user with ocular dominance in the left eye. FIG. 41 shows the same geometry for a user with ocular dominance in the right eye. FIG. 42 shows the minimal field of view necessary to ensure that both eyes appear in the field of view of the camera regardless of whether the user has right or left-eye dominance. The equation governing this minimum field of view is: FOV_min=2*a Tan(es/d), where es is the eye-spacing and d is the distance from the camera, as shown in FIG. 42. By contrast, if ocular dominance is not assumed and the device is placed between the eyes of the user, then the FOV_min=2*a Tan((es/2)/d) as shown in FIG. 43. Therefore our invention requires a larger field of view than approaches that do not consider ocular dominance, but the device is much easier and more intuitive to use with no confusion for the user. Since it is assured by the invention that data from two eyes can be captured, then recognition time can be reduced and accuracy can be improved since more iris data is available for analysis.

Figure 44:
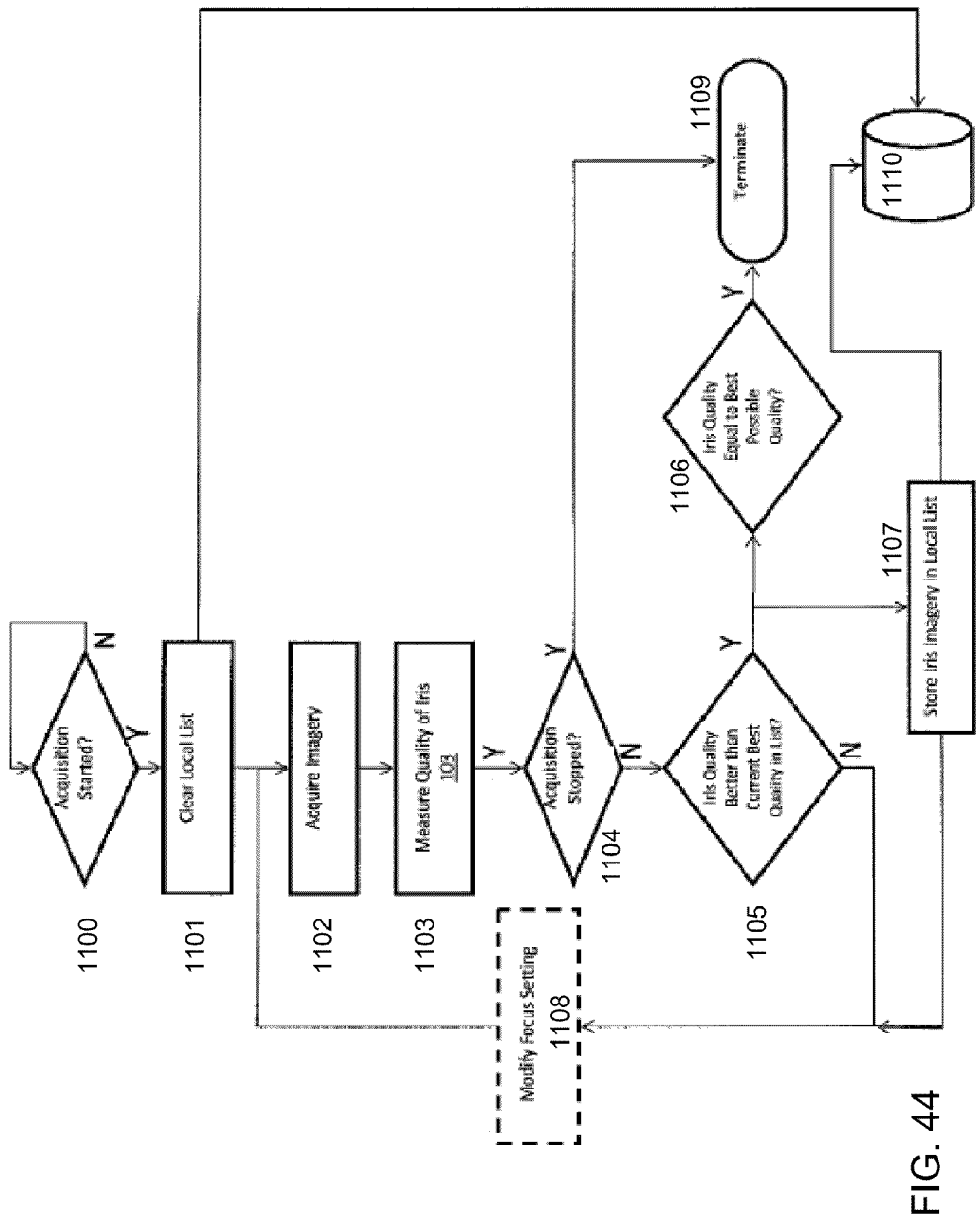
FIG. 44 depicts one embodiment of a method for acquisition of iris imagery.

While the present systems and methods are capable of many embodiments, only a few illustrative embodiments are described herein. Referring first to FIG. 44 illustrating a process flow sheet according to the invention, the process begins with a module 1100 that determines whether Acquisition for a particular subject should be started. This module 1100 may comprise several components depending on the specific application. For example the module may consist of a motion detector module, or a trigger that a previous subject has successfully performed a transaction with the system.

Upon initiating the acquisition, a local list of successively better images from the prior subject is cleared 1101 in preparation for the next subject. An image is then acquired 1102 using a camera system. A camera system is used that can either capture images synchronously at a constant rate, or asynchronously on request by a computer-controlled trigger signal. As discussed later, the camera may be operated at a variable acquisition rate depending on the results of previous processing.

A Quality Metric module comprising, for example, one or more of the following sub-modules: face detector, eye detector, focus measurement, iris area detector is used 1103 to measure the quality of each acquired image in sequence when sufficient computing capacity is available but not necessarily simultaneously with image acquisition. As discussed later, one or all of these modules may be performed at a particular time instant depending on the results of previous processing. The quality analysis and selection system of Martin et al in US 2008/0075335, supra, which is hereby incorporated by reference in its entirety, is one suitable Quality Metric system 1103 for the purposes of the current invention, with the additional feature of the present invention wherein only the best or a small, limited number of the highest quality of the acquired images is stored in memory.

An Acquisition Stopped module 1104 is to perform an Acquisition Stopped routine. This module 1104 ensures that the overall process is not being performed unnecessarily if, for example; the subject has walked away without any data being acquired. The Acquisition Stopped module may consist of a time-out counter that compares to a threshold the difference between the current time and the time that the Acquisition process was started. The process for a particular subject can be terminated 1109 or the last image can be stored 1107 if a better 1103 image than the best quality image stored at 1110 is calculated.

A Comparator module 1105 then compares the results of the Quality Metric Module with the results stored in a Local List in storage module 1110. In the first iteration of the process, there will be no data in the Local List in storage module 1110. However, after several iterations, some data may be present within the Local List 1110. If the results of the Quality Metric Module 1103 are greater than any of those on the Local List 1110, then the imagery data is stored on the Local List, Storage may comprise appending the imagery data to the Local List 1110, or may comprise replacing 1107 imagery data on the Local List that has a lower Quality Metric 1103 value.

Step 1108 is optional, as indicated by the box shown with broken lines. In certain embodiments where step 1108 is absent, additional imagery is acquired automatically without changing focus values but is rather acquired at a fixed focus, the quality of imagery depending on the exact location of a moving subject within the capture volume at the time successive images are acquired. In certain other embodiments when module 1108 is present, the focus setting of the camera acquisition system is independently modified prior to acquiring the next image. Several methods for modifying the focus setting can be employed as discussed later.

After the focus has been modified, then imagery is once again acquired 1102 in the next iteration of the process. The process continues until 1109 either the timeout condition described above occurs, or the Quality Metric 1103 exceeds a value. In some embodiments, images are acquired and selected until a biometric match is found, or a probability of a correct match or identification is met. In certain embodiments, images are acquired and selected until a predefined number of images have been selected, e.g., that exceeds a certain quality threshold.

Figure 45:
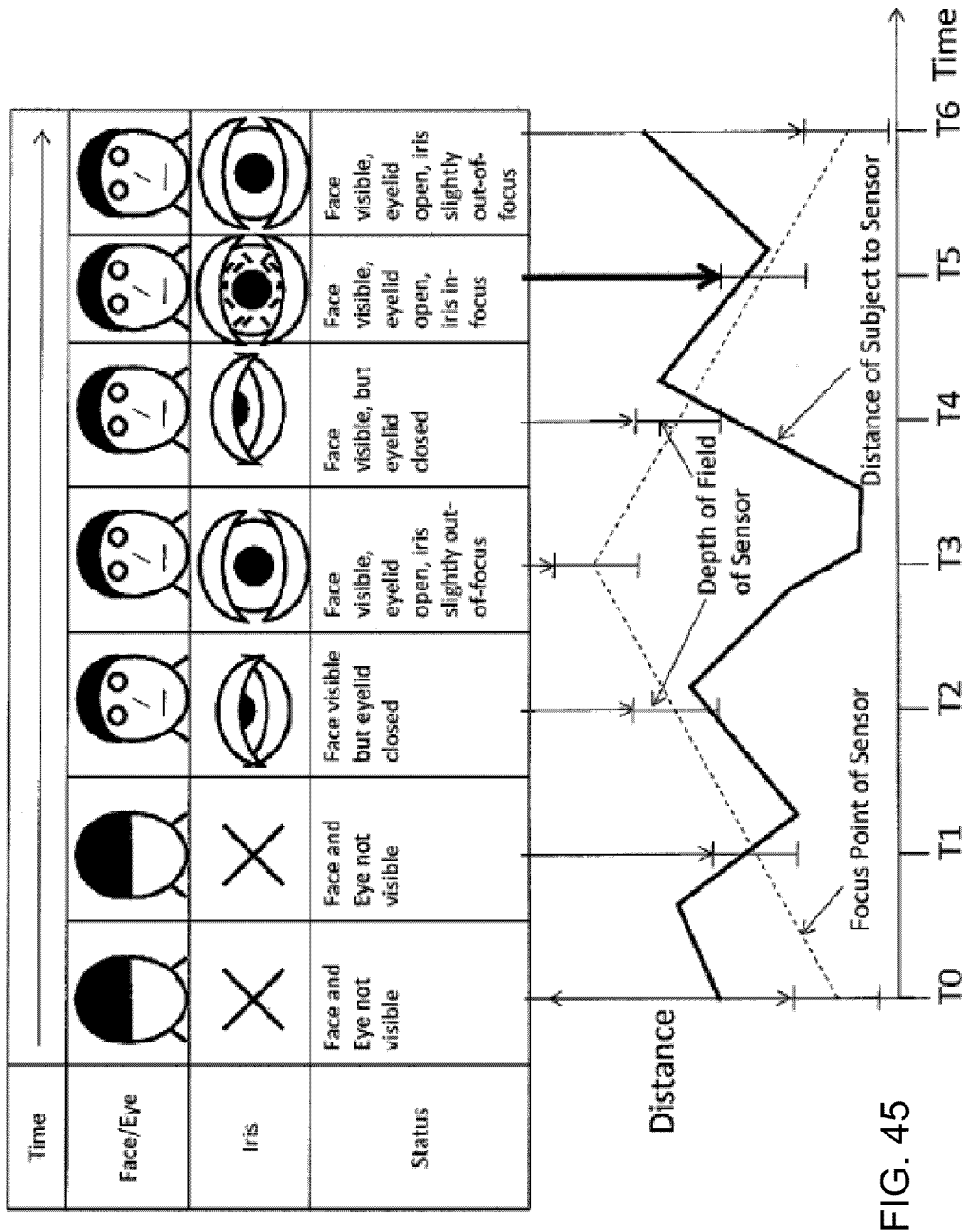
FIGS. 45-48 depicts embodiments of the relationship between the focus point/pattern of a sensor, distance between a moving subject and the sensor, and images acquired over time.

Referring now to FIG. 45 the top illustration shows the disposition of an unconstrained subject over a period of time at times To through T6, showing that the subject may turn his head, or blink, for example. The solid, dark line in the bottom of FIG. 45 shows the disposition of the subject's distance from the camera acquisition system. Note that the subject is moving closer then further from the camera sensor in a random fashion due to their relaxed disposition or inability to remain exactly stationary. The dotted line shows the disposition of the Focus Setting position at different time instants. In this case, the Focus Setting has been set to follow a sawtooth waveform over time. The small vertical bars on the dotted line indicate the depth of field of the sensor. If the depth of the subject intersects any point within the small vertical bar, then the subject is in focus. The "Status" row at the top describes the status of the subject with respect to the image acquisition system. For example, at T=T0, the subject's head is turned and no face is visible. At T=T2, the subject's depth intersects with the depth of field of the particular focus setting at that time, however the subject's eyelid happens to be closed at that point in time. At T=T3 on the other hand, the subject's eye is present, the eye is at least partially open so that the resultant Quality Metric has a finite value, albeit a lower than optimal value since the image is slightly out of focus. The imagery at T=T3 is therefore placed on the Local List. At T=T5, the subject's eye is present, the eye is at least partially open so that the resultant Quality Metric has a finite value, and the subject's depth intersects with the depth of field of the particular focus setting at that time so that the Quality Metric has a higher value compared to that of the image that is already on the Local List, and therefore the image at T=T5 is either placed on the Local List or replaces the existing image on the Local List depending on the particular embodiment of the invention.

Figure 46:
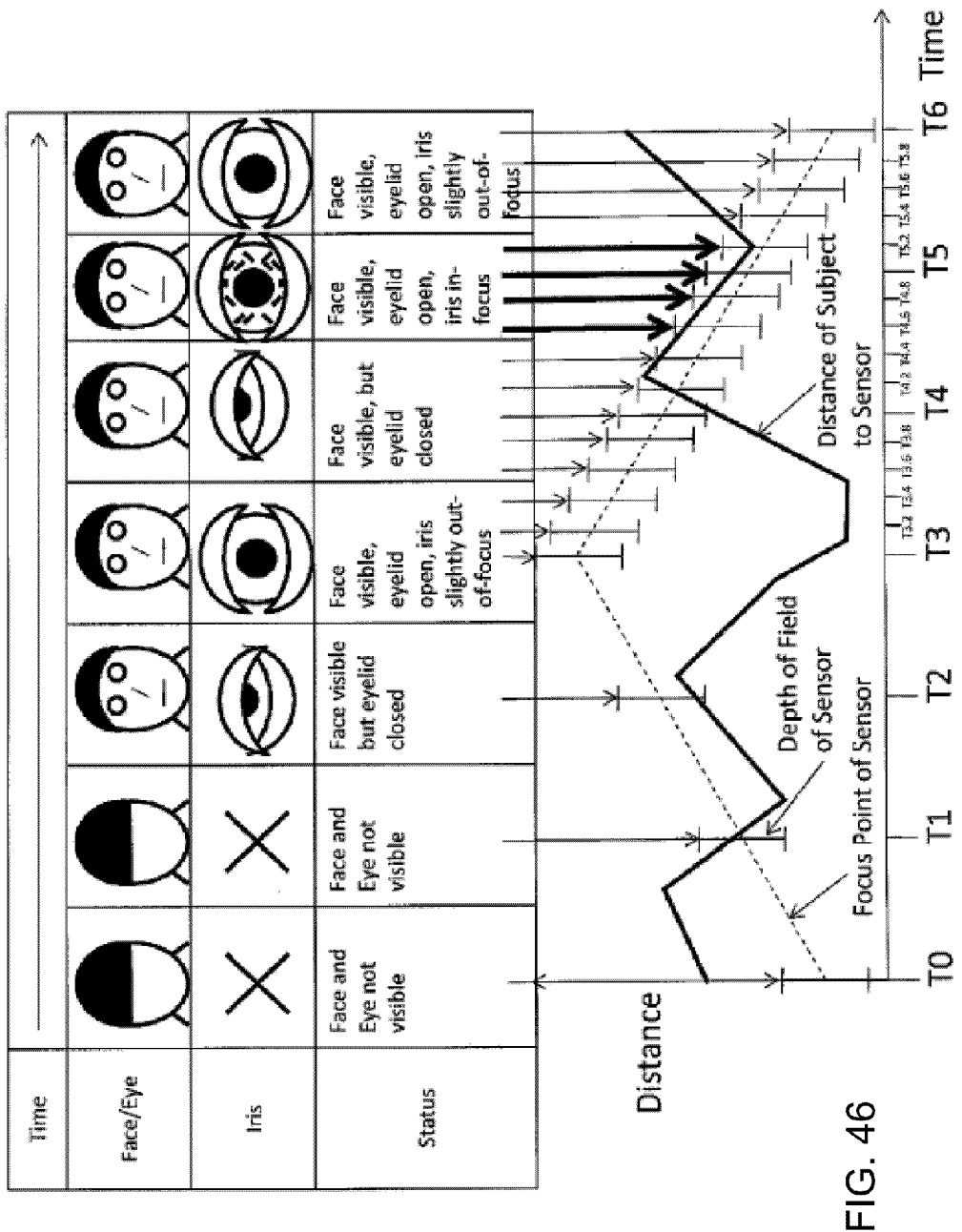

FIG. 46 shows another embodiment of the invention with a different focus setting routine. The subject's disposition is as in the previous example, but the camera acquisition module has the capability of performing rapid data acquisition over short time periods, upon certain conditions. Rapid data acquisition is not performed all the time since it is prevented by limitations in bandwidth and processing speed. In the embodiment shown in FIG. 46, the selected conditions for performing short-duration rapid data collection for a fixed time period (in this case from T=T3 to T=T6 is the detection of a face, an eye, an iris that is open, but blurred. If most of the criteria for successful acquisition have been met, then there are only very few additional criteria that need to change before valid iris data can be acquired. It is therefore more probable than at other time instants that valid iris data may soon appear. The rate of data acquisition is therefore increased in order to be ready to capture more iris data than would have otherwise been captured.

Referring now to FIG. 46, the thick vertical lines around T=T5 shows that 4 images were acquired around this time period during the rapid acquisition mode, rather than just 1 image in the prior embodiment.

Figure 47:
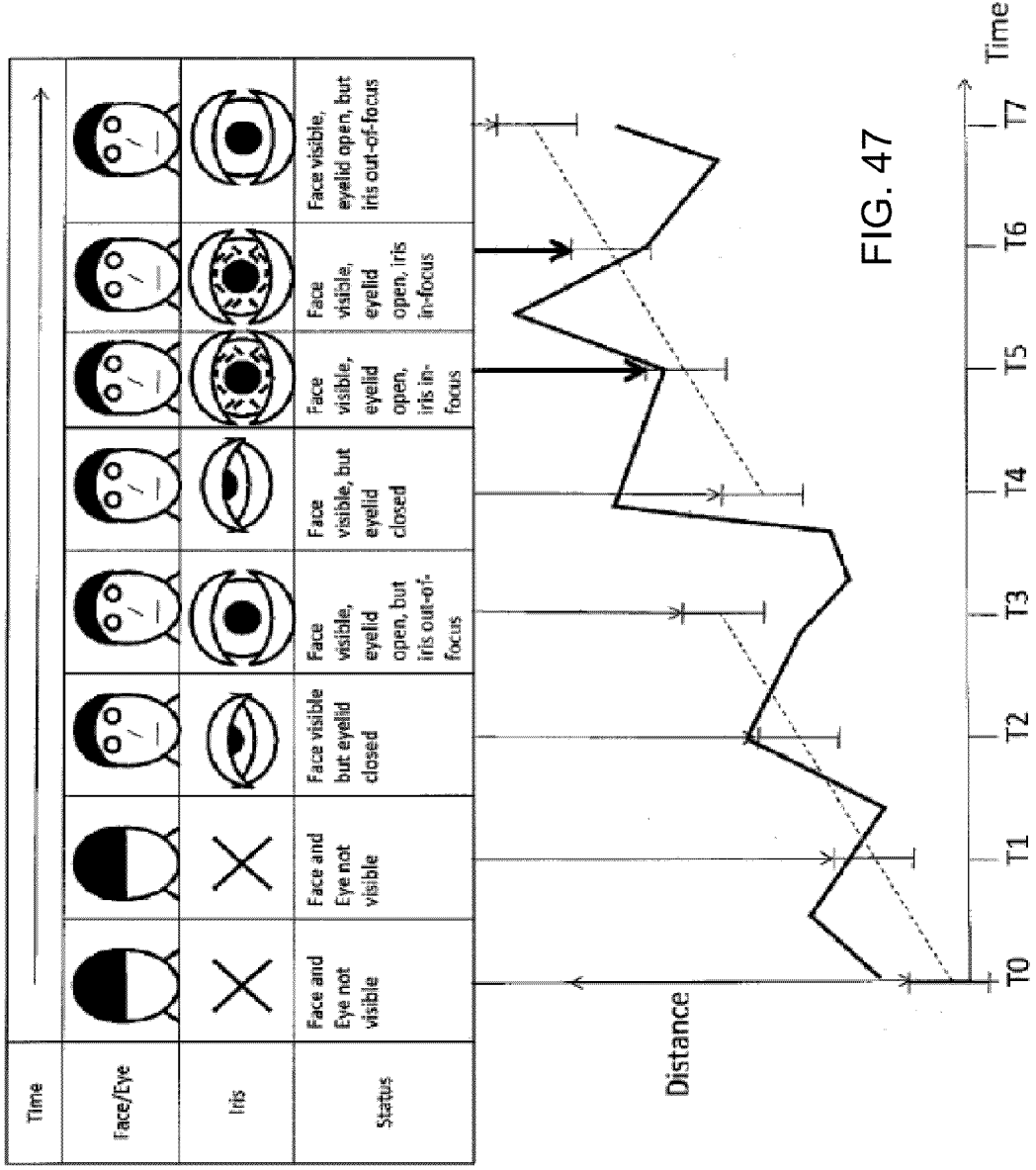
Figure 48:
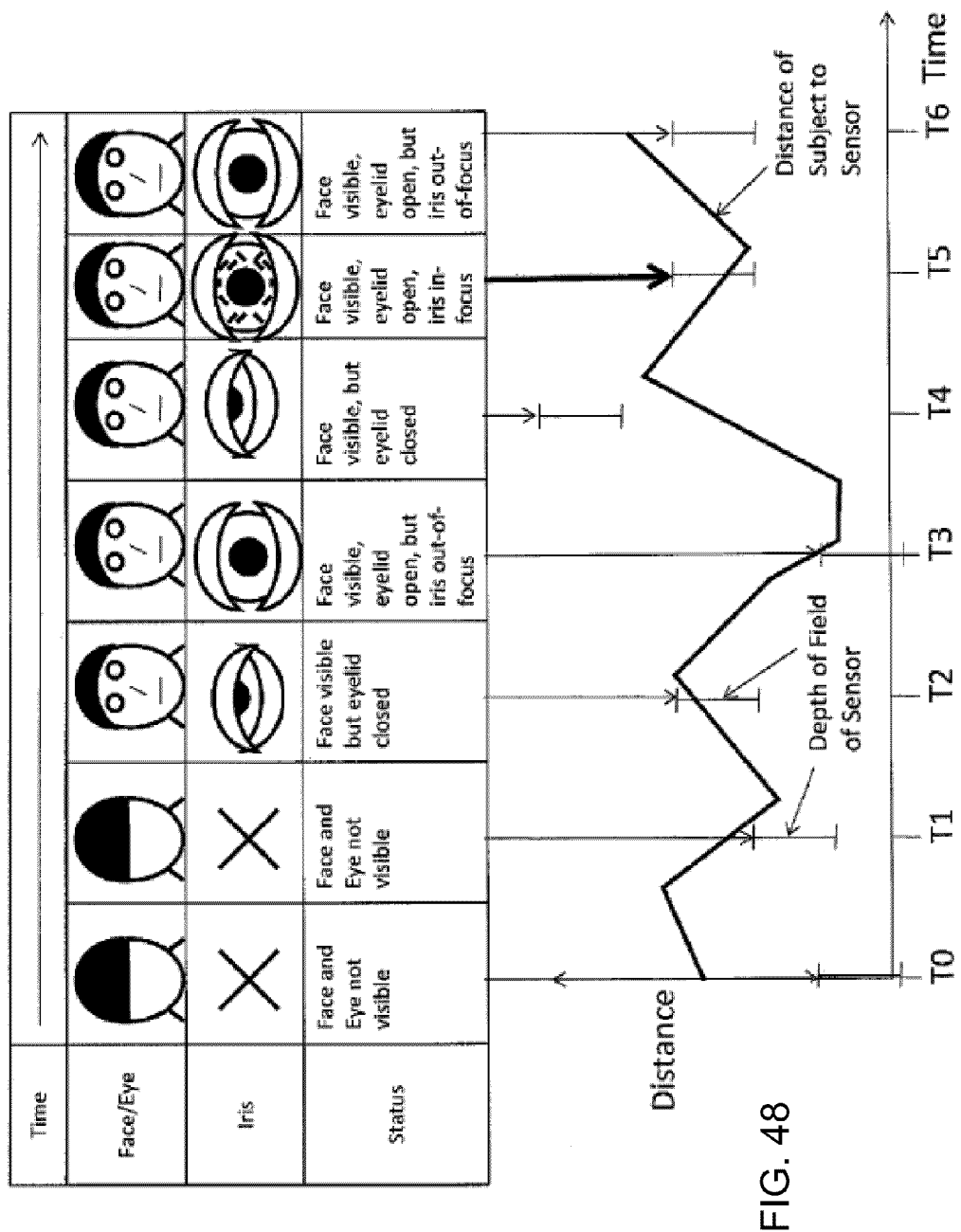

Referring to FIG. 47, the subject is moving generally towards the camera, in addition to random movement. In this case the focus setting is a combination of an auto-focus value computed from the average focus of prior settings, as well as a sawtooth waveform as described in the first embodiment. In this case, valid iris images are stored on the Local List at T=T3, T=T5 and T=T6.

Figure 49:
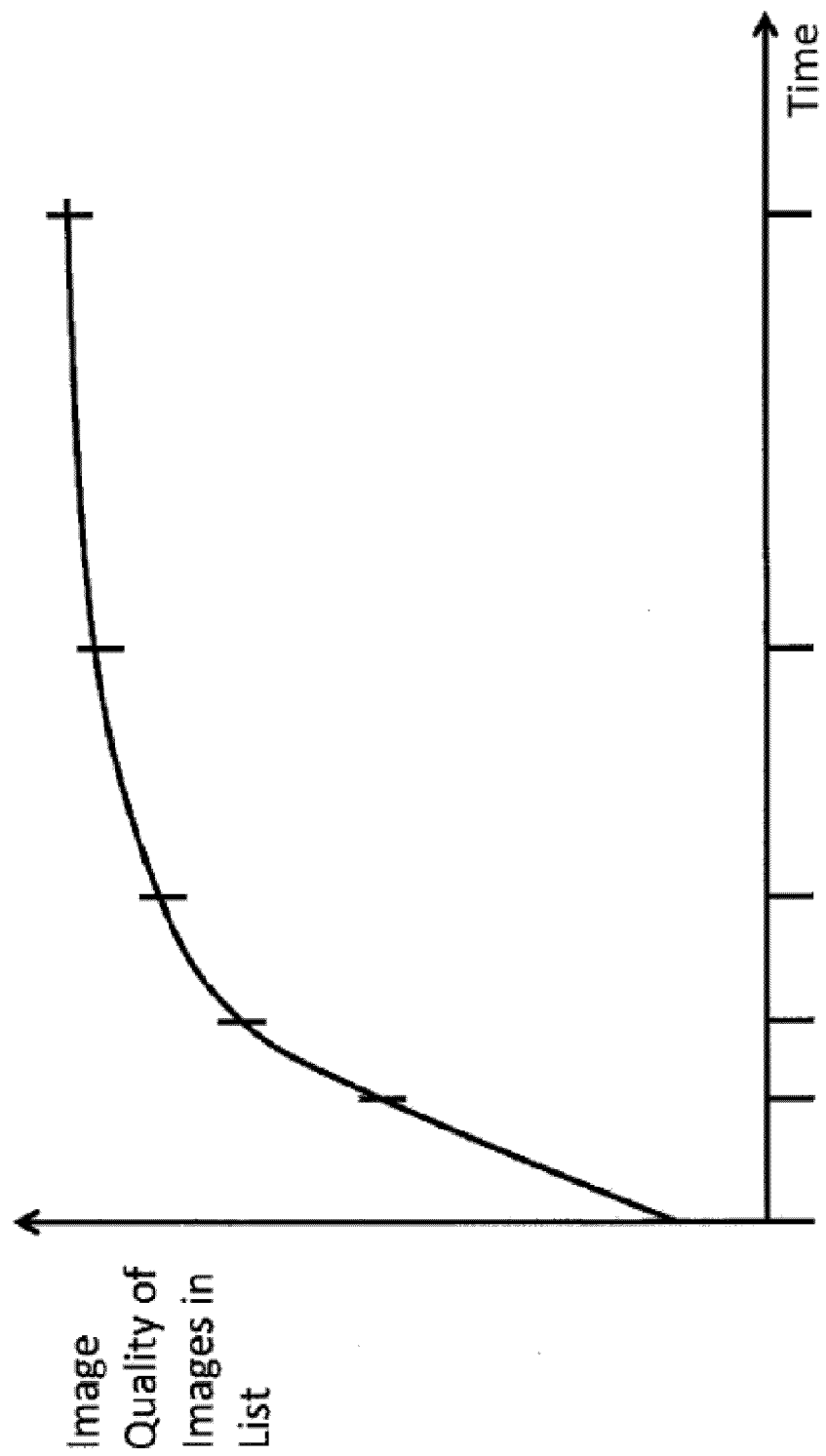
FIG. 49 is a graphical representation of improving quality of iris images stored and/or selected over time, which can result in a reduction in the number of images stored and/or processed.

FIG. 49 is a graph showing on the Y-Axis the Quality Metric value of images as they are placed on the Local List over a short time period. Typically, imagery is typically placed on the list rapidly, but then as more data is placed on the list it becomes more difficult and therefore takes longer for new imagery to exceed the existing Quality Metrics on the list. An example Quality Metric is Q=F (A+delta), where F is a focus measure where high values of F indicate more focused imagery and A is the estimated area of the iris. Various known, alternative methods for segmenting the iris and extracting the area and quantifying focus can be used.

The method is highly effective in many respects. A first advantage of the invention is if the disposition of the subject is immediately amenable to successful data acquisition (e.g. eyes are open and their face is facing the system), then the system will acquire iris imagery very rapidly. There are many methods for detecting the presence of an eye. For example, the Hough Transform disclosed in U.S. Pat. No. 3,069,654 can be configured to locate circular segments of the eye due to the iris/sclera boundary and the pupil/iris boundary.

However, if the subject is fidgeting or unable to remain stationary, or is distracted by baggage or children for example, then the acquisition system will still acquire imagery, although it might take a slightly longer period of time. However, the acquisition time for an amenable subject will not be penalized by the system's delays in acquiring data in the case of a less amenable subject. This is crucial when subject throughput is considered. This is to be contrasted with systems that may acquire and store a large number of images and then perform processing on the images to select imagery.

A second advantage of the invention is the ability to acquire successively better iris imagery. In the current art, iris image acquisition systems typically have resulted in the output of one image of the iris deemed to have a quality suitable for matching, usually exceeding a threshold. If such an image is not found, then no iris data is captured. The problem with the current art is that there are some applications when there will not be a second chance to acquire better data since the subject has gone elsewhere or is fed up with using the system. Ironically, however, the iris imagery they presented may have had plenty of information for the particular application at hand. For example, if the image acquisition system is to be used to gain entry into a house with only 100 subjects, then some of the iris imagery acquired earlier in the acquisition process may be sufficient.

A third advantage of the invention is the efficient use of memory, which is significant especially when an embedded device is used. The Local List contains only iris imagery that is successively of better quality than the prior imagery, and does not contain the imagery that was originally acquired. In addition, depending on the application, the Local List can comprise a single image which is replaced each time imagery of a better quality is detected. After processing is complete, then the resultant image remaining in the Local List is the imagery acquired of the best quality.

In one embodiment, the invention obtains in-focus images by using a focus controller component that controls the lens to focus at successively different points within a focus range, such scan control performed without any input from measurement of whether the image is in focus or out of focus, be it based from measurements of the image or other distance metrics to the subject. In terms of focus scan speed and how it relates to frame rate, exposure time these relationships and related algorithms are known to those skilled in this art.

Even when a subject is trying to stand still, there will be residual motion. The system in some embodiments can increase or decrease the rate of image capture at different focuses in view of the degree of motion of the subject.

The system acquires a varying number of images, to account for the fact that in some cases we may acquire a good image on the first image acquisition, but in other cases may have to wait for 10 or 20 image acquisitions or more. If the system simply fixed the number of image acquisitions to be 10 or 20, then we would dramatically slow down the average time it takes to use the device, and therefore reduce the throughput of people using the device, since the number of image acquisitions acquired would be set at the worst case, rather than being adaptive based on the quality of the iris. It may not be good enough to have the focus set at the correct focal distance opportunistically since, for example, the subject may blink or turn away even though the image is in focus.

If 10 or 20 or more images are being acquired, storing them can take up a lot of memory, which can be expensive in an embedded device. The system of the invention successively checks whether the iris image quality is better than the best iris image stored previously and only in that case does the system store it. Alternatively the system can overwrite the best iris image acquired so far to replace it with the better image. In this way, the system always has the best possible iris image stored without having to use extensive memory. If the subject turns away and the system loses its opportunity to ever again acquire iris data of a subject, the best possible image, even if not of high quality, will be stored and such image may have sufficient quality for biometric identification under the circumstances.

In addition to the area to which the camera is pointed, we also can control a focus control system such that a capture volume is swept through. Unlike autofocus which requires settling time, and many discontinuous stop/start steps that eventually can wear down components and can take time to respond, we simply sweep through a focus volume rapidly, in order to opportunistically acquire biometric imagery.

In certain embodiments, the biometric or image acquisition system may comprise a device, such as an embedded device, that may be portable, mobile, compact, lightweight and/or attachable to a computer or other computing device. The device may incorporate various design aspects that improves performance in embedded applications such as biometric acquisition and/or processing. Some of these design aspects may also make the device portable, mobile, compact, lightweight and/or suitable for connecting to a computing device.

For example, a first aspect may include a positioning system that enables simple and/or rapid positioning system and/or alignment of a user's eye with a sensor. An illuminator may enable acquisition of well-illuminated images of an iris of the user. The positioning system and/or illuminator may improve performance by enabling acquisition of non-foreshortened and/or non-occluded images of a user's iris. Another aspect may include means whereby a single compact sensor can be used to acquire both high quality images of a scene under visible illumination as well as high quality images of irises under infra-red illumination. Yet another aspect may relate to optimizing processing inside an embedded image acquisition or processing device, as well as optimizing the interface between the device and external devices in order to improve usage of limited resources available, such as memory and power. These aspects are discussed in detail below and elsewhere in the present disclosure.

In some embodiments, the biometric or image acquisition system includes a positioning system that enables simple and rapid alignment of the user's eye with a camera, which may include one or more illuminators adapted to enable the system to acquire well-illuminated, non-foreshortened and/or non-occluded images of a user's iris. In some contexts, foreshortening may describe acquisition of an image of an iris that significantly deviates from facing directly into an image acquisition sensor, or which is not optimally oriented towards the sensor. For example, foreshortening may have occurred if an image of an iris region is elliptical in shape, rather than circular. In certain contexts, occlusion may refer to blockage or obstruction of an object by another object. For example, an iris may be occluded by an eyelid or eyelashes in an acquired image. An image may show occlusion by a finger that partially covered a sensor and/or an illuminator when the image is captured.

Figure 50:
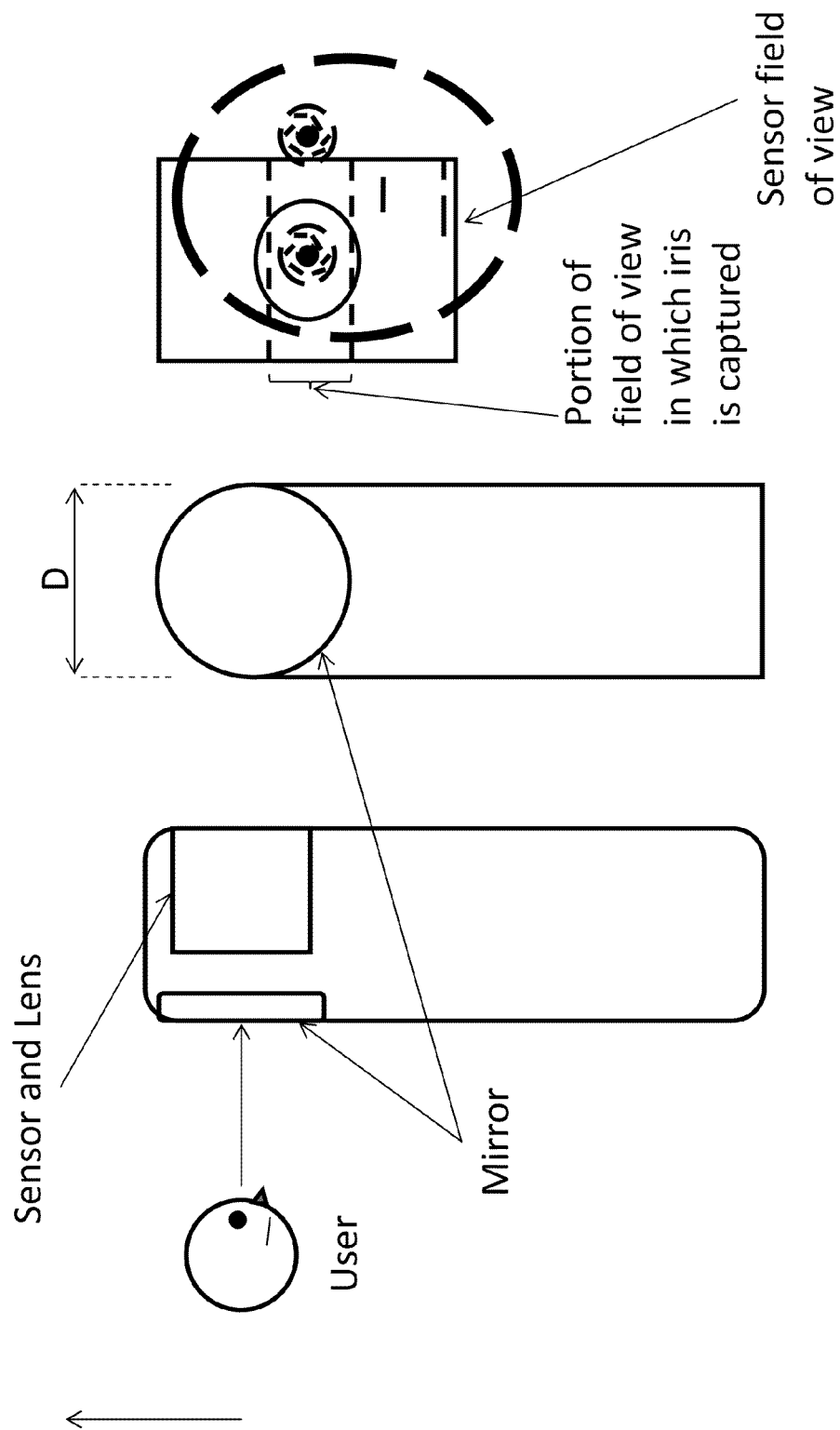
FIG. 50 depicts one embodiment of a system for positioning the user and minimizing foreshortening of acquired iris imagery.

FIG. 50 depicts one embodiment of a system for guiding or positioning the user with respect to the field of view of a sensor. The system may include one or more mirrors positioned proximate to, over or in front of at least a portion of a sensor for image acquisition. Location of the mirror at or near the sensor can allow a user to look at the mirror while looking at or near the sensor. The user may use a reflection from the mirror to guide positioning of user's iris or the image acquisition device relative to the other. The user may use the mirror to center or position an iris reflected off the mirror as feedback or guidance to the user. In some embodiments, the mirror may include markings to identify optimal positioning of an iris' reflection in the mirror, for image acquisition.

In some embodiments, when the mirror and sensor are co-located, such as when the sensor is positioned behind the mirror, the user may look at the mirror and sensor at the same time, perhaps without even realizing that his/her iris is facing the sensor. Thus, images of the iris acquired under such conditions are less likely to be foreshortened. In some embodiments, the mirror may transmit a portion of the light directed into the mirror, to a sensor behind the mirror. The mirror may transmit a portion of the light reflected off an iris to the sensor. In some embodiments, the mirror may be translucent or semi-transparent. In certain embodiments, the mirror may be a one-way mirror, or a cold mirror (e.g., allowing infra-red light to pass, and reflecting visible light).

As discussed earlier, for example in connection with at least FIGS. 25-34, a suitable or optimal size may be determined for a guiding or positioning mirror, to account for ocular dominance in a user. As discussed, a small, compact mirror may counter-intuitively provide a more optimal positioning mechanism than a larger mirror. In some embodiments, the mirror is sized to reflect a single iris or eye of a user back to the user when positioned at a suitable or optimal distance, height and/or orientation relative to the user for image acquisition. The mirror may be sized to exclude a second iris or eye from being reflected back to the user at the same time, when positioned at the suitable or optimal distance, height and/or orientation. In some embodiments, the mirror is sized relative to the size of the sensor, the image acquisition device and/or the field of view of the sensor.

Figure 51:
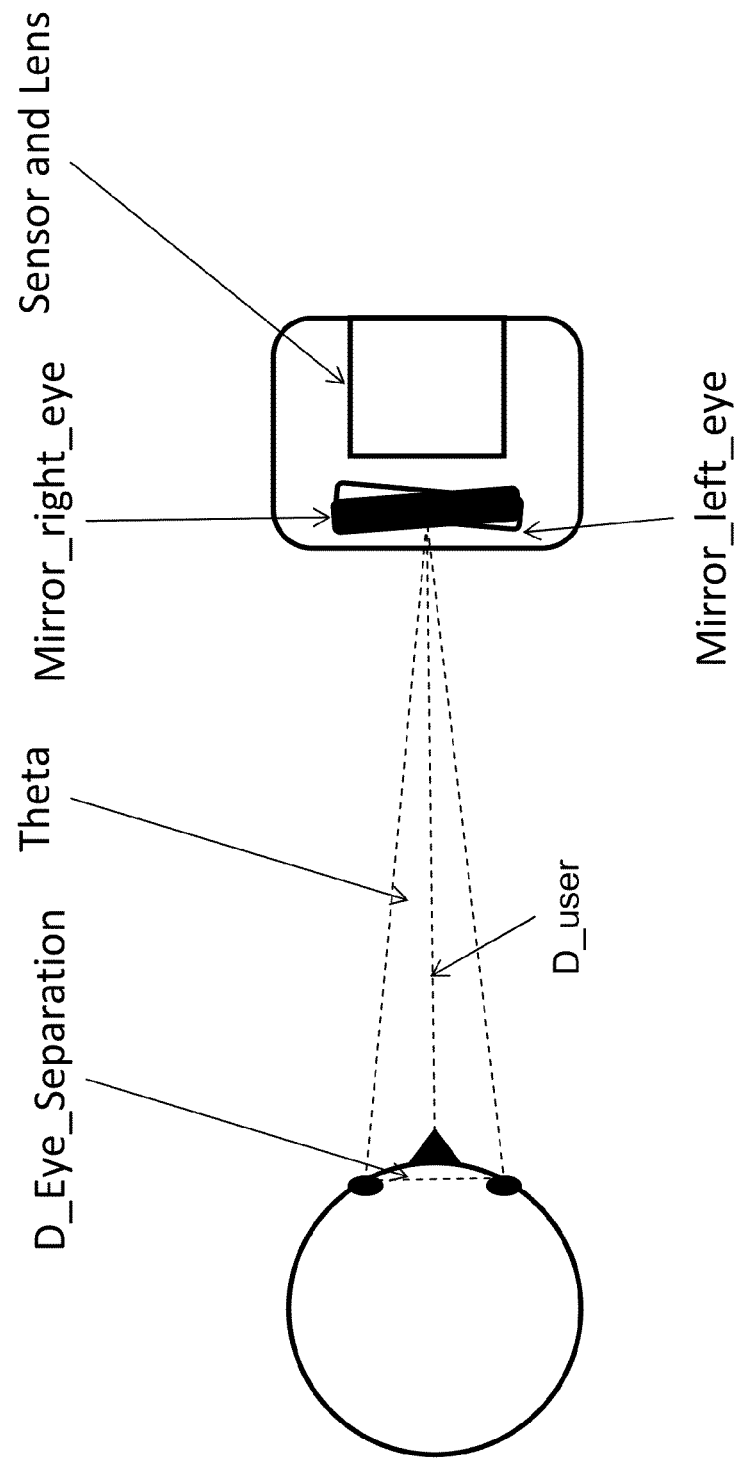
FIG. 51 depicts one embodiment of a system, from a top view, for positioning the user and for minimizing foreshortening of acquired iris imagery.

FIG. 51 depicts an embodiment of the image acquisition device whereby two mirrors are positioned at slightly different orientations and/or locations. In some embodiments, the mirrors may be arranged so that a user can see his/her left and right eye in each mirror respectively, when at a nominal or suitable operating distance, orientation and/or height relative to the device. The configuration of mirrors can act as a mechanism for a user to position the user in depth or distance, e.g., from the sensor of the device. The mirrors can also act as a mechanism to help position or guide the user's orientation, e.g., laterally and/or vertically, such that both the user's left and right eyes are within the field of view of the sensor.

Referring to FIG. 51 again, a top view of the arrangement of two mirrors is shown. One mirror may be positioned at a positive angle with respect to the optical axis of the camera, and a second mirror may be oriented at a substantially equal but negative angle with respect to the optical axis. In one configuration, the angle of the mirrors are selected by theta=a Tan((D_Eye_Separation/2)/D_user), where D_user is the nominal or optimal distance of the user's eyes from the device. D_Eye_Separation may be a typical or nominal eye separation distance of a user (e.g., human user). By way of example, a value for D_user in certain applications may be 15 cm, and a value for D_Eye_Separation may be 6 cm. In another configuration, the angle of the mirrors may be selected by the angle between the virtual position of the eye images behind the device, such that theta=a Tan((D_Eye_Separation/2)/(D_user*2)).

Figure 52:
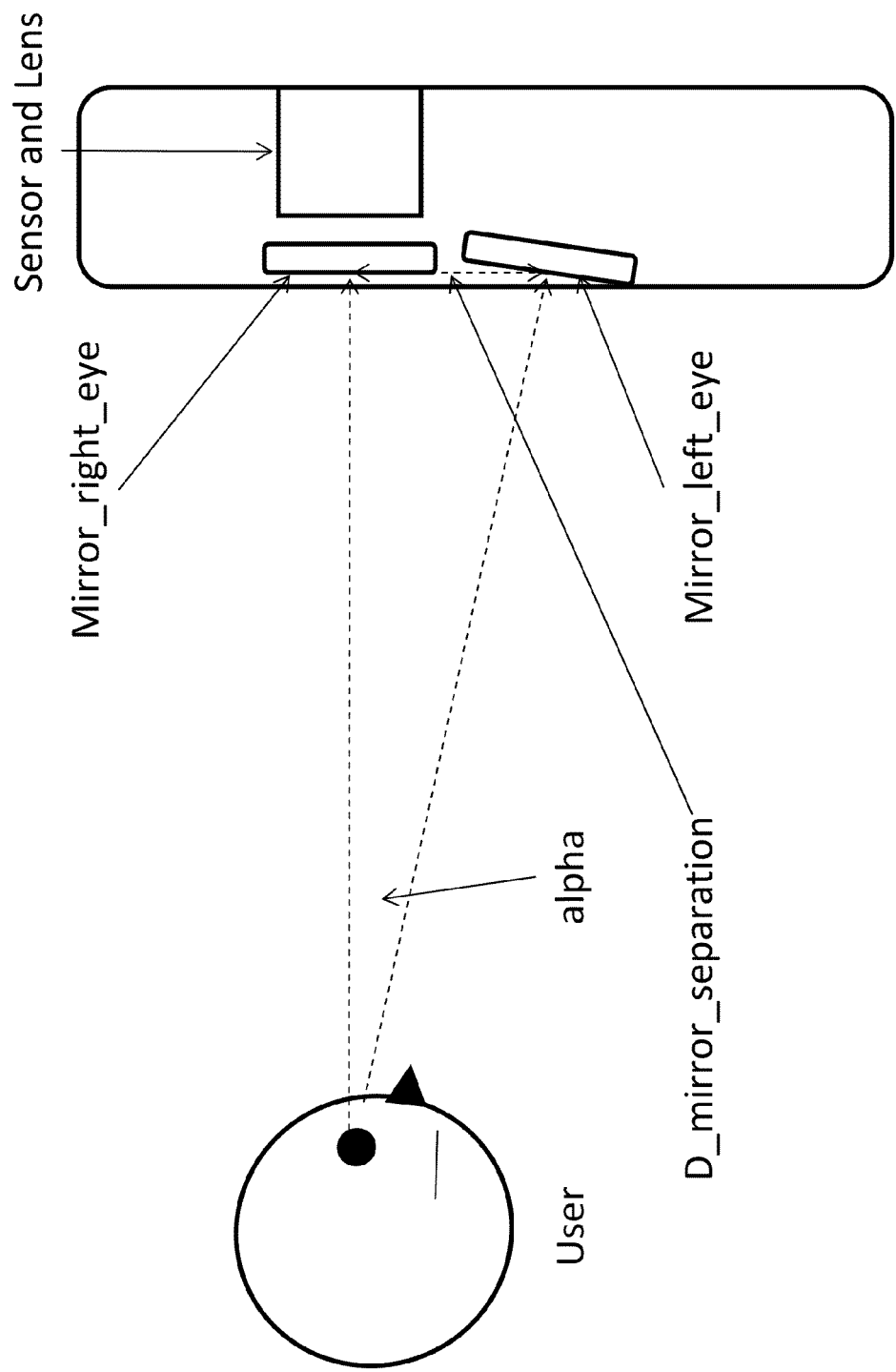
FIG. 52 one embodiment of a system, from a side view, for positioning the user and for minimizing foreshortening of acquired iris imagery.

FIG. 52 shows a configuration of the mirrors in a side or profile view of the device. The bottom mirror may be tilted or oriented about a horizontal axis perpendicular to the optical axis of the mirror, such that the mirror points at a user's eye when located at the nominal or optimal operating distance of the device away from the eye. The angle about this horizontal access may be described as alpha=a Tan(D_mirror_separation/D_user). Although shown in a vertically-stacked arrangement, the two mirrors may be positioned proximate to each other or right next to one another in any direction. The sensor may be arranged behind one or both mirrors, or a portion thereof. In some embodiments, the two mirrors may be replaced by a curved, concave or suitably shaped mirror to reflect an image of both eyes. In some embodiments, the sensor may be located proximate the mirror(s), for example between two mirrors. One or more sensors may be incorporated into the device, for example, a sensor to acquire an image of each iris. In certain embodiments, locating the sensor(s) behind one or both mirrors may result in a more compact configuration for the device.

In addition to, or as an alternative to the positioning mirror(s), an eye finder module may be connected to or incorporated into the device to detect if a subject's eyes are present at the expected regions and guide the user accordingly. For example, the device may audibly alert the user using a loudspeaker, or visually using LEDs or a screen, if the user's eye(s) are positioned incorrectly.

Figure 53:
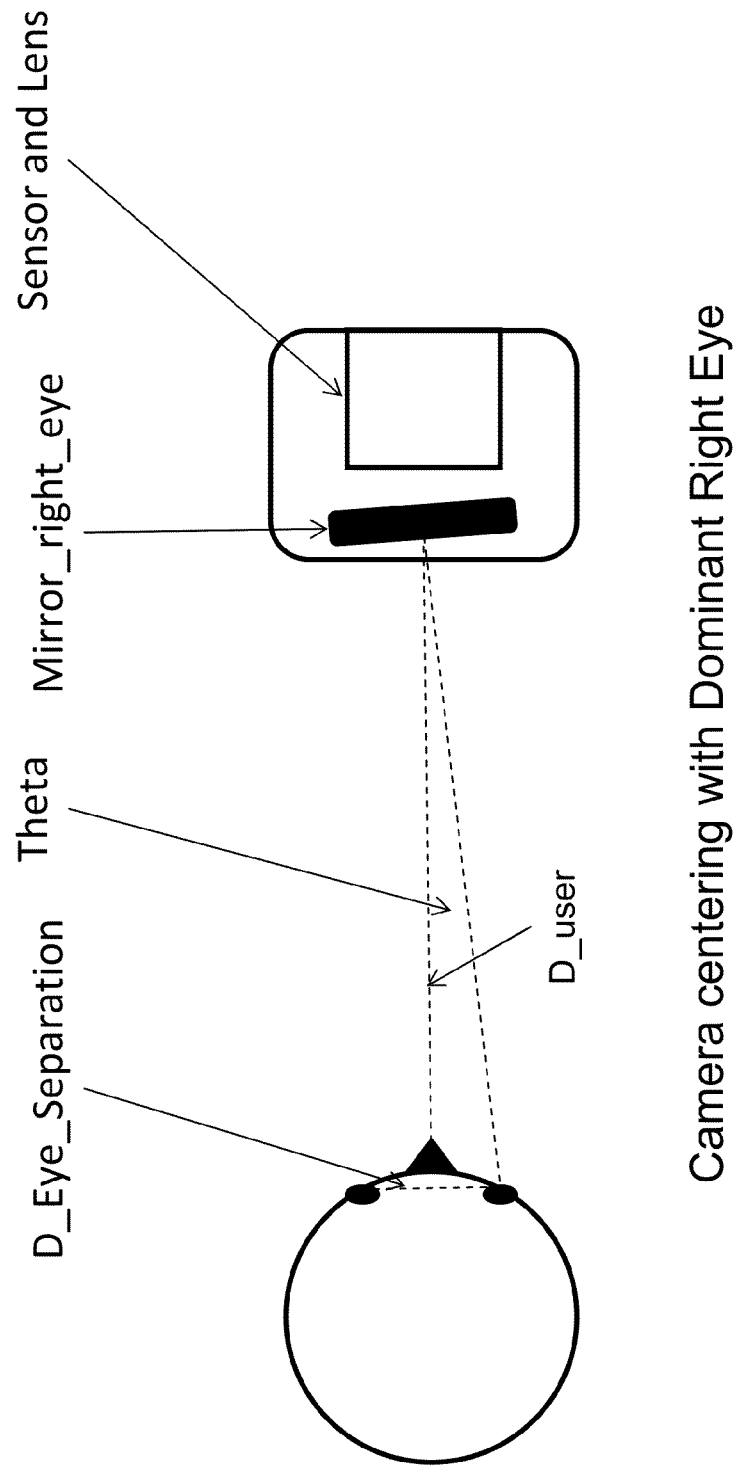
FIG. 53 depicts one embodiment of a system, from a top view, for positioning a right-eyed-dominant user and minimizing foreshortening of acquired iris imagery.

FIG. 53 shows one embodiment of a scheme for centering both eyes of a subject in a field of view of a sensor using one mirror. With only one small mirror for guidance, a user may bring the device up to a single dominant eye. The mirror may be oriented or tilted (e.g., along a horizontal axis) such that for a user with a dominant right eye, the camera sensor may be aligned to acquire imagery of both eyes at an optimal or nominal distance (e.g., D_user), height and/or orientation relative to the device.

Figure 54:
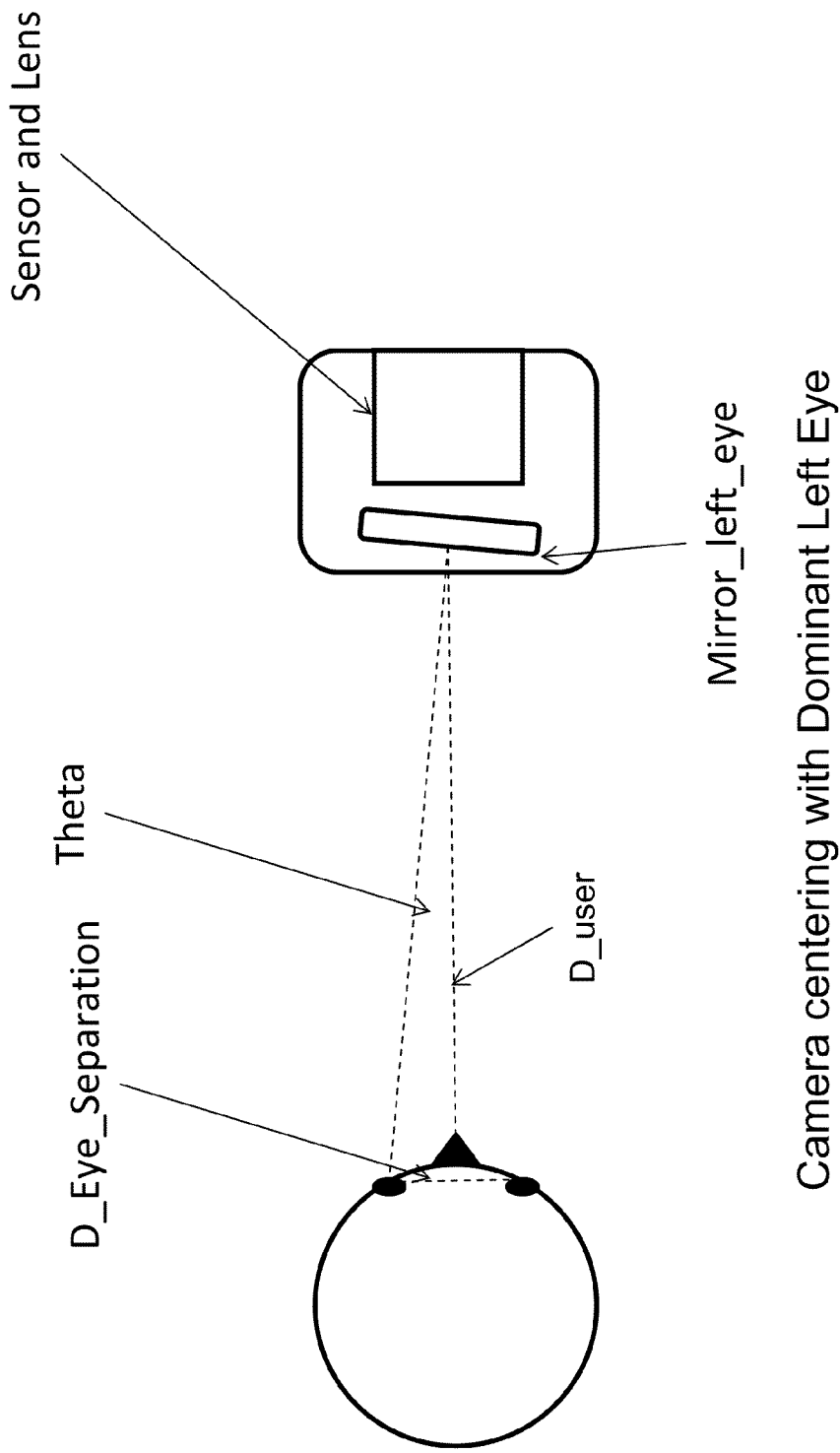
FIG. 54 depicts one embodiment of a system, from a top view, for positioning a left-eyed-dominant user and minimizing foreshortening of acquired iris imagery.

FIG. 54 shows another embodiment of a scheme for centering both eyes of a subject in a field of view of a sensor using one mirror. The mirror may be oriented such that for a user with a dominant left eye, the sensor is aligned to acquire images of both irises at a nominal or optimal user distance from the sensor, mirror and/or device.

Figure 55:
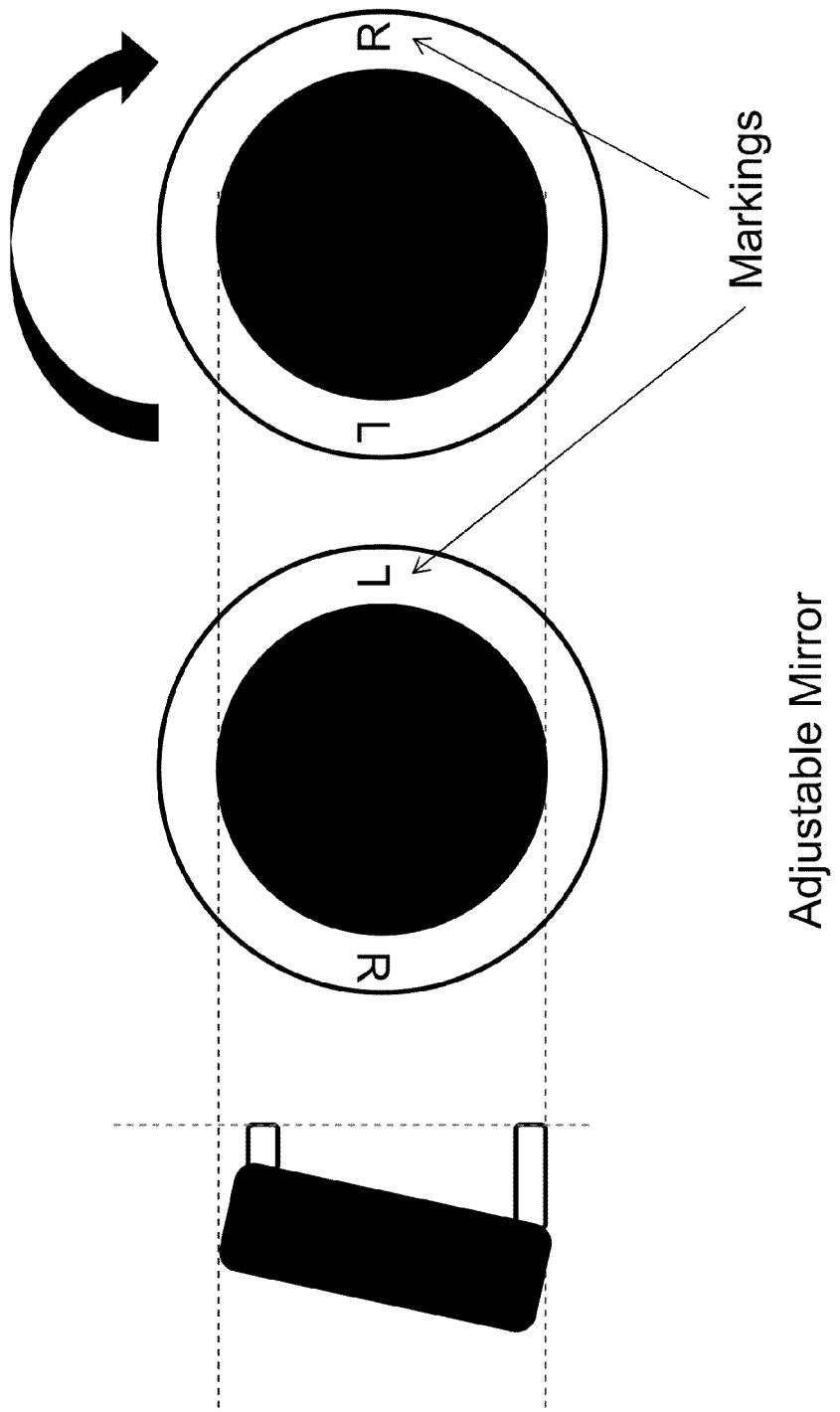
FIG. 55 depicts one embodiment of a mechanism adjusting a mirror depending on whether a user is right-eye dominant or left-eye dominant.

FIG. 55 shows one embodiment of a mirror mount or tilt mechanism. The mirror may be mounted on a tilted mount, so that the mirror is tilted with respect to a casing of the image acquisition device when mounted to the casing, for example. In various embodiments, the mirror may be tilted or oriented towards a dominant eye of the user or subject. In certain embodiments, the mirror may be adjusted to be in at least two positions depending on whether the user is right-eye dominant or left-eye dominant. For example, the mirror may be rotated on the mount, or the mount may be rotated with the mirror, e.g., towards a dominant eye of a subject. Markings on the edge of the mount may indicate the configuration or position of the mount, for example "R" or "L" for right or left-eye dominance systems. In other embodiments, the mirror may be manually or mechanically tilted or switched towards a dominant eye of a user. The mirror may be tilted about a pivot, for example. An advantage of an adjustable mirror orientation is that a single device or mirror may be easily reconfigured for either eye dominance. A single device can be manufactured, and the mirror mount or mirror position reconfigured quickly and/or easily by a user or at the factory.

Figure 56:
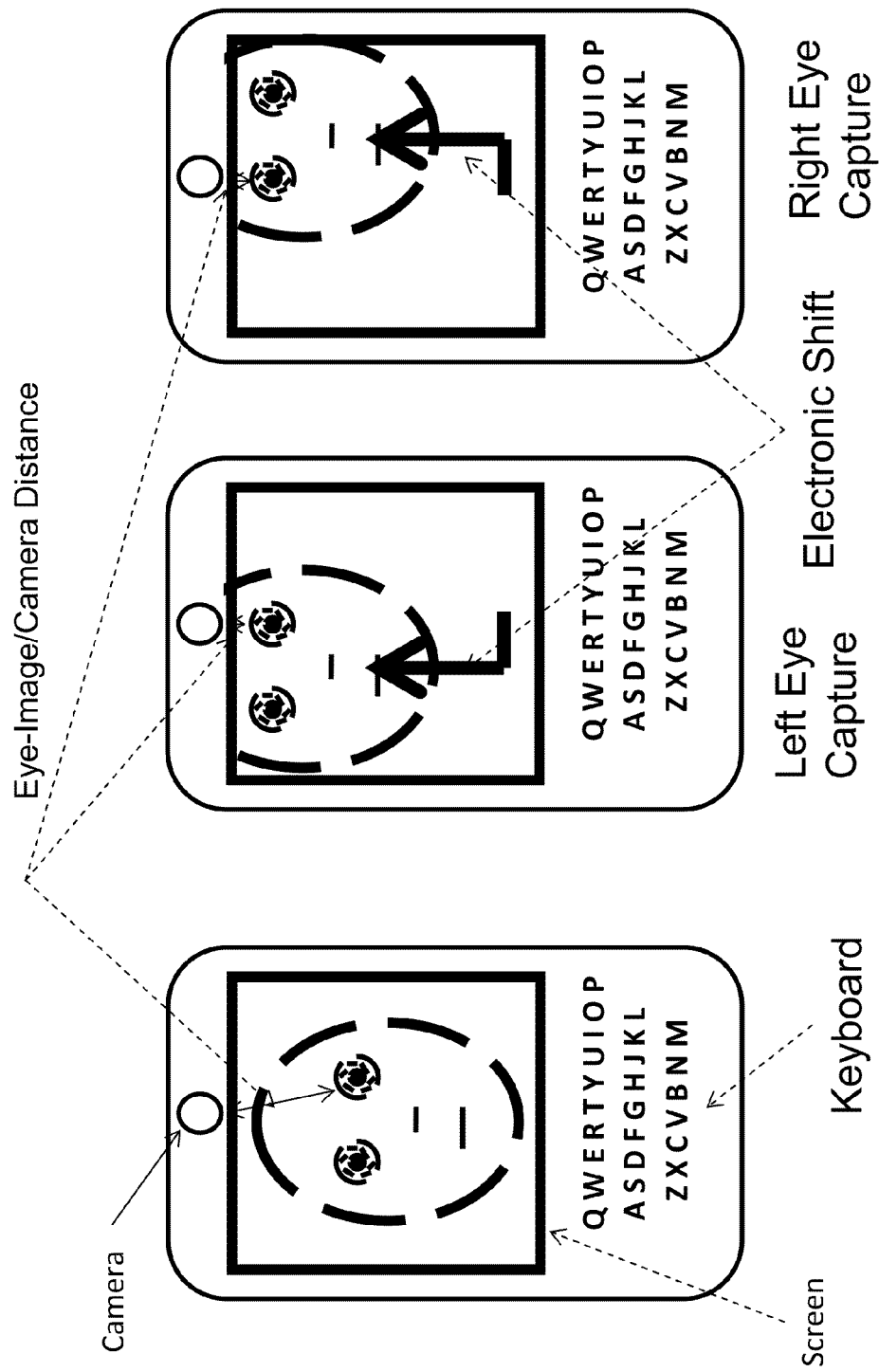
FIG. 56 depicts one embodiment of a system for positioning a dominant eye of a user and minimizing foreshortening of the acquired iris imagery.

FIG. 56 shows another embodiment of a positioning mechanism for guiding a user's iris towards the direction of a sensor. The role of mirror(s) discussed above may be simulated by the sensor, a processor and/or a screen. In some embodiments, such as in the case of a larger screen, the center of the screen may not be located close to the sensor. Thus, if the user looks near the center of the screen (such as at himself or herself) during image acquisition, the sensor may acquire a foreshortened view of the iris which is sub-optimal for iris recognition. When the view of the iris is foreshortened, the iris image may appear elliptical in shape rather than substantially circular in shape, thereby confusing or causing difficulties for iris recognition algorithms. For example, in FIG. 56, the scenario depicted on the left includes a large eye-image to camera/sensor distance, which can result in significant foreshortening.

Another challenge created by such a sensor/screen configuration is that user alignment may be more complex since the position of the eye of the user on the screen may be a function of the distance of the user relative to the sensor, as well as their horizontal and/or vertical position(s). In some embodiments, these issues may be addressed by electronically shifting or moving the coordinate system of the screen such that at the nominal/optimal operating distance of the device from the subject, the image of the subject acquired by the camera is electronically shifted such that the subject's left eye is positioned near, or as near to the camera as possible. The degree of shift may be predetermined (e.g., calibrated prior), and may be fixed for a particular device (e.g., with a fixed focus, zoom and/or camera/sensor position). The area just below the sensor on the screen may be highlighted with a different color or marking to guide or instruct the user to direct the user's eye at or near that area. Since the eye-image to camera distance can be shortened or minimized, foreshortening of the iris can be reduced or minimized. The complexity of alignment, by a user using the screen for guidance, is also reduced.

Referring again to FIG. 56, the device may electronically shift or move the screen image to direct each eye towards the direction of the sensor for image acquisition. For example, the center scenario may be suitable or optimal for acquisition of an image of the left iris. The scenario on the right side uses electronic shifting to direct the right eye towards the sensor for right iris image acquisition. In some embodiments, acquisition of left and right iris images can be performed using two modes of an application software running on the device. The application software may perform shape or feature recognition so as to locate and shift the correct features towards the sensor. A processor on the device may execute the application software and/or process images for rendering on the screen.

Figure 57:
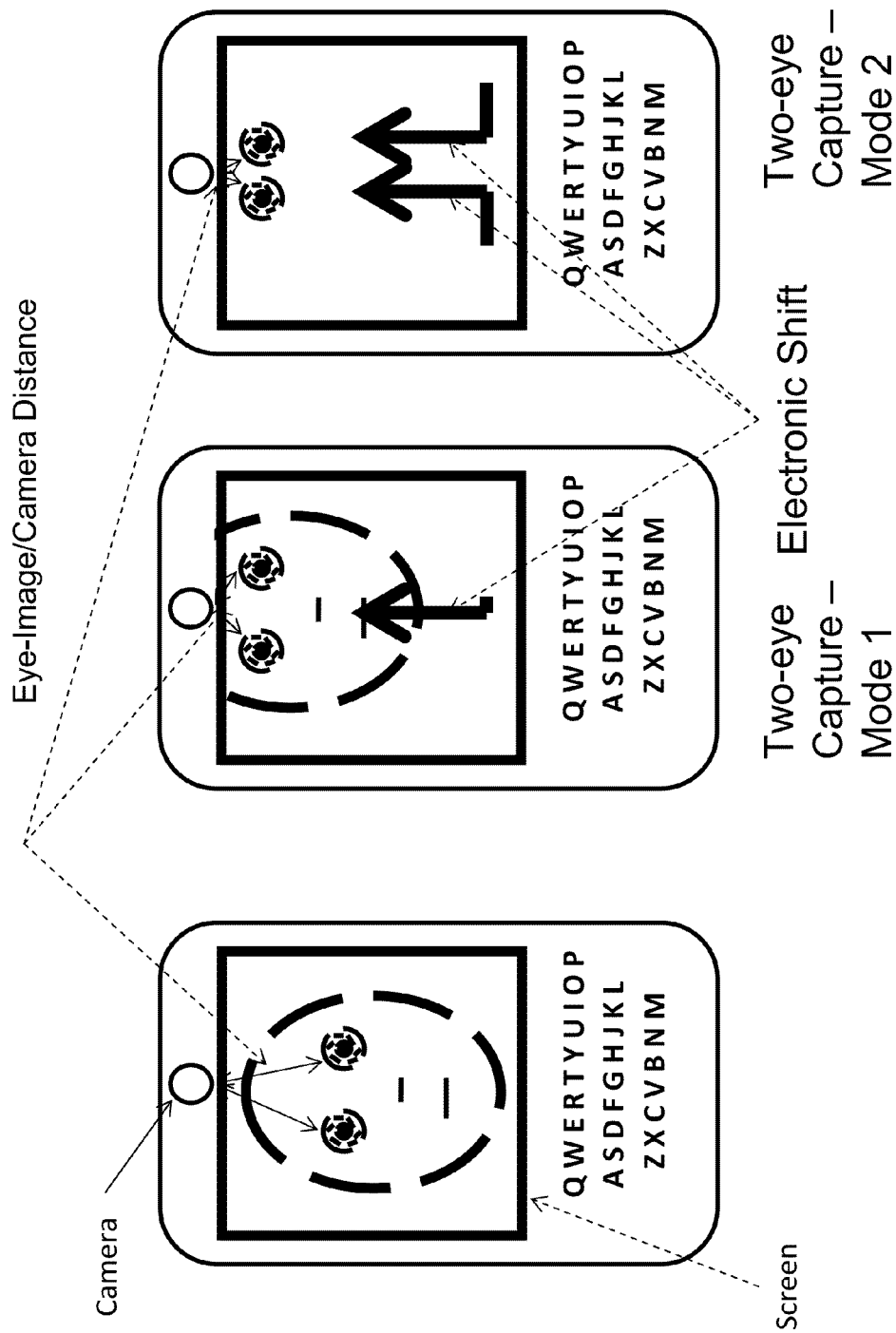
FIG. 57 depicts one embodiment of a system for positioning both eyes of a user and minimizing foreshortening of the acquired iris imagery.

Referring now to FIG. 57, embodiments of mechanisms for positioning a user for biometric capture are depicted. The implementation depicted in the middle may shift both eyes of a subject towards the direction of the sensor. This implementation may be optimized for two-eye simultaneous image capture, for example. The electronic alignment system may shift or move the displayed imagery of a user's face such that the image of both eyes are located near or beneath the sensor. The implementation depicted on the right of FIG. 57 may perform separate electronic alignment of the left and right eyes. The electronic alignment system may simultaneously apply the methods discussed herein to different portions of the acquired image (e.g., separately to isolated images of the left and right eyes). In this case, both eye images may be positioned very close together near the sensor, reducing foreshortening in both images simultaneously. Separate portions of the acquired imagery may be shifted differently, e.g., in different directions. In one embodiment, the subject's facial image may be split into two parts, e.g., about a vertical axis. The location of this image split may be dependent on the position of the camera with respect to the screen. For example, if the sensor is on an axis through the middle of the screen, the split may be performed along the middle of the image on the screen.

The positioning mechanisms discussed above may assume that the user is able to easily face or orient the device. However, in some identity verification applications, it may be intrusive or undesirable for a user to pick up an image acquisition device, on a regular basis for example, to verify oneself. In other identity verification applications, such as a fingerprint biometric sensor, it is possible to articulate a wrist and/or finger so that a fingerprint is presented to the sensor. However, with an iris sensor, it may be key for an eye of the user to face directly towards the sensor. An embedded device incorporating the iris sensor can allow the sensor to be oriented towards an iris. Such an embedded device may be compactly built and sufficiently streamlined to be inserted into and/or carried comfortably in a pocket of a user. As discussed earlier, FIG. 39 depicts one embodiment of a positioning mechanism that may be attached or incorporated into such an embedded device.

In some embodiments, the positioning mechanism may include a portion that can connect or plug to a host computer or other computing device (for example, via a USB jack). The positioning mechanism may include a second portion that can be articulated by the user, substantially unencumbered by the first portion. For example, a cable, which may be flexible and/or retractable, and may connect the two portions. In some embodiments, the second portion may be articulated relative to the first portion. For example, the two portions may be linked by an articulated arm or stiff wire, which may be bent or twisted into a particular shape. For example, the second portion may be positioned towards a user, away from a host computer. In this way, a user can move or dip towards the embedded device in a hands-free fashion, for the user's biometric data to be acquired. The articulated arm or mount may be straightened or twisted into shape, e.g., for portability. The articulated arm or mount may be reshaped to fit in a pocket of the user, e.g., so as to avoid discomfort. Other positioning mechanisms may include a cradle that can be placed on a desk or platform, or a cradle that attaches to or hangs over a screen of a computing device.

Figure 58:
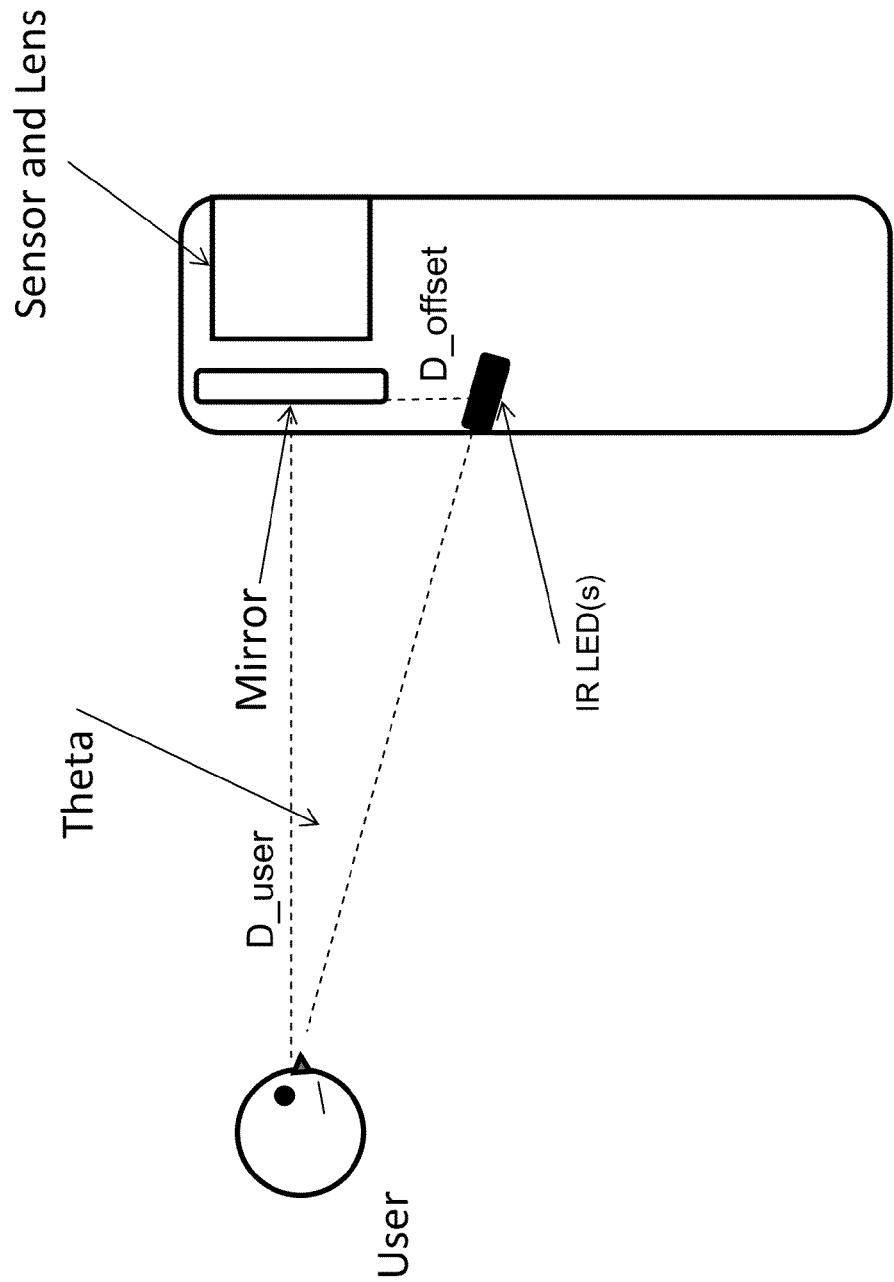
FIG. 58 depicts one embodiment of a system that illuminates an iris with narrow-beam infra-red light.

In some embodiments, the image acquisition device may include a mechanism that suitably illuminates an iris when the iris is aligned with a sensor for image acquisition. In some embodiments, this includes a narrow-beam illuminator, such as an infra-red LED. In some embodiments, the illuminator is positioned to point towards an iris of the user when aligned using any of the positioning mechanisms described earlier. The beam of the illuminator may be sufficiently narrow and shaped to only cover an iris area. Such an implementation may be more energy efficient, and may help guide positioning of the user using infra-red and iris detection, for example. FIG. 58 depicts one embodiment of a configuration for positioning the illuminator. For example, the angle of the infra-red LED compared to the axis of the eye may be expressed as theta=a Tan(D_offset/D_user), where D_offset is the distance between the camera and the IR LED, and D_user is the nominal/optimal distance between the device and the user.

Figure 59:
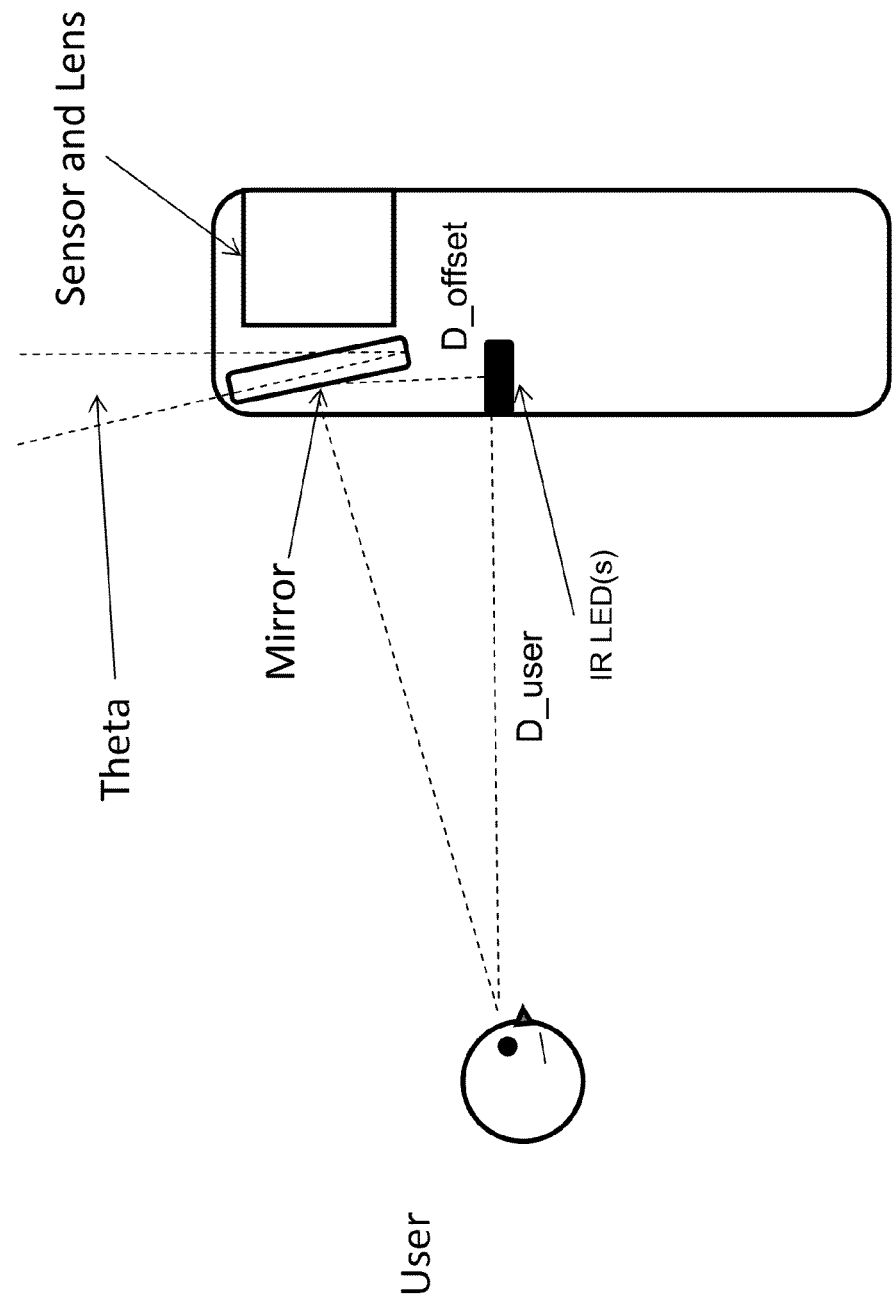
FIG. 59 depicts another embodiment of a system that illuminates an iris with narrow-beam infra-red light.

FIG. 59 depicts another embodiment whereby the optical axis of an illuminator is configured to be orthogonal to the surface of the casing, or an internal circuit board of the device. Such a configuration may ease manufacturability since the LEDs can be mounted using standard component-mount techniques. In this embodiment, a positioning mirror may be tilted such that the optical axis of the mirror and the optical axis of the infra-red illumination converge at the nominal/optimal user position, e.g., on the user's iris. In either embodiment, as well as some other embodiments, it may be preferred that the position of the infra-red LEDs is at the same level as, or below, the level of the camera/sensor with respect to the front of the subject's head, so that eyelash shadow does not hinder the positioning or is introduced into the acquired imagery.

Figure 60:
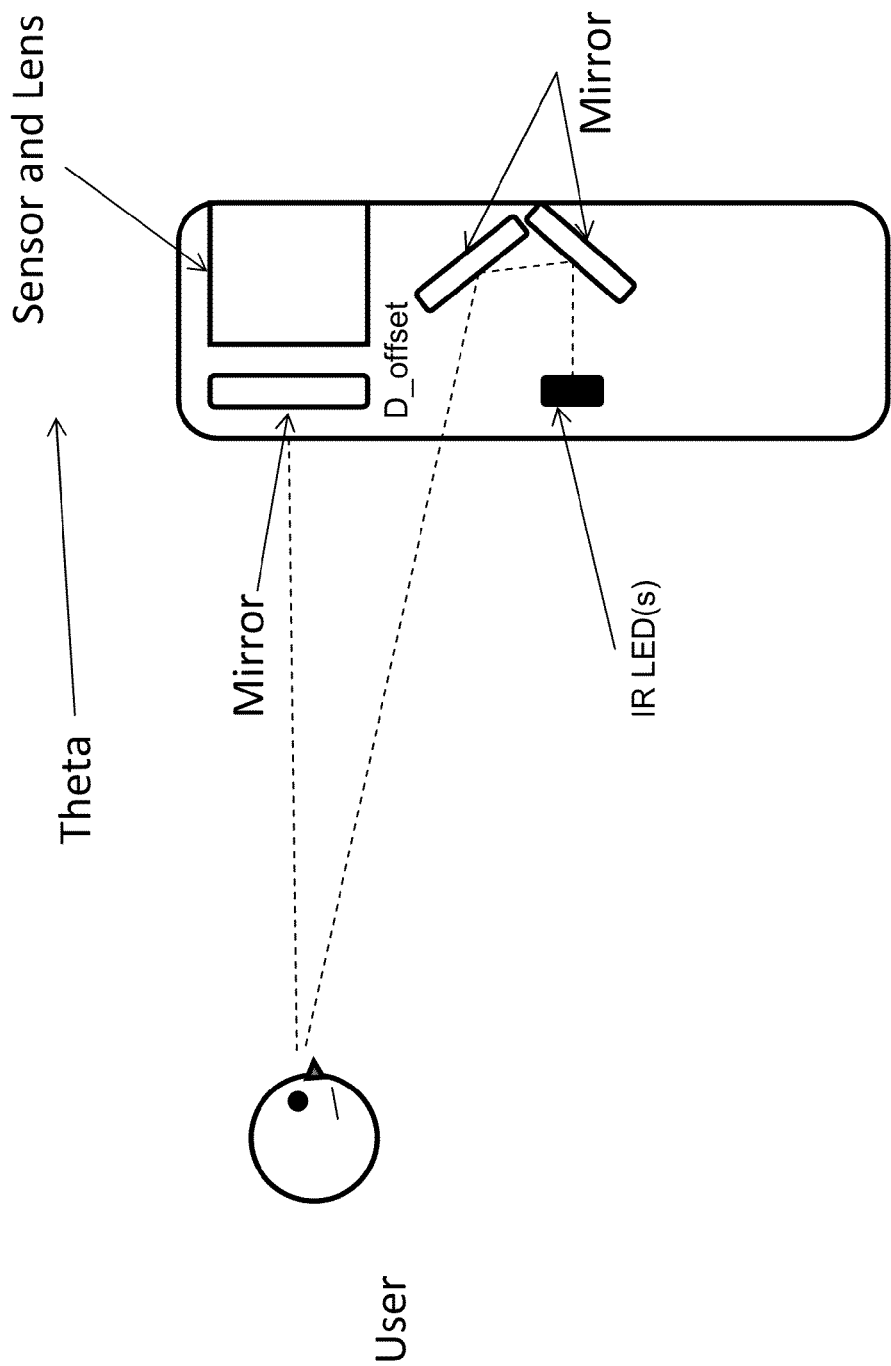
FIG. 60 depicts yet another embodiment of a system that illuminates an iris with narrow-beam infra-red light.

FIG. 60 depicts yet another embodiment whereby illumination from an IR illuminator, with its optical axis being mounted parallel to the optical axis of the camera, is reflected off mirrors and directed at an angle towards the position of the user. The illuminator may be configured to be orthogonal to the surface of an internal circuit board of the device. In some embodiments, D_offset may be reduced or minimized so that more light may be reflected off an iris to a sensor.

Figure 61:
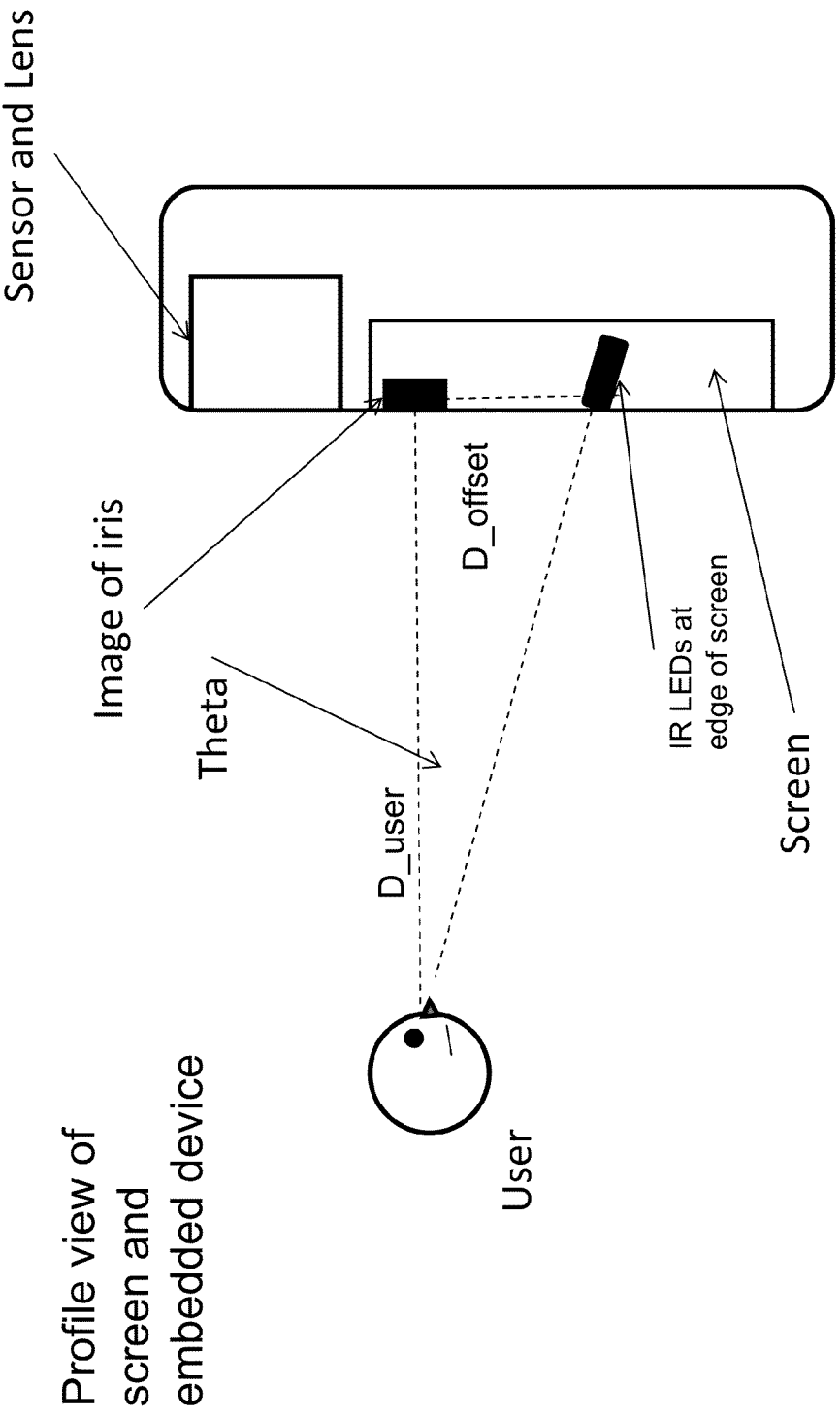
FIG. 61 depicts one embodiment of a system that positions and illuminates a user's eyes.

FIG. 61 shows another embodiment of the image acquisition device. The device may use the mirror-simulation mechanism described earlier, using images displayed on a screen to position a user. The image of the iris may be electronically shifted to be as close to the camera as possible. One or more illuminators may be located near one or more edges of the screen. The optical axis of one illuminator may be pointed towards an iris at the nominal/optimal position of the user relative to the device.

Figure 62A:
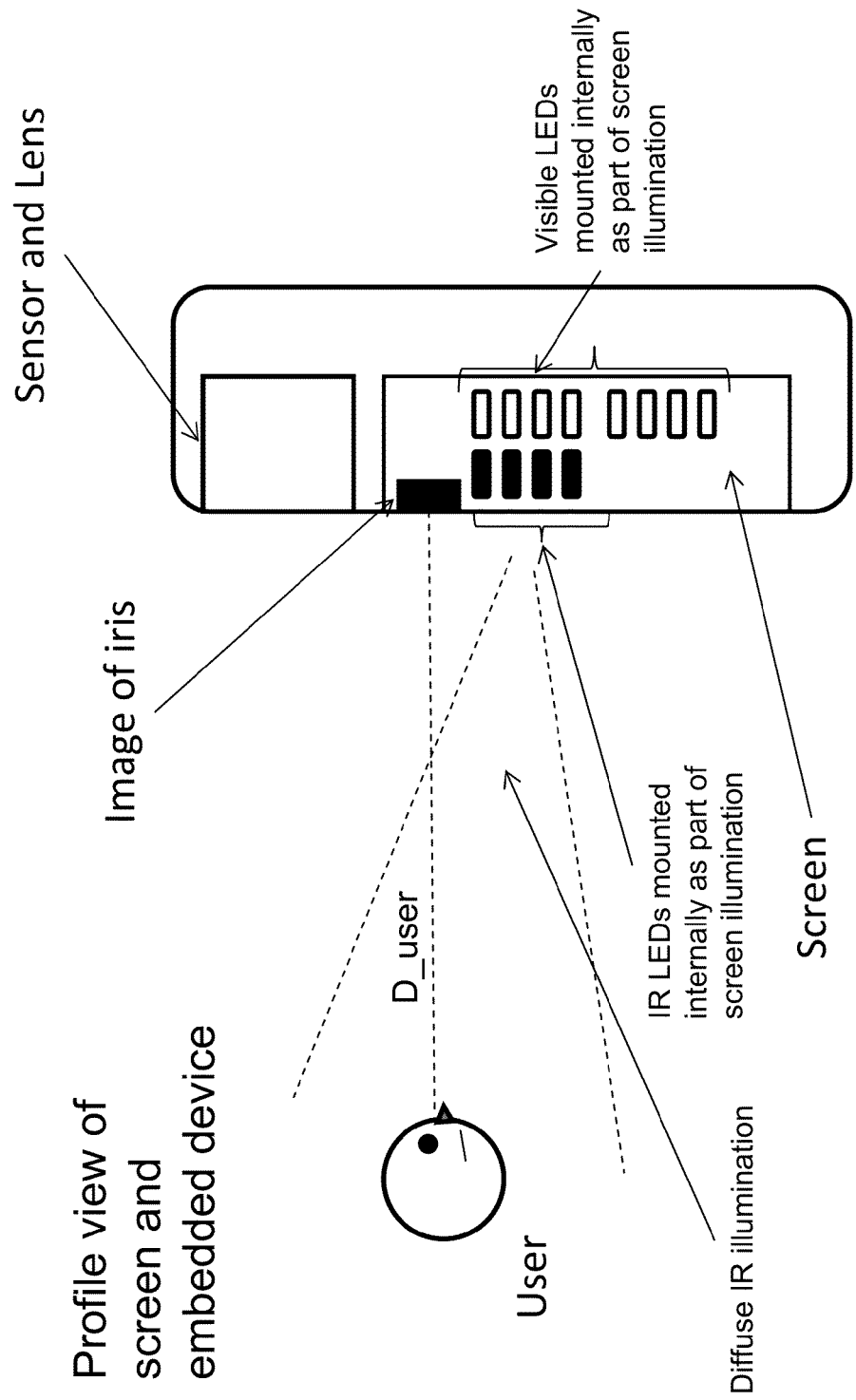
FIGS. 62A and 62B depict embodiments of an integrated, compact system that positions and illuminates a user's eyes for biometric acquisition.
Figure 62B:
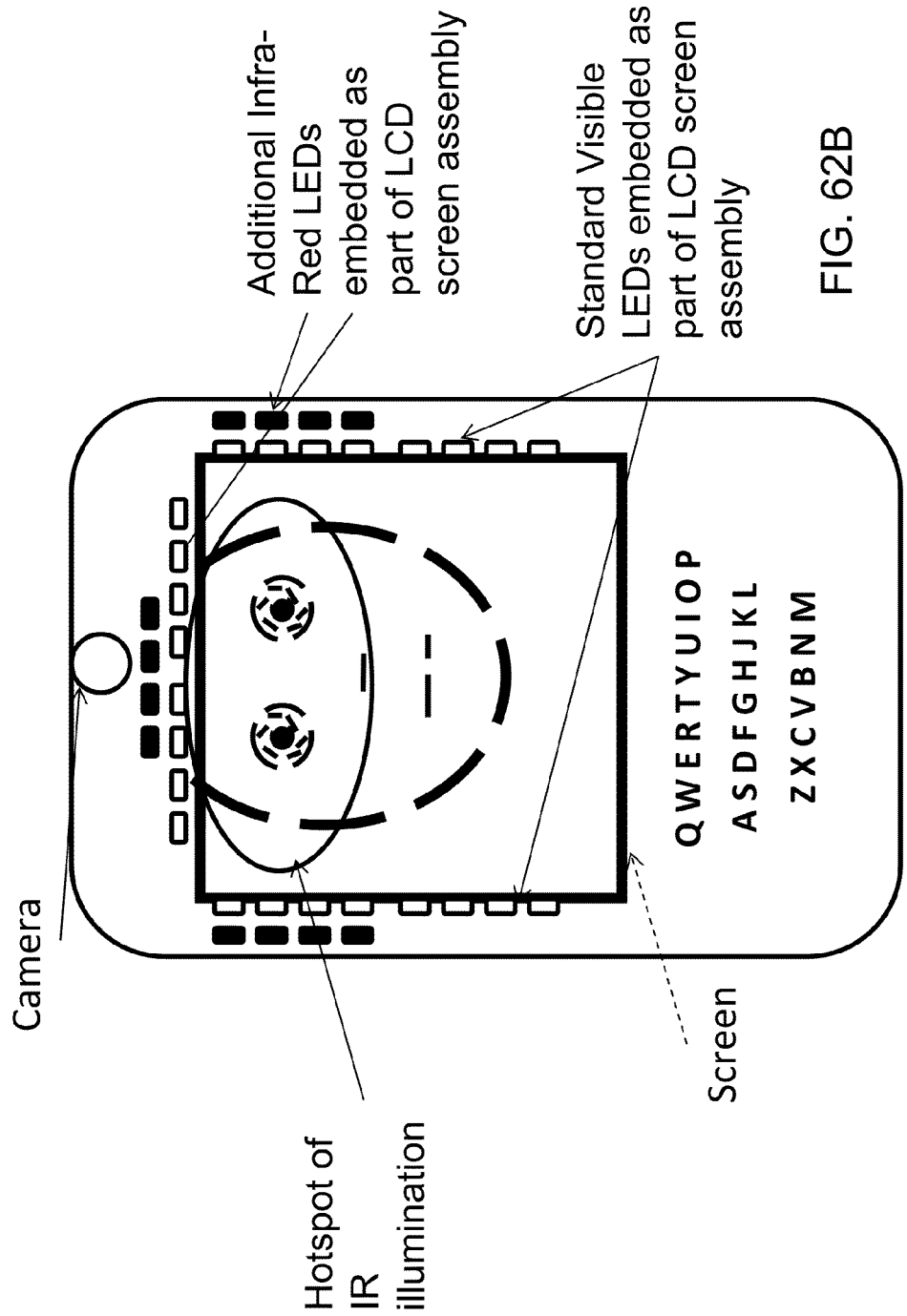

FIGS. 62A and 62B depict embodiments of the image acquisition device. These embodiments may enable acquisition of well-illuminated iris imagery by employing a screen that provides illumination. The screen may optionally emit infra-red illumination as well as visible illumination. The screen may comprise a Liquid Crystal Display (LCD). LCD screens are constructed by having rows of LEDs mounted internal to each screen and/or surrounding the screen. Diffusers can project illumination upwards to the user, through polarizing material, a Liquid Crystal Panel and color filters that form each individual pixel on the screen. Such illumination may be provided by visible light LEDs, which may be standard for display screens. Some embodiments of the image acquisition device may incorporate additional infra-red LEDs at the edges of the screen, for example. In some embodiments, infra-red LEDs may be incorporated in the screen. This infra-red illumination may be diffused and projected towards the user. Color filters are typically transparent to infra-red illumination, and the infra-red illumination may pass unimpeded, or substantially unimpeded, to illuminate the iris for biometric capture.

In some embodiments, the infra-red LEDs may be grouped or concentrated within an area of the screen, for example as shown in FIG. 62B. First, the cost of adding the infra-red LEDs (e.g., grouped and/or located within a smaller region) may be reduced, and second, a smaller region of the screen may be illuminated by the infra-red illuminators. This is significant since as the area of illumination increases, then the area of specularity reflected off the cornea may also increase, occluding imagery of the iris itself. By limiting the area of infra-red LEDs, specularity from the cornea may be reduced, increasing biometric acquisition performance. Also, as stated in standard ISO specifications for iris recognition, it is preferred that the size of any corneal specularity be minimized such that it is contained within the pupil of the iris imagery. Limiting the location and region of infra-red LEDs may help achieve this.

In some embodiments, the infra-red LEDs may be independently controlled by the device so that a rudimentary infra-red display is created. In this case, basic shapes in infra-red can be projected from the screen, reflected off the cornea and collected by the camera imager or sensor. These shapes may be changed by computer control via the device, detected, and used as a means to determine liveness of the user in front of the device. This serves as a way to determine that biometrics acquired are from an actual live person instead of a recorded image of an eye, for example.

In some embodiments, imagery from the sensor is collected both with the infra-red shapes turned on and then turned off. Both sets of imagery may then be stored and subtracted to reduce effects of contamination and unpredictable visible illumination (e.g., from the screen, and/or ambient light). For example, embodiments of such methods are discussed above in connection with at least FIGS. 13-23 and 37-38. Since the user cannot see the infra-red illumination, infra-red illumination projected from the illuminators can be very bright, and turned on and off regularly without causing annoyance to the user. This approach allows iris recognition or face recognition to be performed on imagery collected via controlled illumination from the screen of the device. By integrating IR illuminators to a screen, the device can significantly more compact.

Figure 63:
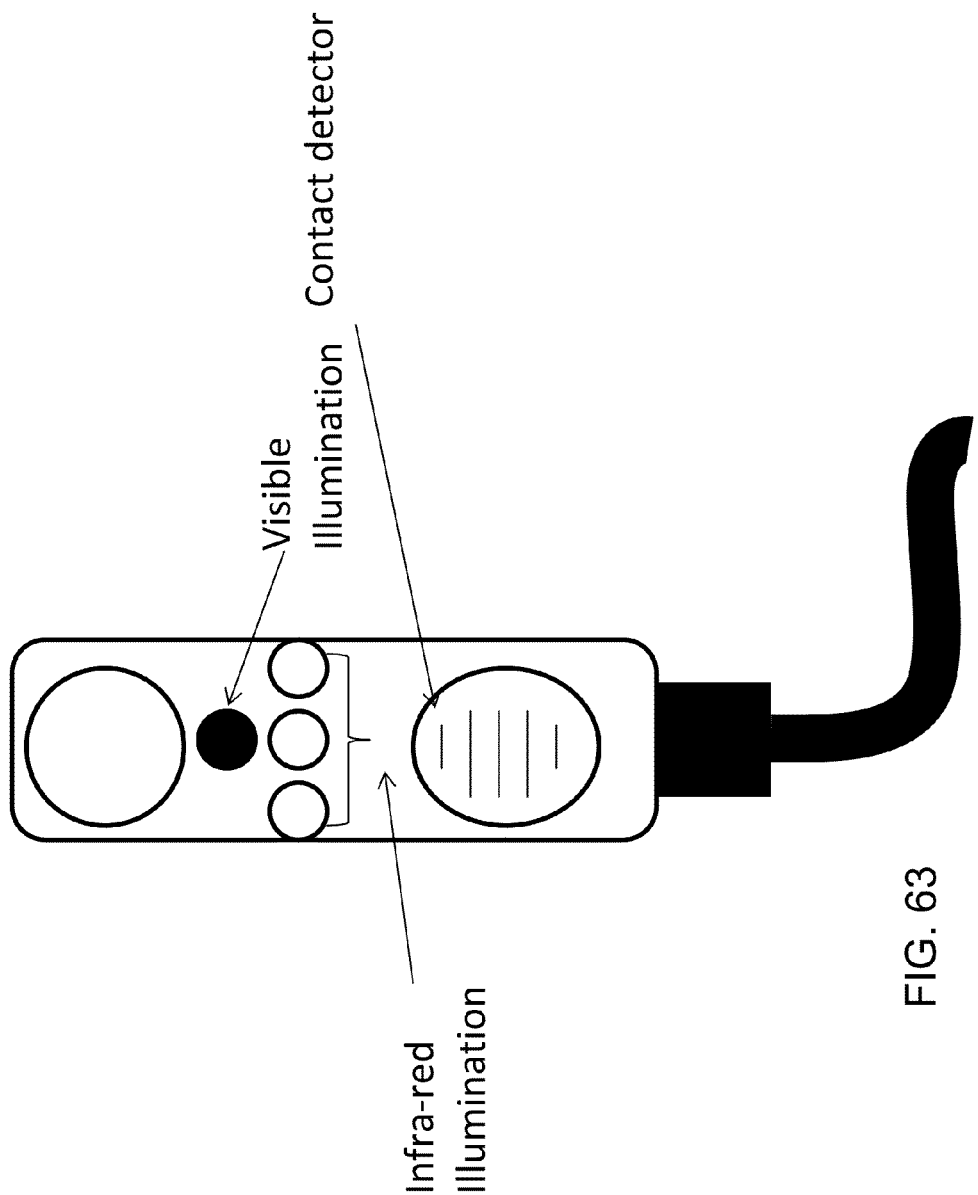
FIG. 63 depicts one embodiment of a handheld system for biometric acquisition.

In certain embodiments, the image acquisition device incorporates a positioning system that achieves well-lit and un-occluded acquired iris imagery while providing simple and rapid alignment of the user's eye with a sensor. Biometric features may not be well-lit if the user places a finger over LEDs on the device. Occlusion in iris imagery may be caused by improper positioning of fingers over a sensor of the device. This can be a significant problem as the size of an image acquisition device becomes smaller, where it is more likely that a user's hand will cover a larger portion of the device when held. FIG. 63 shows an implementation for addressing this problem, by providing an area or marker to help position the grasp of a user's hand. For example, a marker, such as a 2D or 3D representation of a thumb-print or thumb-rest, positioned away from areas of the device occupied by the sensor and infra-red LED(s), may be incorporated on the handheld device. The marker may provide user guidance to indicate that the user's thumb should be placed at the marker. By positioning the user's grasp according to the market, for example as shown in FIG. 64, it is less likely for the user to inadvertently occlude a sensor or illuminator area.

In some embodiments, the camera/sensor may be located near one end of the device, e.g., near the top of the device. The infra-red illuminator(s) may be positioned below the camera, e.g., to avoid casting shadows on a user's eyelashes. The thumb-rest or marker may be located beneath the area occupied by the infra-red illuminator(s). Optionally, a contact detector on the thumb-rest/marker area can be used to detect if a thumb is present, and can be used to avoid acquisition of imagery that may be sub-optimal if the device is not held properly during the time of acquisition.

Figure 64:
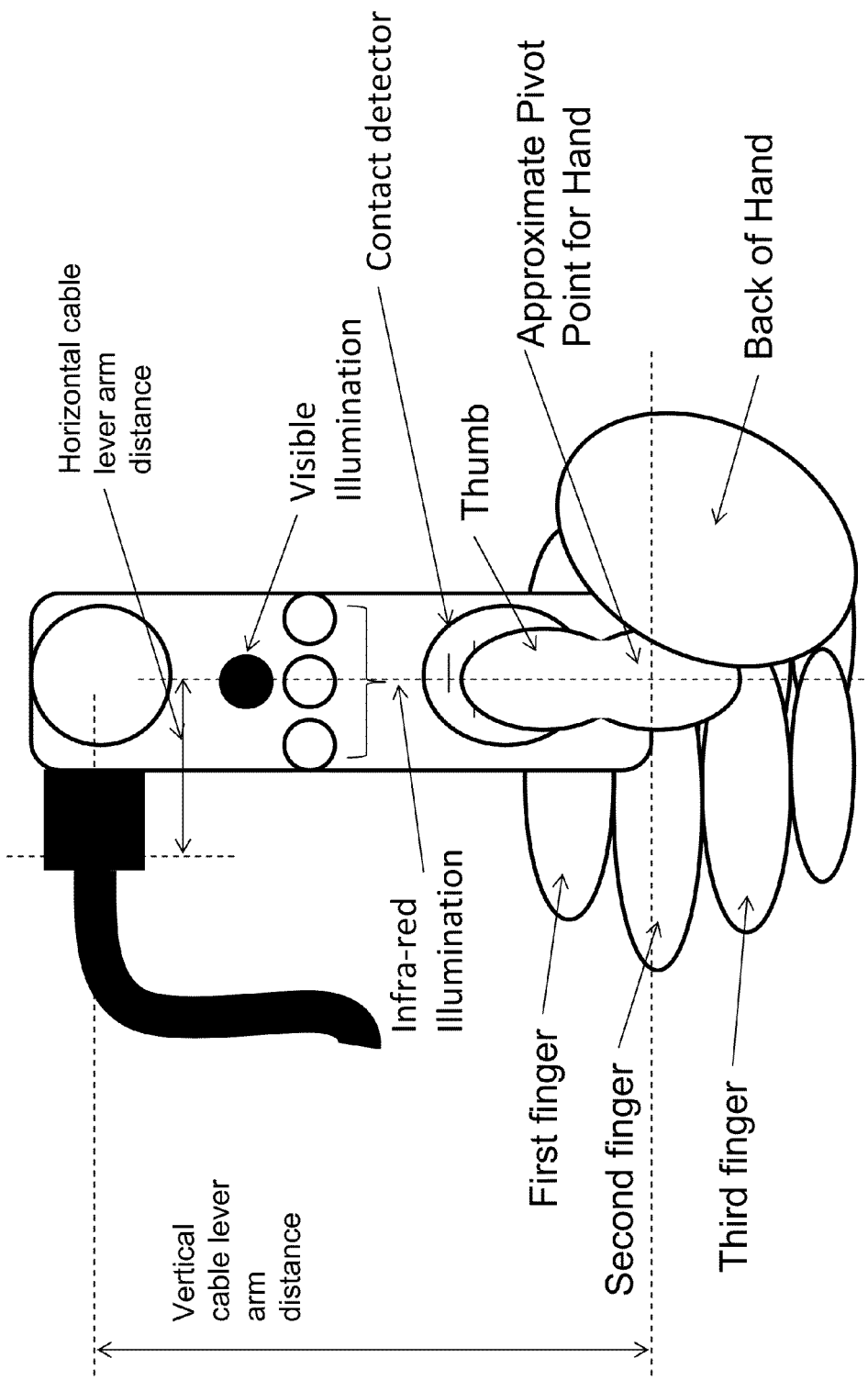
FIG. 64 depicts another embodiment of a handheld system for biometric acquisition.
Figure 65:
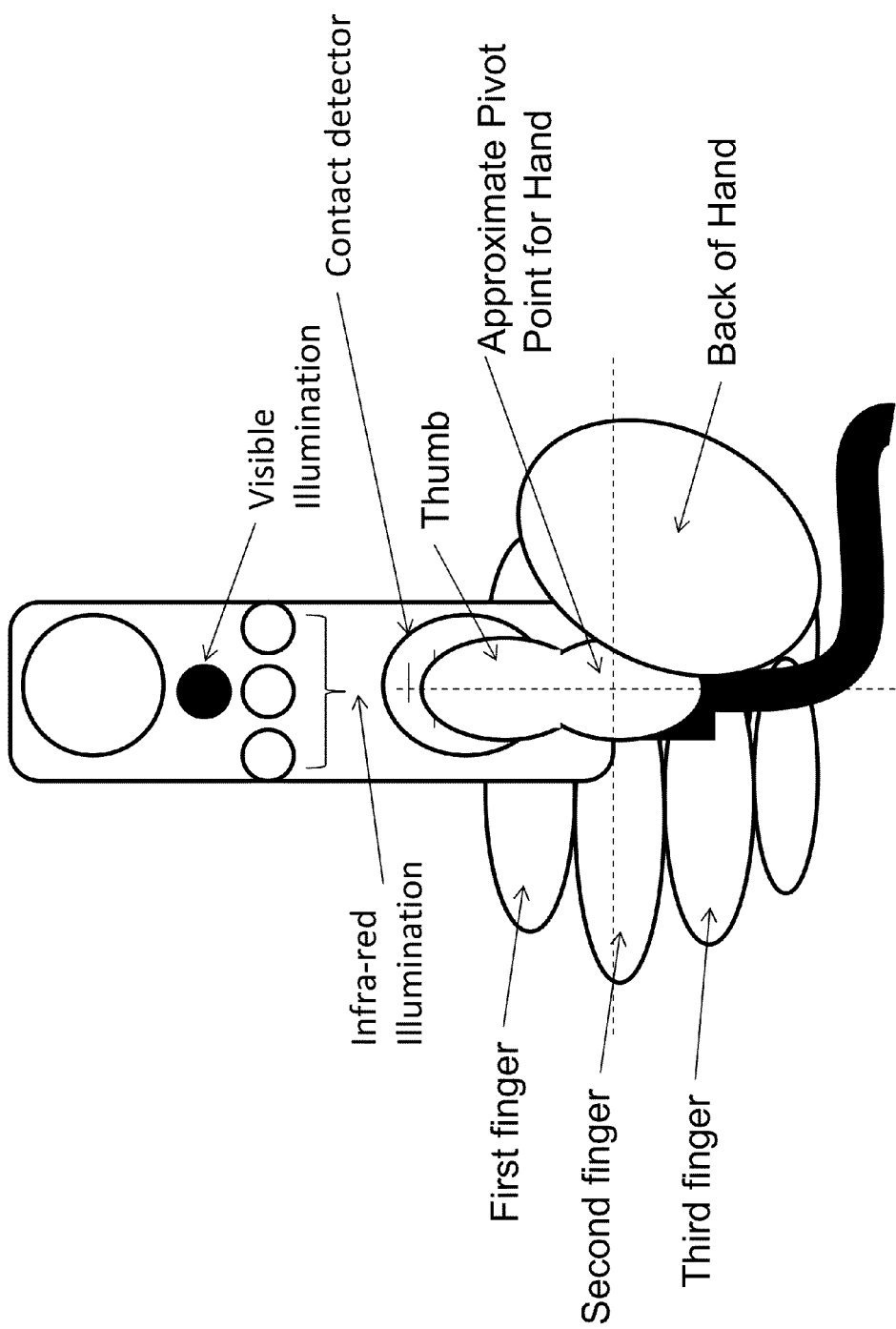
FIG. 65 depicts an embodiment of a handheld system for biometric acquisition.

FIG. 64 illustrates one embodiment of the handheld image acquisition device. Positioning mechanisms of the device may be noticeably harder to use if the cable connector is mounted at particular locations on the device. When using the positioning mechanisms described herein, a user may shift and/or tilt the device around the pivot point of their wrist. If the cable connector is far from the pivot point, then the lever arm force exerted on the wrist of the user by the weight and stiffness of the device connector/cable can be substantial, and may make it more difficult to use the positioning mechanisms described herein. This effect may be mitigated by positioning the connector/cable near the pivot point of the user's wrist when the device is being held, e.g., according to the thumb-rest guidance mechanism. In such embodiments, the distance between the pivot point of the user's wrist and the location of the connector/cable is smaller, so that the lever arm distance and subsequent forces on the user's wrist are reduced, as shown in FIG. 65. In some embodiments, a preferred configuration is to have the camera on top of the device, the infra-red illumination below the camera, the thumb-rest/marker area beneath the LED area, and the connector/cable region at the lower end of the device, either exiting to the sides or underneath the device.

Figure 66:
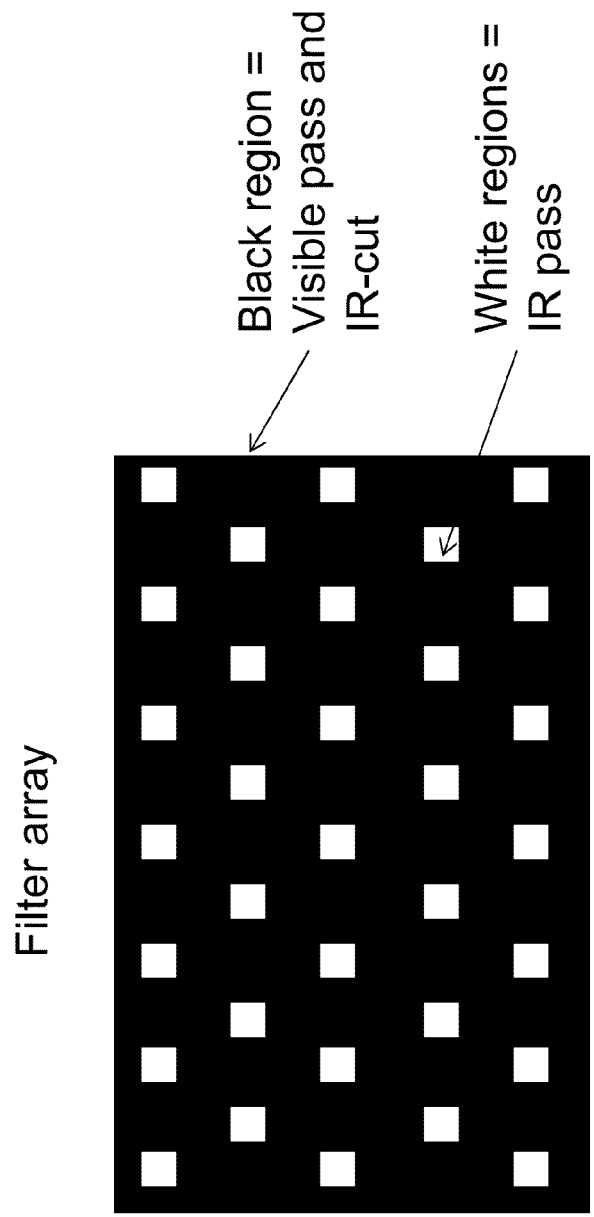
FIG. 66 depicts one embodiment of a system that uses a single sensor and a filter array to produce infra-red and non-infra-red images.

In some embodiments, the biometric/image acquisition device uses a single compact sensor to acquire high quality images of a scene in visible illumination as well as high quality images of an iris with infra-red illumination. FIG. 66 shows one embodiment of a filter array that may be used with a single sensor. The filter array may comprise distributed IR-pass and IR-cut components. One method of forming such a filter array is to laser-drill holes at regular vertical and horizontal sampling intervals on a uniform IR-cut filter. The latter may be standard in many camera modules (e.g., smartphone cameras, tablet cameras). Other methods for creating such a filter array can be used, and the array may comprise other filter elements, such as visible-pass/IR-cut filter elements in some sampled regions of the filter, and visible-cut/IR-pass filter elements in other sampled regions of the filter. In some applications, there may be a need to preserve the pristine quality of visible imagery, and meet signal-to-noise requirements and/or certain visible image resolution. As such, some embodiments of the image acquisition device may configure sampling of the infra-red cut component of the filter array to exceed sampling of the infra-red pass component of the filter array. The image acquisition device may sample the infra-red cut component of the filter array substantially at or below a corresponding Nyquist rate for the infra-red cut component. The image acquisition device may sample the infra-red pass component of the filter array substantially at or below a corresponding Nyquist rate for the infra-red pass component. Sampling substantially at or below a corresponding Nyquist rate may avoid the effects of aliasing.

In some embodiments, significant sub-sampling of infra-red pass imagery can creates two problems. First, severe sensor sub-sampling can create aliasing thereby making the acquired iris imagery useless. Second, resulting resolution of the acquired iris imagery may be lower thereby making iris recognition unreliable. ISO standards for iris recognition, for example, recommend acquisition of iris imagery that is 100-200 pixels in diameter. The present systems and methods take advantage of a phenomenon whereby the optical Modulation Transfer Function (MTF) of lenses in embedded devices are often unable to resolve to the resolution of the sensor itself. In other words, the quality of lenses have not kept up with the ever increasing resolution of sensors. This is especially so as sensors become smaller and support higher resolutions. The device can therefore sub-sample at high values and still not get much aliasing. That enables the device to acquire non-aliased images of irises in infra-red light while at the same time be able to acquire high quality iris images. The filter array may be configured such that the IR-pass component of the filter is significantly sub-sampled compared to the pixel spacing of the sensor. The rate of sub-sampling can, for example, be a factor of 2-6 in each coordinate axis of the sensor array. Such large sub-sampling factors means that the IR-cut portions of the filter can sample more of the visible imagery, so that signal to noise and resolution of the visible components are not compromised.

In contrast, U.S. Pat. No. 7,872,234 discloses a method that uses very densely sampled infra-red arrays to prevent aliasing. For example, with a sub-sampling factor of 2, $(\frac{1}{2})*(\frac{1}{2})=25\%$ of visible pixels are affected. This has the drawback of compromising the quality (signal to noise and resolution) of the visible imagery since a large portion of the data used to construct the visible imagery is lost. U.S. Pat. No. 7,872,234 mitigates this by performing color compensation at each visible pixel cluster. However such color compensation can introduce artifacts at each pixel, and the signal-to-noise value of the basic visible image signal is compromised since less incident photons are being used to create the visible image, which is especially significant when the sensor size is small and has low signal to noise properties.

By using larger sub-sampling of the infra-red component in some embodiments of the present image acquisition devices, a smaller proportion of visible pixels are affected. For example, with a sub-sampling factor of 4, only (¼)*(¼)=6.25% of visible pixels are affected by the IR sampling. With a factor of 6 sub-sampling, (1−(⅙)*(⅙))=97% of visible pixels remain untouched. Typically, such large pixel arrays already have dead or high/low gain pixels, and very different interpolation methods are well-developed and tested to fill in such anomalies that occupy increasingly smaller percentages of the screen area. For example, such small anomalies can be mitigated by applying median filtering/averaging over pixels in the surrounding area. Thus, small amounts of IR sampling affecting a small number of visible pixels may be compensated using such approaches. Median filtering is, however, not suitable if visible pixels are low (e.g., high IR sampling, as in U.S. Pat. No. 7,872,234), since median filtering can cause artifacts if such compensation had to be performed at every pixel cluster—there are few if any surrounding uncontaminated visible pixel data as an input to the median filtering/averaging algorithm. The signal to noise value of the acquired visible imagery is also not significantly compromised since the vast majority of pixels in the sensor array are still being used to produce the visible imagery.

The iris data acquired by the IR-pass component of the array may be small due to the large sub-sampling, and may be so even after interpolation. In some embodiments, the image acquisition device may resolve this by acquiring the iris imagery at a higher resolution than typical iris acquisition resolutions. This may be achieved by acquiring a larger image of the iris, e.g., by positioning the iris closer to the sensor. For example, if an interpolated iris imagery of 100 pixels in diameter is needed, and a filter array is used with an IR-pass sub-sample value of 4, the image acquisition device may be configured to acquire iris images at a distance such that the diameter of the iris with respect to the original sampling of the sensor is 400 pixels. The size of the acquired iris image, Iris_diameter_acquired, may be given by Iris_diameter_acquired=Iris_diameter_required×IR_pass sample value, where Iris_diameter_required is the interpolated iris diameter required for iris recognition, and IR_pass sample value is the sampling of the IR-pass component of the filter array.

Figure 67:
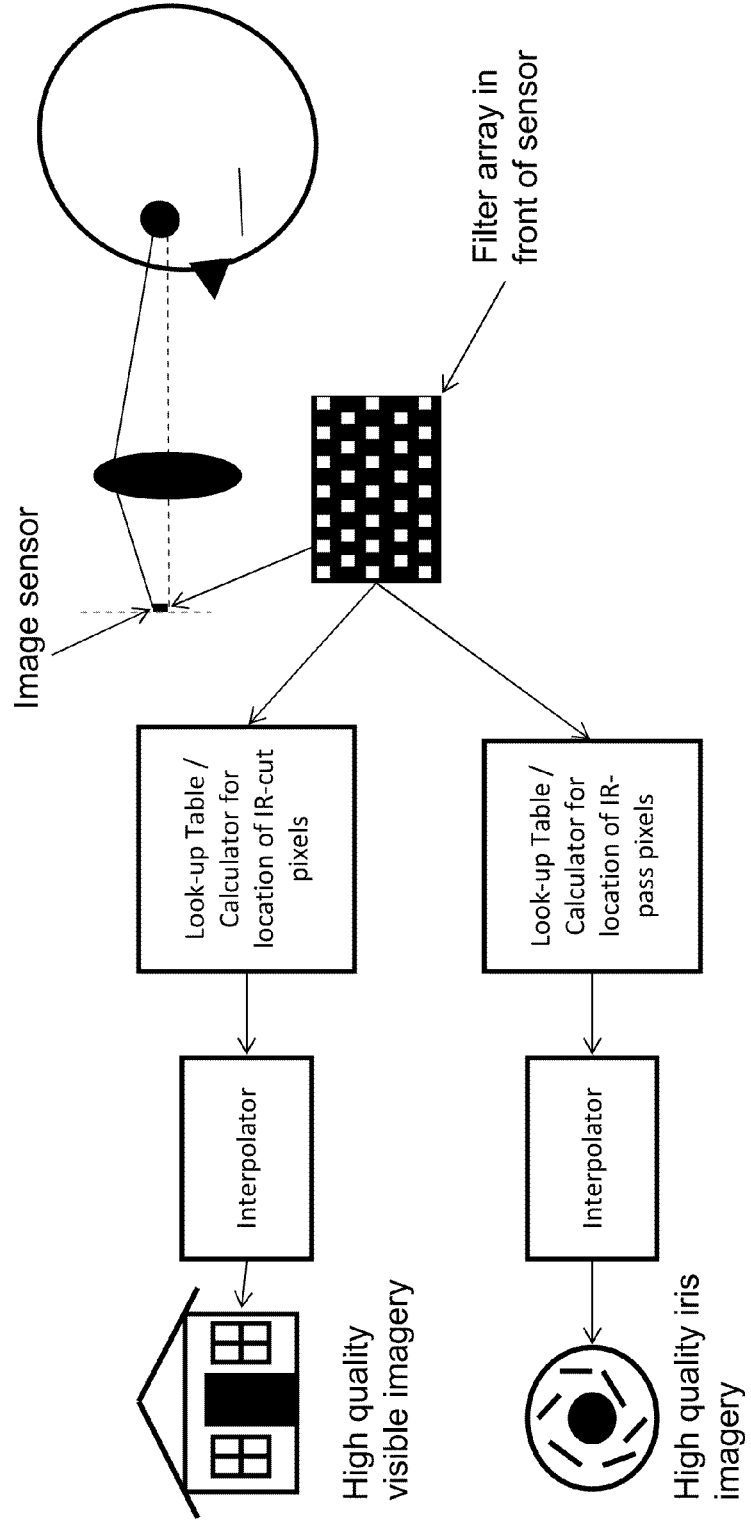
FIG. 67 depicts one embodiment of a system for identifying and processing data from infra-red-pass and infra-red-cut components of a filter array.

As discussed above, the sampling interval for the sparsely sampled regions may correspond to every $2^{nd}$-$6^{th}$ pixel in the sensor array that lies underneath the filter array. In some embodiments, a look up table or pixel calculator may be used to determine or predict which pixels of the sensor are or are not exposed to infra-red light, for example as shown in FIG. 66. These pixels are then passed through separate image interpolator algorithms to create separate images from each of the exposed sets of pixels. The set of pixels not exposed to infra-red light may produce seamless high resolution images of standard scenes in visible light. The set of pixels exposed to infra-red light may produce seamless high resolution images of an iris, as shown in FIG. 67. If the filter is aligned carefully and repeatedly to the sensor pixels, then the lookup table or calculator can be pre-programmed based on the geometry of the sensor pixel spacing.

In some embodiments, if the filter is not aligned carefully to the sensor pixels, then an initial and/or rapid calibration step can be performed to determine which pixels are exposed to infra-red light. The calibration step may, for example, comprise pointing the sensor, filter and lens combination towards an infra-red light source (such as a matt reflective surface illuminated by an infra-red light source) and the resultant imagery recorded. Pixels underneath the IR-cut portion of the filter may appear dark, and pixels underneath the IR-pass portion of the filter may appear bright. These bright and dark variations may be detected by or compared against a threshold, for example, and pixels that exceed the threshold may be identified as being under the IR-pass portion of the filter and can be inserted into a lookup table for example.

Figure 68:
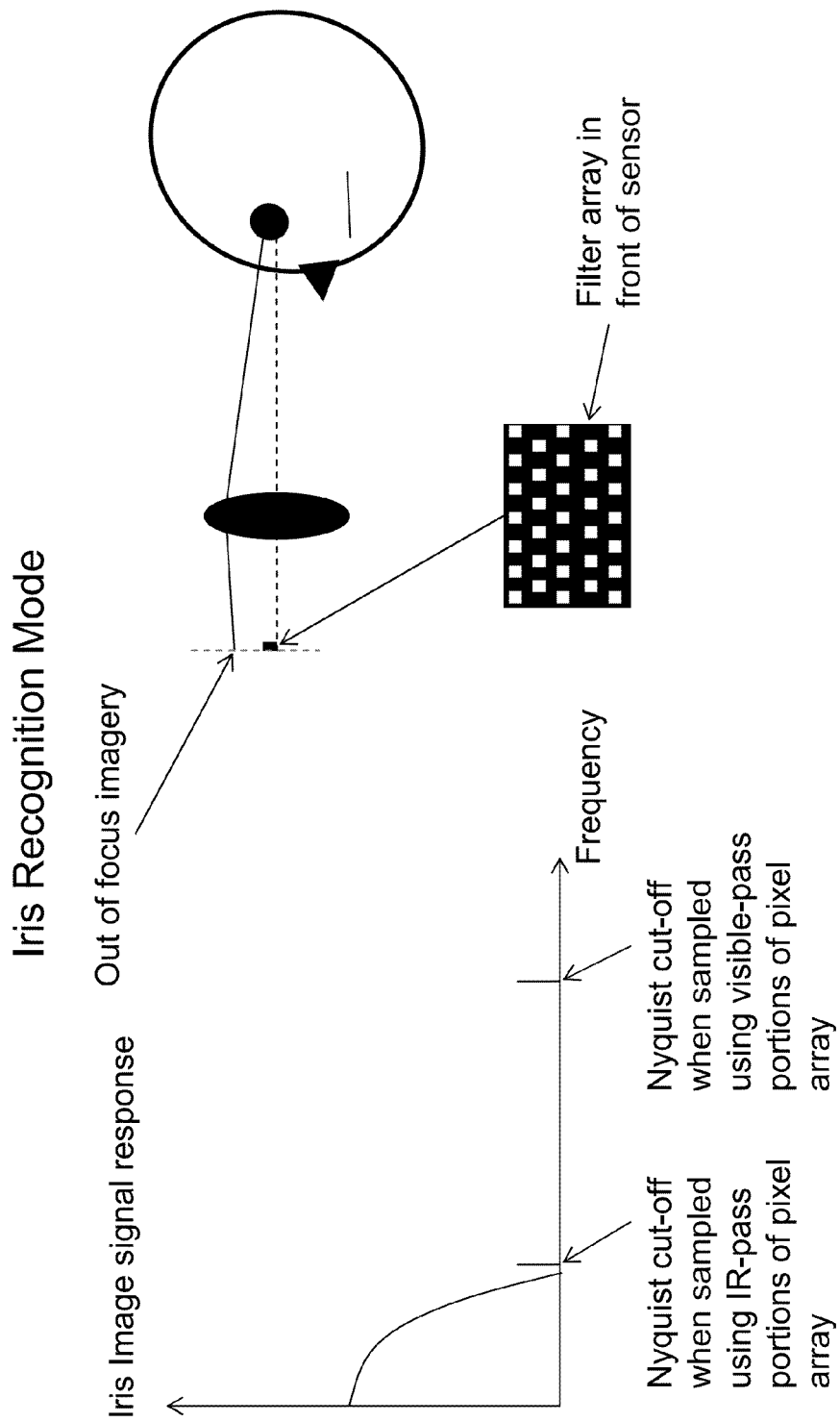
FIG. 68 depicts one embodiment of a method for preventing aliasing of iris imagery sampled using a filter array.
Figure 69:
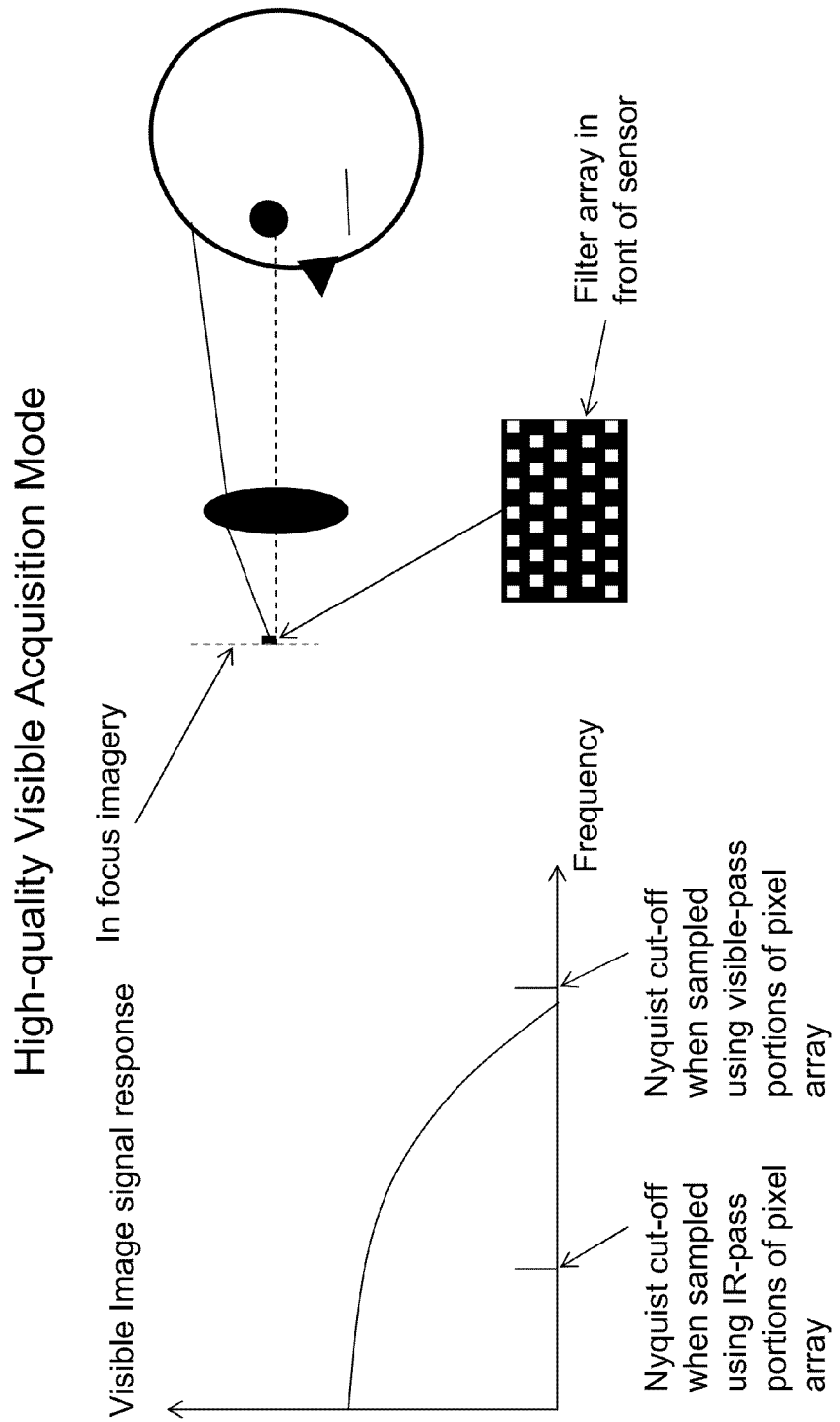
FIG. 69 depicts one embodiment of a method for preventing aliasing of data sampled from the IR-cut regions of a filter array.

In some embodiments, in which higher sampling of the filter array by the IR-pass component may result in aliasing, the image acquisition device's lens can be intentionally defocused in order to blur the imagery incident on the sensor. This can reduce the impact of aliasing, as shown in FIG. 68. Using techniques such as increasing the resolution of the iris image captured, interpolation and/or median filtering, degradation from de-focusing may be reduced. FIG. 69 shows how high quality, in-focus visible imagery can be acquired since the IR-cut portion of the filter is highly sampled. The IR-cut portion of the filter is sampled substantially at or below a corresponding Nyquist rate to avoid effects of aliasing.

In some embodiments, the array of sensor pixels of the device's sensor may be built to correspond to the filter array. For example, RGB pixels may be located at visible sample locations, and IR sensor pixels located beneath IR-pass sampling points. This may reduce cost and/or processing of data (e.g., collected from unsampled regions).

In some embodiments, the image acquisition device optimizes processing within the device, and may optimize the interface between the device and external devices so as to make efficient use of limited resources available, such as memory and power. In an embedded device, memory is typically limited due to the physical size of the device, as well as cost limitations. Power for the device is usually limited, due to battery limitations or access to a low-power link such as a USB interface. At the same time however, we may wish to acquire many images both of low and high quality iris images since depending on the application and the user, it is uncertain whether and when an optimal image may be acquired. At the same time, images that have already been acquired may provide sufficient information for biometric matching at an accuracy required for a particular application. For efficient processing, the image acquisition device may acquire a set of biometric images over a period of time, and select an image of better quality than some of the others for storage or further processing. For example, the image acquisition device may select an image of better quality for biometric matching, rather than performing matching on all images acquired. Thus, a reduced number of images may be buffered and/or processed on the embedded device.

Figure 70:
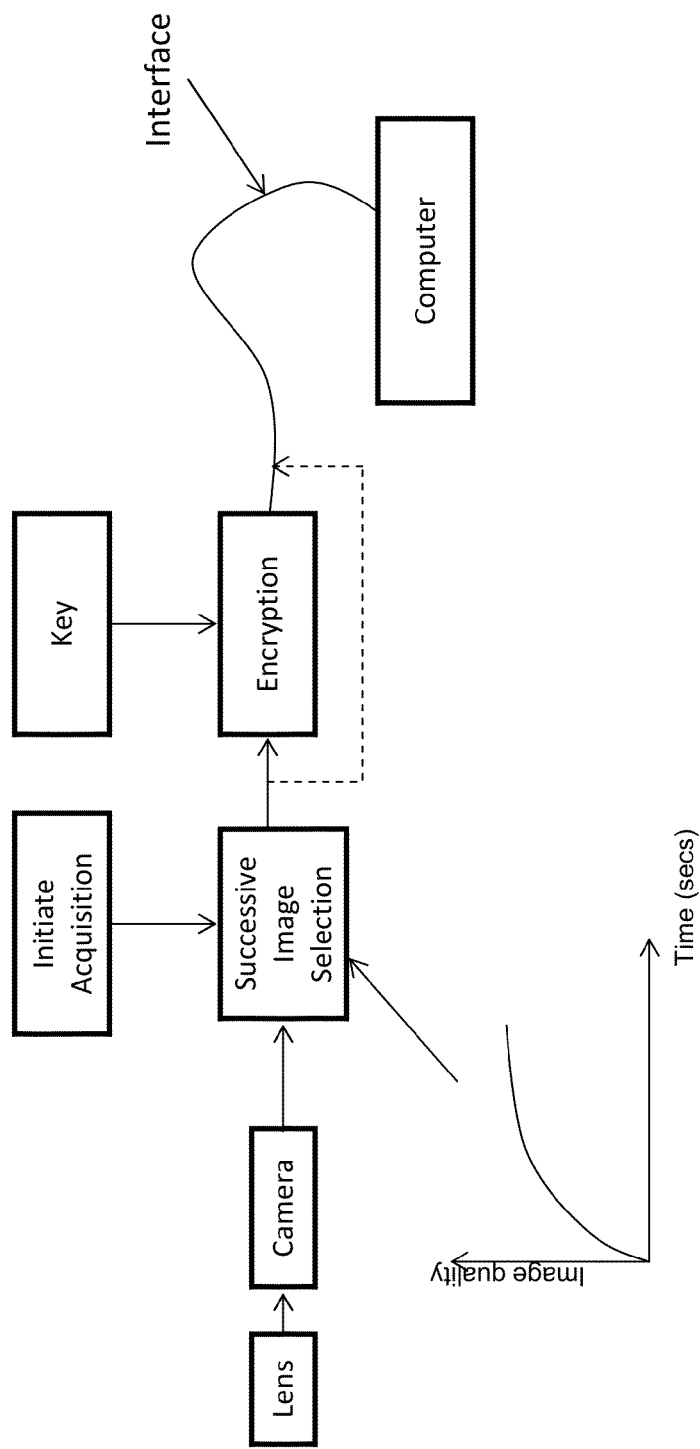
FIG. 70 depicts one embodiment of a system for selecting good quality images for storage and/or further processing.

In some embodiments, one or more of the selected images may be over-written by newly acquired imagery that is of better quality for biometric matching. In this way, memory requirements for buffering or storing images may be reduced, and fewer images can be subsequently processed or transmitted. As discussed above in connection with FIGS. 44-49, various embodiments of systems and methods may select certain images from a plurality of acquired images for storage or further processing. In some embodiments, a reduced number of images resulting from the selection is transferred to a host computer or other computing device. The selected images may be transferred to the host computer or other computing device either after encryption or unprocessed, as shown in FIG. 70. By way of illustration, large amounts of data transferred over a USB interface can occupy substantial CPU and memory resources on the host computer. Thus, reducing the amount of data being transferred may be more efficient.

Figure 71:
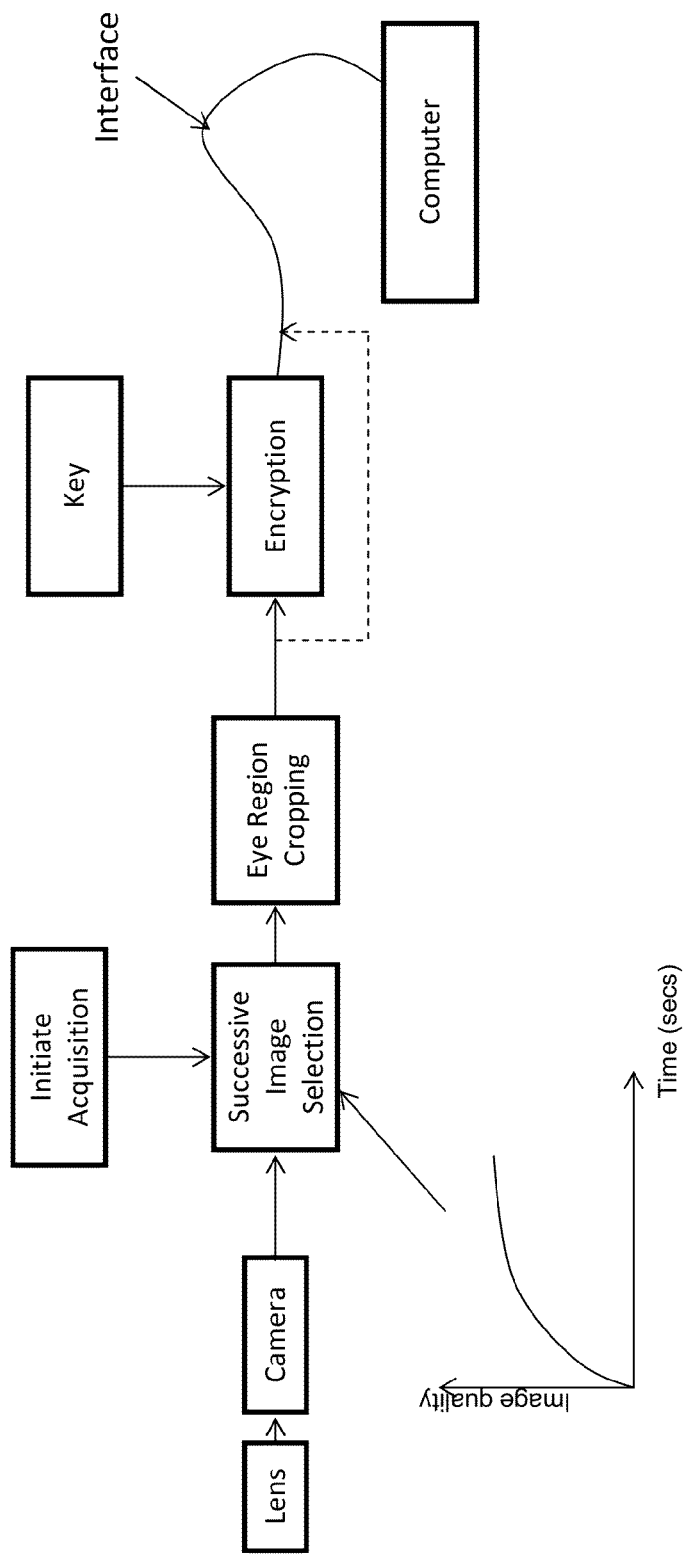
FIG. 71 depicts another embodiment of a system for selecting good quality images for storage and/or further processing.
Figure 72:
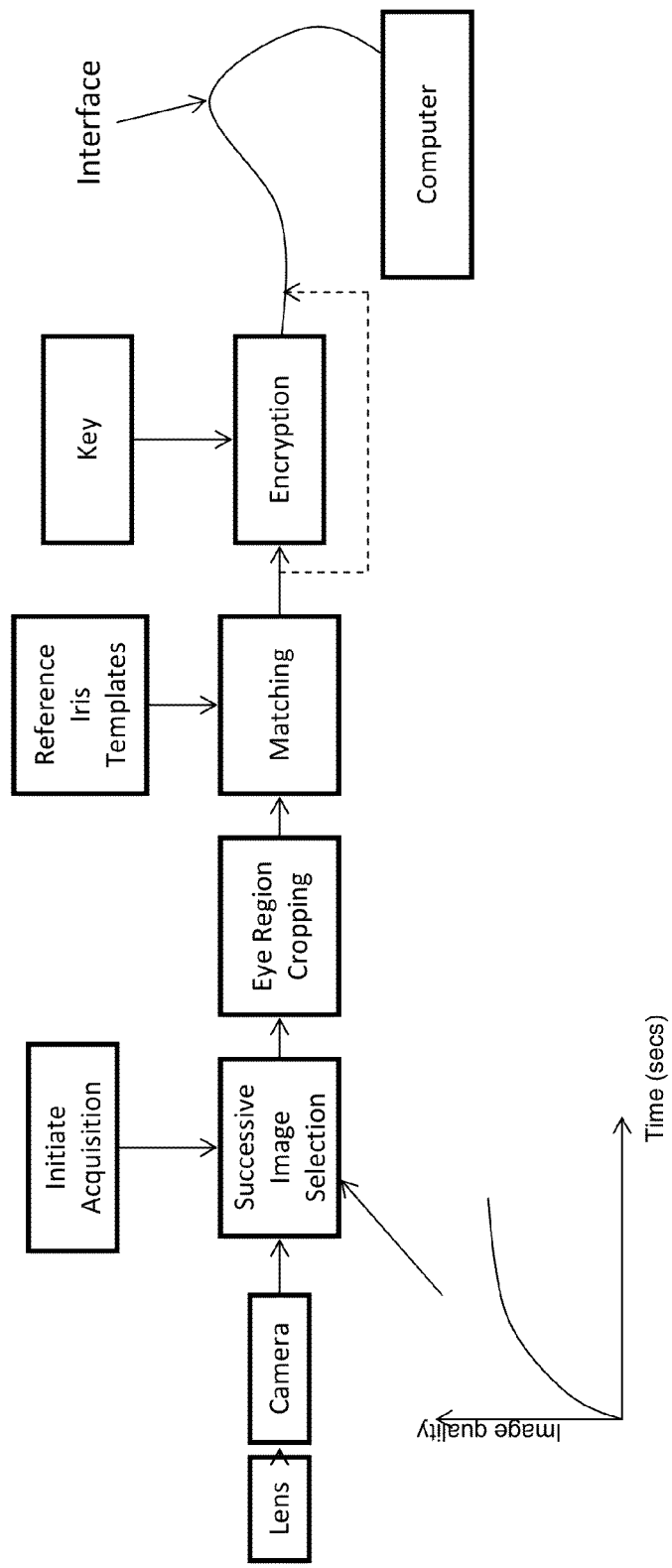
FIG. 72 depicts yet another embodiment of a system for selecting good quality images for storage and/or further processing.

FIG. 71 depicts another embodiment of an image acquisition device. The image acquisition device may select a subset of images acquired, such as those exceeding a predefined quality threshold, or a predefined number of image of better quality for biometric matching that other acquired. This reduced number of images may be subsequently processed such that regions around the eye or iris may be cropped from the images. In some embodiments, only cropped images showing the iris are transferred to the host computer, either encrypted or in raw format. The cropping may further reduce the amount of data being transferred to the host computer. As part of the cropping process, an image processing module on the device may locate the eye or iris from each image. For example, an eye detector may perform object or pattern recognition to identify an eye or iris. In some embodiments, location of the eye or iris may have been identified, or is available from the image selection stage.

In certain embodiments, the reduced number of images may be subsequently processed such that the eye or iris regions are cropped into smaller images. In some embodiments, iris data may be extracted from cropped or uncropped images, and stored or transmitted as a more efficient form than an iris image. In some embodiments, the image acquisition device may perform biometric matching locally on the devices, using either the cropped or uncropped images, or the extracted data. Biometric matching may be performed using reference templates that are stored on or loaded onto the device. In some embodiments, a result of the biometric matching may be displayed on the device or transferred either in raw or encrypted format to a host computer.

Having described certain embodiments of the methods and systems, it will now become apparent to one of skill in the art that other embodiments incorporating the concepts of the invention may be used. It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code.

What is claimed:

1. A method of iris image acquisition, the method comprising:
   (A) acquiring, by a sensor, a plurality of images of a subject, the plurality of images including at least one image of an iris of the subject;
   (B) determining, by at least one processor, a quality metric based at least in part on an estimated area of the iris in the at least one image of the iris of the subject acquired in (A); and
   (C) in response to the quality metric determined in (B):
      (C1) modifying a focus setting of the sensor if the quality metric is lower than a predetermined threshold; and
      (C2) storing, in a memory, the at least one image of the iris of the subject and halting acquisition of the plurality of images of the subject in (A) if the quality metric is higher than the predetermined threshold.

2. The method of claim 1 wherein (A) comprises acquiring images in the plurality of images synchronously at a constant rate.

3. The method of claim 1, wherein (A) comprises acquiring images in the plurality of images asynchronously in response to a computer-controlled trigger signal.

4. The method of claim 1, wherein (A) comprises acquiring images in the plurality of images for a predefined period of time.

5. The method of claim 1, wherein (B) further comprises comparing the quality metric to a predetermined value.

6. The method of claim 1, wherein (C2) comprises overwriting a previously stored image in the memory with the at least one image of the iris of the subject.

7. The method of claim 1, wherein (C2) comprises halting acquisition in response to acquiring images in the plurality of images for a predefined period of time.

8. The method of claim 1, wherein (C2) comprises halting acquisition in response to acquiring a predefined number of images in the plurality of images whose respective quality metrics exceed a predetermined quality threshold.

9. The method of claim 1, wherein:
   (B) further comprises determining a biometric match based on the image of the iris of the subject; and
   (C2) comprises halting acquisition in response to an indication of the biometric match.

10. The method of claim 1, wherein:
    (B) further comprises determining a probability of a correct biometric match based on the image of the iris of the subject; and
    (C2) comprises halting acquisition in response to an indication of the probability of the correct biometric match.

* * * * *